US011859218B2

(12) United States Patent
Moellering et al.

(10) Patent No.: US 11,859,218 B2
(45) Date of Patent: Jan. 2, 2024

(54) RECOMBINANT ALGAE HAVING HIGH LIPID PRODUCTIVITY

(71) Applicant: Synthetic Genomics, Inc., La Jolla, CA (US)

(72) Inventors: Eric R. Moellering, San Diego, CA (US); Saheed Imam, La Jolla, CA (US); Luke Peach, La Jolla, CA (US); Ryan Kalb, La Jolla, CA (US); Sarah Potts, La Jolla, CA (US)

(73) Assignee: Viridos, Inc., La Jolla, CA (US)

( * ) Notice: Subject to any disclaimer, the term of this patent is extended or adjusted under 35 U.S.C. 154(b) by 294 days.

(21) Appl. No.: 17/124,348

(22) Filed: Dec. 16, 2020

(65) Prior Publication Data
US 2021/0180036 A1  Jun. 17, 2021

Related U.S. Application Data

(60) Provisional application No. 62/949,378, filed on Dec. 17, 2019.

(51) Int. Cl.
*C12N 9/16* (2006.01)
*C12N 1/12* (2006.01)
*C12N 9/10* (2006.01)

(52) U.S. Cl.
CPC .......... *C12N 9/16* (2013.01); *C12N 1/12* (2013.01); *C12N 9/1051* (2013.01); *C12Y 204/01216* (2013.01); *C12Y 301/03012* (2013.01)

(58) Field of Classification Search
CPC .... C12Y 301/03012; C12Y 204/01216; C12N 9/1051; C12N 1/12; C12N 9/16
See application file for complete search history.

(56) References Cited

U.S. PATENT DOCUMENTS

| | | |
|---|---|---|
| 9,909,134 B2 | 3/2018 | Messing et al. |
| 2013/0045323 A1* | 2/2013 | Hartel ............ A23L 7/10 426/627 |
| 2013/0227745 A1 | 8/2013 | Frankard et al. |
| 2017/0152520 A1 | 6/2017 | Moellering et al. |
| 2018/0186842 A1* | 7/2018 | Moellering ............ C12P 21/00 |
| 2019/0059390 A1 | 2/2019 | Djonovic et al. |

FOREIGN PATENT DOCUMENTS

WO  WO 2018/204798  11/2018

OTHER PUBLICATIONS

Arriola, Matthew B., et al. "Genome sequences of *Chlorella sorokiniana* UTEX 1602 and *Micractinium conductrix* SAG 241.80: implications to maltose excretion by a green alga." The plant journal 93.3 (2018): 566-586 (Year: 2018).*
Taleb, Ahmed, et al. "Investigation of lipid production by nitrogen-starved Parachlorella kessleri under continuous illumination and day/night cycles for biodiesel application." Journal of applied phycology 30.2 (2018): 761-772 (Year: 2018).*
Hentze, Matthias W., et al. "A brave new world of RNA-binding proteins." Nature reviews Molecular cell biology 19.5 (2018): 327-341 (Year: 2018).*
Filipe Borges and Robert A. Martienssen, "The Expanding World of Small RNAs in Plants," Nat Rev Mol Cell Biol Dec. 2015; 16(12): 727-741, doi:10.1038/nrm4085Ch.
Chary, N. Hicks, G.R., Choi, Y., Carter, D., Raikhel, N., Plant Physiology, Jan. 2008, vol. 146, pp. 97-107.
Figueroa, C. and Lunn, J., Plant Physiology, Sep. 2016, vol. 172, pp. 7-27.
Okano, H., Imai, T., and Okabe, M., Journal of Cell Science, 115, 1355-1359 (2002).
Ota, S., et al., Biotechnol. Biofuels (2016) 9:13 (2016).
Marondedze, C. et al., Sci. Rep. 6, 29766; doi: 10.1038/srep29766 (2016).
PCT International Search Report and Written Opinion in International Application No. PCT/US2020/065323, dated Mar. 10, 2021, 11 pages.

* cited by examiner

*Primary Examiner* — Robert J Yamasaki
*Assistant Examiner* — Trevor Kane
(74) *Attorney, Agent, or Firm* — DLA Piper LLP (US)

(57) ABSTRACT

The invention involves the provision of recombinant algal mutants that have a genetic modification to a nucleic acid sequence encoding a trehalose biosynthetic enzyme, and/or a genetic modification to a nucleic acid encoding an RNA binding domain. And in some embodiments either of these algal mutants can further have a genetic mutation to a nucleic acid sequence encoding an SGI1 polypeptide. Attenuation of one, two, or all three of these genes results in a mutant organism with increased lipid productivity. It was also discovered that one, two, three, or more genetic mutations can be accumulated or "stacked" in a particular mutant cell or organism to result in further increases in the production of lipid products. The lipid products of these mutants are useful as biofuels or for other specialty chemical products.

15 Claims, 7 Drawing Sheets

Specification includes a Sequence Listing.

RECOMBINANT ALGAE HAVING HIGH LIPID PRODUCTIVITY

CROSS-REFERENCE TO RELATED APPLICATIONS

This application claims benefit of priority under 35 U.S.C. § 119(e) of U.S. Ser. No. 62/949,378, filed Dec. 17, 2019, the entire contents of which is incorporated herein by reference in its entirety.

FIELD OF THE INVENTION

The invention involves the provision of a recombinant algal mutant organisms for the production of lipids.

INCORPORATION OF SEQUENCE LISTING

The material in the accompanying sequence listing is hereby incorporated by reference into this application. The accompanying sequence listing text file, name SGI2240_1_Sequence Listing, was created on Dec. 14, 2020, and is 129 kb. The file can be accessed using Microsoft Word on a computer that uses Windows OS.

BACKGROUND OF THE INVENTION

The production of biodiesel fuels presents great opportunities to develop environmentally sound sources of energy that can be obtained at reasonable cost. Efforts have been directed towards using algae or other microorganisms to produce hydrocarbons that can be used as biodiesel due to their high lipid content. Additional specialty chemicals can also be obtained from these organisms and for use in consumer products.

Since algae use energy from sunlight to combine water and carbon dioxide to produce biomass, achieving increased productivity offers the possibility of a carbon neutral fuel source. The development of algal strains with very high lipid productivity for the production of algal-sourced biofuels therefore presents the possibility of a significant reduction in carbon dioxide released into the atmosphere and a consequent reduction in the problem of global warming.

Strategies for increasing algal production of biofuels and other products have included modification of nutrition provided to the organisms, such as cultivating the organisms in nitrogen, phosphorus, or silicon deficient media. Other strategies have included modification of cultivation or environmental protocols, or various efforts directed towards genetic engineering of the organisms. However, wild type algal strains have not been sufficiently productive to permit an economically viable development of this resource. Higher levels of cell productivity are necessary to efficiently utilize this energy source and achieving sufficient productivity remains an important barrier.

SUMMARY OF THE INVENTION

The invention involves methods and recombinant algal mutants that have a genetic modification to a nucleic acid sequence encoding a trehalose biosynthetic enzyme, and/or a genetic modification to a nucleic acid encoding an RNA binding domain. Attenuation of either or both of these genes results in a mutant organism with increased lipid productivity. It was also discovered that one, two, three, or more genetic mutations can be accumulated or "stacked" in a particular mutant cell or organism to result in further increases in the production of lipid products. The lipid products of these mutants can be utilized as biofuels or for other specialty chemical products. In some embodiments the recombinant algal mutants that have a genetic modification in a nucleic acid sequence encoding a trehalose biosynthetic enzyme or can have a genetic modification in a nucleic acid sequence encoding an RNA binding domain. In other embodiments the algal mutants can have both of these genetic modifications. And in some embodiments, any of these algal mutants can additionally (and optionally) have a genetic mutation to a nucleic acid sequence encoding an SGI1 polypeptide. Each of these algal mutants exhibit increased lipid productivity versus a control algae.

In a first aspect the invention provides a recombinant algal cell having a genetic modification in a nucleic acid sequence encoding a trehalose biosynthesis pathway enzyme; and/or a genetic modification in a nucleic acid sequence encoding an RNA binding domain; wherein the recombinant alga exhibits increased lipid productivity versus a corresponding control algal cell. In one embodiment the genetic modification results in an attenuation of expression of the nucleic acid sequence having the genetic modification. In one embodiment the recombinant alga can has a genetic modification in the nucleic acid sequence encoding the trehalose biosynthesis pathway enzyme and a genetic modification in the nucleic acid sequence encoding the RNA binding domain. In any of the embodiments the recombinant alga can be a Chlorophyte alga and, optionally, of the Class Trebouxiophyceae.

In various embodiments the trehalose biosynthesis pathway enzyme can be any one of a trehalose-6-phosphate synthase, or a trehalose-6-phosphate phosphatase, or a trehalose-6-phosphate synthase/phosphatase. In any of the embodiments the recombinant alga can further have an attenuation of a nucleic acid sequence encoding an SGI1 polypeptide. In one embodiment the recombinant alga has a genetic modification in a nucleic acid sequence encoding a trehalose biosynthesis pathway enzyme (e.g. trehalose-6-phosphate synthase/phosphatase), and a genetic modification in a nucleic acid sequence encoding an RNA binding domain, and an attenuation of a nucleic acid sequence encoding an SGI1 polypeptide, and the recombinant alga exhibits increased lipid productivity versus a corresponding control algal cell.

In one embodiment the genetic modification to the nucleic acid sequence encoding the RNA binding domain is a functional deletion. In one embodiment the nucleic acid sequence encoding the trehalose-6-phosphate synthase/phosphatase can have a substitution mutation versus the wild type sequence. In any of the embodiments the nucleic acid sequence encoding the trehalose-6-phosphate synthase phosphatase can have at least 90% sequence identity to SEQ ID NO: 2. In any of the embodiments the nucleic acid sequence encoding the RNA binding domain can have at least 90% sequence identity to SEQ ID NO: 1.

In some embodiments the substitution mutation in the nucleic acid sequence encoding the trehalose-6-phosphate synthase phosphatase is a E723V mutation versus the wild type sequence, and the recombinant algal cell is an alga of the genus *Parachlorella*. The genetic modification of the nucleic acid sequence encoding the trehalose biosynthetic enzyme and the nucleic acid sequence encoding the RNA binding domain can result in an attenuation in the expression of each of the nucleic acid sequences. In various embodiments the recombinant alga has at least 50% or at least 60% or at least 70% or at least 80% or at least 90% or at least 2× greater lipid productivity versus a control algae. And in some embodiments the recombinant alga can have (alone or in addition to greater lipid productivity) at least 50% or at least 60% or at least 70% or at least 80% or at least 90% or at least 2× greater biomass productivity versus a control algae. In some embodiments the recombinant alga has at least 5 grams per square meter per day of lipid production. The recombinant alga can also have a higher biomass productivity per unit time versus a control alga. The recombinant alga can have the stated higher biomass productivity and/or the stated higher total organic carbon production under nitrogen deficient conditions.

In various embodiments the recombinant alga can be a Chlorophyte algae of any of the genera selected from *Chlorella, Parachlorella, Picochlorum, Tetraselmis,* and *Oocystis*.

In another aspect the invention provides a method of producing a composition containing lipids. The methods involve cultivating an algal organism having a genetic modification in a nucleic acid sequence encoding a trehalose biosynthetic enzyme and/or a genetic modification in a nucleic acid sequence encoding an RNA binding domain; and thereby producing a composition containing lipids. In any embodiment the algal organism can also have an attenuation in expression of a nucleic acid sequence encoding an SGI1 polypeptide. Any organism described herein can be cultivated or used in the methods.

In another aspect the invention involves methods of producing a recombinant lipid-producing algal organism. The methods involve introducing a genetic modification into a nucleic acid sequence encoding a trehalose biosynthetic enzyme in an algal organism, and/or introducing a genetic modification into a nucleic acid sequence encoding an RNA binding domain in an algal organism, wherein the genetic modification(s) is/are relative to a corresponding control algal organism; to thereby produce a recombinant lipid-producing algal organism; and wherein the recombinant algal organism exhibits increased lipid productivity versus a corresponding control algal organism not having the attenuation(s). Any organism described herein can be produced in the methods.

In one embodiment the methods involve introducing a genetic modification into the nucleic acid sequence encoding the trehalose biosynthetic pathway enzyme and also introducing a genetic modification into the nucleic acid sequence encoding the RNA binding domain. The methods can also involve cultivating the recombinant algal organism to thereby produce a composition containing lipids. In one embodiment the genetic modification(s) is/are introduced by mutagenesis. In any embodiment the algal organism is a Chlorophyte alga. In various embodiments the trehalose biosynthesis pathway enzyme can be trehalose-6-phosphate synthase, a trehalose-6-phosphate phosphatase, or a trehalose-6-phosphate synthase/phosphatase. In any of the embodiments the methods can also involve introducing a genetic modification into a nucleic acid sequence encoding an SGI1 polypeptide.

In some embodiments the genetic modification(s) to any one or more of the nucleic acid sequences is a functional deletion. In one embodiment the trehalose-6-phosphate biosynthetic enzyme is synthase/phosphatase and its genetic modification is a substitution mutation versus the wild type sequence. In one embodiment the nucleic acid sequence encoding the trehalose-6-phosphate synthase phosphatase has at least 90% sequence identity to SEQ ID NO: 2. In any embodiment the nucleic acid sequence of the algal organism encoding the RNA binding domain is a functional deletion. The nucleic acid sequence encoding the RNA binding domain in the algal organism can have at least 90% sequence identity to SEQ ID NO: 1.

In any of the embodiments the alga can be of the Class Trebouxiophyceae. In one embodiment the substitution mutation in the nucleic acid sequence encoding the trehalose-6-phosphate synthase phosphatase is an E723V mutation and the recombinant algal cell is an alga of the genus *Parachlorella*. In any embodiment the genetic modification(s) can be an attenuation in the expression of the nucleic acid sequence(s). In various embodiments the algal organism can have at least 50% greater lipid productivity versus the corresponding control algal, or at least 75% greater lipid productivity versus the corresponding control alga. The algal organism can also have at least 5 grams per square meter per day of lipid production. The algal organism can have higher biomass productivity per unit time and/or higher biomass productivity under nitrogen deficient conditions and/or higher total organic carbon production under nitrogen deficient conditions.

In any of the embodiments the recombinant alga can be a Chlorophyte alga of a genus selected from the group consisting of: *Chlorella, Parachlorella, Picochlorum, Tetraselmis,* and *Oocystis*. In one embodiment the recombinant alga is an alga of the class Chlorellales.

In one embodiment the method further involves a step of treating the algal organism with uv radiation prior to the step of cultivating. The method can also involve harvesting a lipidic composition from the algal organism.

BRIEF DESCRIPTION OF THE DRAWINGS

In FIG. 2B, RBD repair in the SGI1+Tre6P+RBD strain resulted in increased FAME productivity for the first few days of nitrogen starvation until falling to the same levels as the SGI1-KO strain by Day 6. FIG. 2C shows the results for semi-continuous urea batch assay under 2 days of nitrogen deplete conditions for the triple mutation strain (STR0600, i.e. SGI1+RBD+Tre6P mutations) compared to the wild-type *Parachlorella* sp. strain. FAME production for STR600 was 53% higher.

In FIG. 3A RBD recapitulation strain (SGI1+RBD) shows areal FAME productivity equivalent to the SGI1 mutant in the early stages of nitrogen starvation but increases to almost to the levels of the triple mutant (STR00600) levels by Day 6. In the SGI1+RBD strain, the RBD SNP was introduced into a SGI1-only strain. In FIG. 3B, Tre6P repair in the STR0600 triple mutant showed decreased FAME productivity relative to triple mutant STR0600 early in nitrogen starvation but approaches the same level as the triple mutant by Day 5.

FIG. 4A shows increased FAME productivity for the SGI1-KO/RBD/Tre6P stacked mutation strains, similar to the triple mutant STR0600. FIG. 4B shows TOC data for the same.

FIG. 5A shows the STR600 triple mutant (SGI1+RBD+Tre6P) versus SGI1 repair strains 680 and 681 (which have SGI1 mutation repaired) and repair strain 682 (which has RBD mutation repaired). FAME accumulation after 2 days is reduced for the repair strains versus the triple mutant (STR0600), but still higher than the SGI1-only mutants. FIG. 5B shows similar data with respect to TOC accumulation after 2 days.

DETAILED DESCRIPTION OF THE INVENTION

Figure 1A:
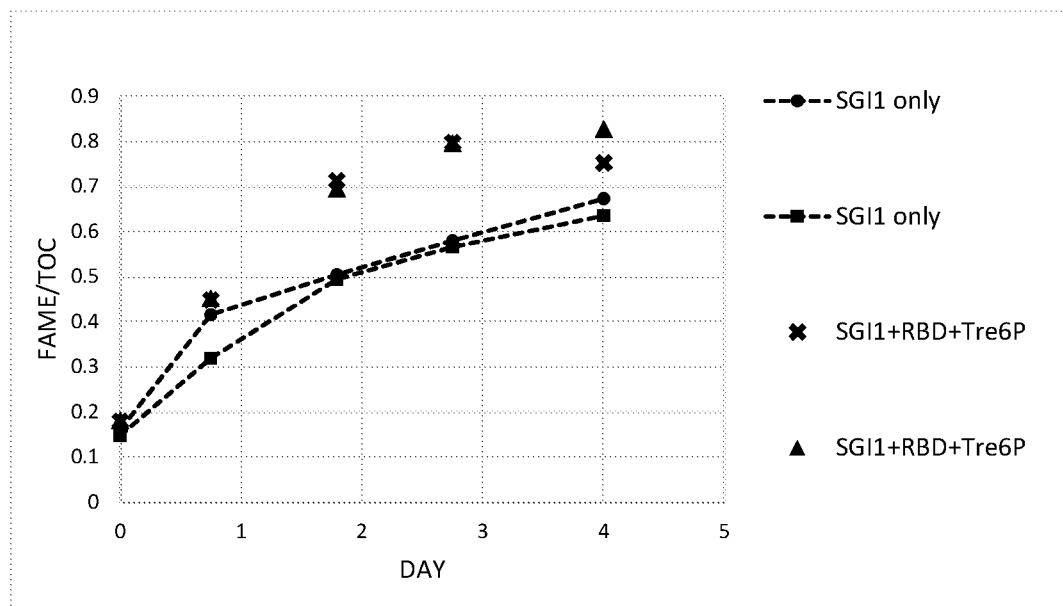
FIG. 1A provides a graphical illustration of a FAME/TOC productivity plot for strains isolated from BODIPY-FACS enrichment after 2-days of nitrogen deplete conditions, showing the amount of fixed carbon that is partitioned to lipids and nitrogen-deplete lipid productivity.

The invention provides recombinant algal mutants that have a genetic modification to a nucleic acid sequence encoding a trehalose biosynthetic pathway enzyme, and/or a genetic modification to a nucleic acid encoding an RNA binding domain. A genetic modification to either or both of these genes as described herein results in a recombinant or mutant cell or organism with higher productivity, for example higher lipid productivity. The recombinant cells or organisms can also have a higher biomass productivity. The recombinant algal mutants can also optionally have reduced chlorophyll content and/or a reduced PSII antenna size. Any of the algal mutants described herein can also, optionally, have an attenuation of a gene encoding an SGI1 polypeptide. Thus, in some embodiments the algal mutants have 1) a genetic modification to a nucleic acid sequence encoding a trehalose biosynthetic pathway enzyme, and/or 2) a genetic modification to a nucleic acid encoding an RNA binding domain; and, additionally and optionally 3) a genetic modification in a gene encoding an SGI1 polypeptide. Any of the recombinant cells or organisms disclosed herein can be mutant photosynthetic organisms. It was discovered unexpectedly that the genetic mutations disclosed herein can be accumulated or "stacked" in a cell or organism to result in further significant increases in the production of lipid products made by the cells or organisms, which further increases can be additive, more than additive, synergistic, or exponential. The stacking can be performed by recapitulating more than one of the mutations in a wild-type or other background cell or organism. The recombinant algal cells or organisms disclosed can have one, two, three, or more than two, or more than three genetic mutations described herein, and thus can have the desirable characteristics disclosed herein.

The recombinant cells or organisms of the invention can have higher FAME and/or biomass productivity than corresponding control cells or organisms that do not have a corresponding attenuation(s) of the nucleic acid sequence encoding an RBD domain and/or a nucleic acid sequence encoding a trehalose biosynthetic pathway enzyme and, optionally with either or both, a nucleic acid sequence encoding an SGI1 polypeptide, or any combination or sub-combination of these attenuations, and that are cultivated in the same or substantially the same conditions. Biomass productivity can be measured as the rate of biomass accumulation, for example, the total organic carbon content of the respective cells or organisms, which in one embodiment can be in batch cultures. Batch culture is a culture where nutrients are not renewed or re-supplied to the medium during the time period the cells or organisms are cultured. Any of the mutant cells or organisms disclosed herein can be photosynthetic cells or organisms. Any of the recombinant cells or organisms described herein can exhibit increased lipid and/or biomass productivity under photoautotrophic conditions. Corresponding (control) cells or organisms are useful for evaluating the effect of any one or more genetic modifications. Corresponding (control) cells or organisms do not have the one or more genetic modifications being evaluated and are subjected to the same or substantially the same culturing conditions as the test cells or organisms such that a difference in the performance of the cells or organisms is based only on the genetic modification(s) being evaluated. Corresponding (control) cells or organisms can be of the same species as the test organism. They can also be the same or similar in every way except for the one or more genetic modification(s) being evaluated. In some embodiments the corresponding (control) cell or organism is a wild-type cell or organism.

In one embodiment the recombinant cells or organisms are algal cells. In one embodiment the recombinant alga has a genetic modification to a nucleic acid sequence encoding a trehalose biosynthetic enzyme. In another embodiment the recombinant alga has a genetic modification to a nucleic acid sequence encoding a RNA binding domain. In another embodiment the recombinant alga can have a genetic modification to a nucleic acid encoding a trehalose biosynthetic pathway enzyme and a genetic modification to a nucleic acid sequence encoding an RNA binding domain. Additionally, and optionally any of the recombinant alga can further have a genetic modification to a nucleic acid sequence encoding an SGI1 polypeptide with the genetic modification encoding an RNA binding domain and/or a genetic modification to a nucleic acid encoding a trehalose biosynthetic pathway enzyme.

The lipid products of these mutants can be further processed into biofuels or used in the production of other specialty chemical products. The nucleic acid sequences encoding the trehalose biosynthetic pathway enzyme, or the RNA binding domain, or the SGI1 polypeptide can be any of the nucleic acid sequences described herein, hereby disclosed in all possible combinations and sub-combinations.

In some embodiments any of the recombinant cells or organisms of the invention have a reduced amount of chlorophyll b, and can have an increased chlorophyll a: chlorophyll b ratio compared to a corresponding control cell or organism. The recombinant cells or organisms can have decreased photosynthetic antenna size, for example reduced photosystem II (PSII) and/or reduced photosystem I (PSI) antenna size. In various embodiments the cross-sectional unit size of the PSII and/or PSI antenna of the recombinant cells or organisms disclosed herein can be reduced by at least 10%, at least 20%, at least 30%, at least 25%, at least 30%, at least 35%, at least 40%, at least 45%, at least 50%, or at least 60% compared to the PSII and/or PSI antenna size of a corresponding control cell or organism. The recombinant cells or organisms can have higher growth rate and/or higher biomass productivity than a corresponding control cell or organism not having the genetic modification, for example, higher biomass productivity per hour or per day or per period of 2 days or 3 days or 4 days or 5 days or 6 days. "Biomass" refers to cellular mass, whether of living or dead cells. Biomass productivity, or biomass accumulation, or growth rate, can be measured by any means accepted in the art, for example as ash free dry weight (AFDW), dry weight, wet weight, or total organic carbon (TOC) productivity. In any embodiment biomass productivity, or biomass accumulation, or the growth rate, can be measured as total organic carbon (TOC) productivity.

The recombinant cells or organisms of the invention can produce a greater amount of a bioproduct per time period (e.g. per minute or per hour or per day or per period of 2 days or 3 days or 4 days or 5 days or 6 days), for example a lipid product, FAME profile, a carbohydrate, a protein product, a polyketide, a terpenoid, a pigment, an antioxidant, a vitamin, one or more nucleotides, one or more nucleic acids, one or more amino acids, one or more carbohydrates, an alcohol, a hormone, a cytokine, a peptide, or a polymer than a corresponding (control) organism not having the genetic modification(s) and being tested and cultured under substantially the same conditions over the same period of time. The amount of product can be expressed as g/time period, mg/time period, ug/time period, or any other defined quantity per defined time period described herein. Such bioproducts can be isolated from a lysate of any of the recombinant cells or organisms of the invention. In some embodiments, the recombinant cells or organisms of the invention produce at least 10%, at least 15%, at least 20%, at least 25%, at least 30%, at least 35%, at least 40%, at least 45%, at least 50%, at least 60%, at least 70%, at least 80%, at least 90% or at least 100% more of a bioproduct than a corresponding control alga cultured under the substantially the same conditions, which can be batch, semi-continuous, or continuous culture conditions and may be nutrient replete culture conditions or may be nitrogen deplete conditions, and may be photoautotrophic conditions.

Without wanting to be bound by any particular theory it is believed that the genetic modification(s) described herein result(s) in an attenuation of expression of a nucleic acid sequence encoding the trehalose biosynthetic pathway enzyme and/or a nucleic acid sequence encoding the RNA binding domain and, optionally with either or both, a nucleic acid sequence encoding the SGI1 polypeptide. These one or more attenuations result in a significant increase in the amount of lipids produced by the cell, as demonstrated by the total FAME produced by the cell. They can also result in a significant increase in biomass productivity, as demonstrated by the organic carbon produced by the cell (as measured, for example, by total organic carbon).

As used herein, "exogenous" with respect to a nucleic acid or gene indicates that the nucleic acid or gene has been introduced (e.g. "transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. A "heterologous" nucleic acid can also be an exogenous synthetic sequence not found in the species into which it is introduced. An exogenous nucleic acid can also be a sequence that is homologous to an organism (i.e., the nucleic acid sequence occurs naturally in that species or encodes a polypeptide that occurs naturally in the host species) that has been isolated and subsequently reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively, or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in Nature; 3) has been engineered using molecular biology techniques such that it lacks one or more nucleotides with respect to the naturally occurring nucleic acid molecule sequence; and/or 4) has been manipulated using molecular biology techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the terms "transgenic" "transformed" or "recombinant" or "engineered" or "genetically engineered" refer to organisms that have been manipulated by introduction of an exogenous or recombinant nucleic acid sequence into the organism, or by genetic manipulation of native sequences (which are therefore then recombinant). In some embodiments the exogenous or recombinant nucleic acid can express a heterologous protein product. Non-limiting examples of such manipulations include gene knockouts, targeted mutations and gene replacement, gene replacement, promoter replacement, deletions or insertions, disruptions in a gene or regulatory sequence, as well as introduction of transgenes into the organism. For example, a transgenic microorganism can include an introduced exogenous regulatory sequence that enables transcription in the organism operably linked to an endogenous gene of the transgenic microorganism. Recombinant or genetically engineered organisms can also be organisms into which constructs for gene "knock down," deletion, attenuation, or disruption have been introduced to perform the indicated manipulation. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome, or can be present on a vector or other nucleic acid construct. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. Pfam domains and families are identified using multiple sequence alignments and hidden Markov models (HMMs). Pfam-A family or domain assignments are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) Nucleic Acids Research 26, 320-322; Bateman (2000) Nucleic Acids Research 26, 263-266; Bateman (2004) Nucleic Acids Research 32, Database Issue, D138-D141; Finn (2006) Nucleic Acids Research Database Issue 34, D247-251; Finn (2010) Nucleic Acids Research Database Issue 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

The recombinant cells or organisms described herein can be generated by human intervention, for example, by classical mutagenesis or genetic engineering, or by any feasible mutagenesis method, including but not limited to UV irradiation, CRISPR/Cas9, cre/lox, gamma irradiation, or chemical mutagenesis. And screening methods can be used to identify mutants having desirable characteristics (e.g., reduced chlorophyll and increased productivity. Methods for generating mutants of photosynthetic organisms using classical mutagenesis, genetic engineering, and phenotype or genotype screening are well-known in the art.

Algal Cell or Organism

The recombinant algal cell or organism of the invention can be a mutant microalga, or a mutant photosynthetic organism, or a mutant green alga. The recombinant alga can be any eukaryotic microoalga such as, but not limited to, a Chlorophyte, an Ochrophyte, or a Charophyte alga. In some embodiments the mutant microalga can be a Chlorophyte alga of the taxonomic Class Chlorophyceace, or of the Class Chlorodendrophyceae, or the Class Prasinophyceace, or the Class Trebouxiophyceae, or the Class Eustigmatophyceae. In some embodiments, the mutant microalga can be a member of the Class Chlorophyceace, such as a species of any one or more of the genera *Asteromonas, Ankistrodesmus, Carteria, Chlamydomonas, Chlorococcum, Chlorogonium, Chlorodendrales, Chloroellales, Chrysosphaera, Dunaliella, Haematococcus, Monoraphidium, Neochloris, Oedogonium, Pelagomonas, Pleurococcus, Pyrobotrys, Scenedesmus,* or *Volvox*. In other embodiments, the mutant microalga can be a member of the Class Chlorodendrophyceae, such as a species of any one or more of the genera *Prasinocladus, Scherffelia,* or *Tetraselmis*. In further alternative embodiments, the mutant alga can be a member of the Class Prasinophyceace, optionally a species of any one or more of the genera *Ostreococcus* or *Micromonas*. Further alternatively, the mutant microalga can be a member of the Class Trebouxiophyceae, and optionally of the Order Chlorellales, and optionally a genera selected from any one or more of *Botryococcus, Chlorella, Auxenochlorella, Heveochlorella, Marinichlorella, Oocystis, Parachlorella, Pseudochlorella, Tetrachlorella, Eremosphaera, Franceia, Micractinium, Nannochloris, Picochlorum, Prototheca, Stichococcus,* or *Viridiella*, or any of all possible combinations or sub-combination of the genera. In another embodiment the recombinant alga is a Chlorophyte alga of the Class Trebouxiophyceae, the Order Chlorellales, the Family Oocystaceae, Chlorellaceae, or Eustigmatophyceae, and optionally a genera selected from one or more of *Oocystis, Parachlorella, Picochlorum, Nannochloropsis,* and *Tetraselmis*. The recombinant alga can also be from the genus *Oocystis*, or the genus *Parachlorella*, or the genus *Picochlorum*, or the genus *Tetraselmis*, or from any of all possible combinations and sub-combinations of the genera.

In various embodiments the recombinant alga of the invention can have a genetic modification to a nucleic acid encoding a trehalose biosynthetic enzyme, or an RNA binding protein, or both. Any of the recombinant alga of the invention can also, optionally, have a genetic modification to a nucleic acid encoding an SGI1 polypeptide. In one embodiment the recombinant alga of the invention has a genetic modification to a nucleic acid sequence encoding a trehalose biosynthetic enzyme, a genetic modification to a nucleic acid sequence encoding an RNA binding protein, and a genetic modification to a nucleic acid encoding an SGI1 polypeptide. In one embodiment each of these genetic modifications is to a native or endogenous sequence of the cell or organism.

A "genetic modification" can denote any one or more of a deletion, a mutation, a disruption, an insertion, an inactivation, an attenuation, a rearrangement, one or more point mutations, a frameshift mutation, an inversion, a "knock out", a "knock in", that results in a physical change to the modified gene, and that reduces or eliminates expression of the one or more gene products. The genetic modification (e.g. to a gene or nucleic acid sequence encoding a trehalose biosynthetic pathway enzyme or RBD domain, or SGI1 polypeptide) can occur in any sequence that affects expression of the gene or the nature or quantity of its product, for example to the coding or non-coding sequence, regulatory sequence, promoter, terminator, exon, intron, 3' or 5' UTR. The genetic modification can be to the host cell's native genome. In some embodiments, for example, a recombinant cell or organism having attenuated expression of a gene as disclosed herein can have one or more mutations, which can be one or more nucleobase changes and/or one or more nucleobase deletions and/or one or more nucleobase insertions, into the region of a gene 5' of the transcriptional start site, such as, in non-limiting examples, within about 2 kb, within about 1.5 kb, within about 1 kb, or within about 0.5 kb of the known or putative transcriptional start site, or within about 3 kb, within about 2.5 kb, within about 2 kb, within about 1.5 kb, within about 1 kb, or within about 0.5 kb of the translational start site.

In one embodiment the genetic modification(s) can be an attenuation (but the genetic modification(s) can also be a deletion or a disruption). An "attenuation" refers to a nucleic acid sequence or gene whose function, activity, or expression is reduced compared to the amount of function, activity, or expression in a corresponding (control) organism not having the genetic modification being examined, where the cell is cultivated under the same or substantially the same conditions, i.e. the diminished function, activity, or expression is due to the genetic modification. In various embodiments an attenuated nucleic acid sequence or gene produces less than 70% or less than 50% or less than 30% or less than 20% or less than 10% or less than 5% or less than 1% of its function, activity, or expression than in a corresponding cell not having the genetic modification at issue under the same or substantially the same culturing conditions. The terms deletion cassette and disruption cassette are used interchangeably. Substantially the same conditions can be the same conditions or slightly different conditions where the change does not materially affect the function, activity, or expression of the nucleic acid sequence modified.

In various embodiments the genetic modification can be a deletion or a disruption. An unmodified nucleic acid sequence present naturally in the organism denotes a natural, endogenous, or wild type sequence. In a deletion at least part of the nucleic acid sequence is deleted, but a deletion can also be accomplished by disrupting a gene (e.g. a "knock out" mutation), or through, for example, the insertion (insertional mutation) of another sequence (e.g. a selection marker), or a combination of deletion and insertion, but a deletion can also be performed by other genetic modifications known to those of ordinary skill that result in the gene not being functionally expressed. A "disruption" of a gene is a functional deletion by insertion or deletion of a nucleotide sequence into or from the coding, non-coding, or regulatory portion of a gene with resulting partial or complete loss of function, activity, or expression of the gene. Functional expression refers to the expression of a functional product or activity of a nucleic acid sequence; when the expressed product of a nucleic acid is a polypeptide a functional polypeptide has at least some of the normal activity of the encoded polypeptide. For a nucleic acid a functional activity is at least some of the normal activity of the nucleic acid. A functional deletion or disruption removes at least so much of the expression or activity of a nucleic acid sequence that the product or activity of the nucleic acid sequence has no significant effect on the cell or organism compared to the natural or normal level of expression, i.e. the cell performs the same as a "knock out" deletion or disruption (e.g. with regard to lipid productivity or biomass productivity). When the nucleic acid sequence encodes a polypeptide, the encoded polypeptide will not be expressed in an amount that makes a significant difference in the cell or organism compared to expression in the unmodified cell or organism. When the nucleic acid sequence has an activity other than encoding a polypeptide the activity is not sufficient to display a significant effect compared to activity in the unmodified cell or organism. In some embodiments the functional deletion can remove all expression or activity of the nucleic acid sequence. In some embodiments the functional deletion is a knockout deletion. Thus, deletions, functional deletions, and disruptions can also be attenuations.

The recombinant cells or organisms of the invention can have a reduced functional absorption cross section of PSII or reduced PSII antenna size. For example, the cross-sectional unit size of the PSII antenna can be reduced by at least about 10%, at least 20%, at least 30%, at least 25%, at least 30%, at least 35%, at least 40%, at least 45%, at least 50%, at least 60%, at least about 70%, or at least about 80% compared to the PSII antenna size of the corresponding (control) cell or organism. The recombinant cells or organisms of the invention can additionally have a reduced functional absorption cross section of PSI or reduced PSI antenna size. For example, the cross-sectional unit size of the PSI antenna can be reduced by at least 10%, at least 20%, at least 30%, at least 25%, at least 30%, at least 35%, at least 40%, at least 45%, at least 50%, or at least 60% compared to the PSI antenna size of a control photosynthetic organism.

In various embodiments, a mutant photosynthetic organism as provided herein can have increased Fv/Fm with respect to a corresponding control photosynthetic organism. For example, the mutant photosynthetic organism may have Fv/Fm increased by at least 5%, at least 10%, at least 12%, at least 15%, at least 20%, at least 30%, at least 40% or at least 50% compared to a corresponding (control) photosynthetic organism. In various embodiments the Fv/Fm can be increased by between about 5% and about 50%, or between about 5% and 30%, or between 5% and 20% with respect to a control photosynthetic organism.

Further, a mutant photosynthetic organism as provided herein can have an increased rate of electron transport on the acceptor side of photosystem II with respect to a control or wild type cell. The rate can be at least about 20%, 30%, 40%, 50%, 60%, 80%, or 100% higher compared to a corresponding control or wild type organism. In addition, mutant photosynthetic cells or organisms of the invention can have a rate of carbon fixation (Pmax (C)) in a recombinant cell or organism as provided herein can be elevated with respect to a control organism. For example, Pmax (14C) can be increased by at least about 20%, 30%, 40%, 50%, 60%, 80%, or 100% compared to a corresponding control or wild type organism.

In some embodiments, the recombinant cells or organisms of the invention have decreased PSI and/or PSII antenna size and can optionally also have a higher amount of a ribulose bisphosphate carboxylase activase (Rubisco activase or "RA") than a corresponding (control) or wild type organism, for example, at least 1.2, 1.4, 1.6, 1.8, 2, 2.2, or 2.5 fold the amount of RA as a control organism. In some embodiments, the mutants demonstrate reduced expression of 6, 8, 10, 12, or 14 LHCP genes and increased expression of an RA gene, such as an RA-a or RA-P gene. Thus, the recombinant cells or organisms of the invention can be mutant photosynthetic organisms having reduced chlorophyll and reduced PSII antenna size where the mutants have a higher amount of Rubisco activase than control photosynthetic organisms.

The LHC super-gene family encodes the light-harvesting chlorophyll a/b-binding (LHC) proteins that constitute the antenna system of the photosynthetic apparatus. A recombinant algal mutant of the invention can also have a reduced expression of LHC genes. Thus, in some embodiments the recombinant cells or organisms of the invention have at least 6, at least 8, at least 10, or at least 12 LHC genes that are attenuated or downregulated with respect to their expression level in a corresponding (control) cell or organism. In various embodiments the reduction in expression of the LHC genes can be a reduction of at least 20%, or at least 30%, or at least 40%, or at least 50%, or at least 60%, or at least 70% in the level of LHC transcripts.

Trehalose Biosynthetic Pathway Enzymes

The biosynthesis of trehalose is an important process and several biosynthesis pathways for the provision of trehalose have developed. The most common biosynthesis pathways involve trehalose biosynthetic pathway enzymes, which include: 1) trehalose-6-phosphate synthase (T6PS), which converts glucose-6-phosphate and UDP-glucose into trehalose-6-phosphate (T6P); 2) trehalose-6-phosphate phosphatase (T6PP), which dephosphorylates T6P into trehalose; 3) trehalase, which converts trehalose into glucose; 4) trehalose phosphate hydrolase, which converts T6P into glucose and UDPG+glucose-6-phosphate; and 5) trehalose-6-phosphate synthase/phosphatase (T6PS/P), which has both the synthase and phosphatase activity of 1) and 2) above in the same enzyme molecule.

The recombinant alga of the invention can have a genetic modification to a gene or nucleic acid sequence encoding any one or more of the trehalose biosynthetic pathway enzymes or any combination of them, which are hereby disclosed in all possible combinations and sub-combinations as if set forth fully herein. In one embodiment the genetic modification is to one or more gene(s) or nucleic acid sequence(s) encoding a trehalose-6-phosphate synthase (T6PS). In another embodiment the genetic modification is to one or more nucleic acid sequence(s) or gene(s) encoding a trehalose-6-phosphate phosphatase (T6PP). In another embodiment the genetic modification is to one or more nucleic acid sequence(s) or gene(s) encoding a trehalose-6-phosphate synthase/phosphatase (T6PS/P). In another embodiment the genetic modification is to one or more nucleic acid sequence(s) or gene(s) encoding a trehalose phosphate hydrolase. In another embodiment the genetic modification is to one or more nucleic acid sequence(s) or gene(s) encoding a trehalase. In some embodiments the genetic modification can be to a promoter, terminator, binding site, or other regulatory sequence for a gene encoding the named biosynthetic pathway enzyme. The regulatory sequence may control transcription or translation of the encoded enzyme. In another embodiment the genetic modification is to any combination or sub-combination of the above one or more nucleic acid sequence(s) or gene(s), e.g. to T6PP and T6PS. But any combination or sub-combination of the recited nucleic acid sequences (or genes) can be genetically modified to achieve the desired effect. In a specific embodiment the genetic modification is an attenuation (e.g. to T6PS/P, or to T6PS and T6PP). In another embodiment the attenuation is a deletion.

In one embodiment the recombinant cells or organisms of the invention have a genetic modification to a gene or nucleic acid sequence encoding a trehalose-6-phosphate synthase/phosphatase (T6PS/P) in a trehalose biosynthetic pathway. For example, a modified organism of the invention (a Chlorophyte alga *Parachlorella* sp.) was found to have a nucleic acid sequence encoding a T6PS/P of SEQ ID NO: 2. This enzyme shows about 30% sequence identity to T6PP from *Candida albicans*. SEQ ID NO: 2 has a genetic modification (versus the unmodified "wild type" organism) at position 273 where a glutamic acid (E273) in the wild-type was changed to valine in the modified organism, which has increased biomass and/or lipid productivity. The E273 is conserved across species, but in some species the corresponding amino acid residue is an Asp. This residue can also be changed to Val in conserved sequences of other species or changed to another amino acid of similar chemical class in the corresponding position to achieve the high lipid phenotype exhibited by the mutant cells or organisms of the invention. For example, instead of a Val another nonpolar amino acid could be substituted such as, for example, any of Gly, Ala, Leu, Ile, Ser, Asn, Gln, Asp, or Met. Thus, in some embodiments the mutant cells or organisms of the invention have an E273V mutation, or a D273V mutation, or a E273X or D273X mutation, where X is any one of Gly, Ala, Leu, Ile, Ser, Asn, Gln, Asp, or Met.

In various embodiments the encoded the trehalose biosynthetic pathway enzyme has at least 60% or at least 70% or at least 80% or at least 90% or at least 95% or at least 97%, or at least 98% amino acid sequence identity to SEQ ID NO: 2 (trehalose-6-phosphate synthase/phosphatase). In some embodiments the encoded trehalose biosynthetic pathway enzyme has at least 60% or at least 70% or at least 80% or at least 90% or at least 95% or at least 97% or at least 98% sequence identity to an amino acid sequence of at least 50 or at least 60 or at least 70 or at least 100 or at least 300 or at least 400 or at least 500 or at least 600 or at least 700 or at least 750 or at least 800 contiguous amino acids within any of SEQ ID NO: 2 or 4 or 5. In other embodiments the trehalose-6-phosphate synthase/phosphatase can be encoded by a nucleic acid sequence having at least 60% or at least 70% or at least 80% or at least 90% or at least 95% or at least 97% or at least 98% sequence identity to SEQ ID NO: 49.

In one embodiment the genetic modification inserts a stop codon into a coding sequence or regulatory sequence of one or more nucleic acid sequence(s) encoding a trehalose biosynthesis pathway enzyme to make a deletion or disruption of the gene. In one embodiment the genetic modification is a Glu723 to Val (E723V) mutation in the encoded polypeptide of SEQ ID NO: 2 (trehalose-6-phosphate synthase/phosphatase) or in a nucleic acid encoding a polypeptide having at least at least 60% or at least 70% or at least 80% or at least 90% or at least 95% or at least 98% sequence identity to SEQ ID NO: 2. Persons of ordinary skill will understand that a stop mutation or other mutation can be inserted at many other locations or loci within the nucleotide sequence, including in a promoter or other regulatory sequence of the gene, and achieve an attenuation of expression in the gene or in the activity of the encoded polypeptide. Such attenuation or other mutation can also cause a loss of function in the trehalose biosynthetic pathway enzyme and result in the effect of increase lipid productivity.

RNA Binding Domain

RNA binding proteins (RBPs) are involved in RNA metabolism. The function of RBPs is varied and may include transient binding to RNA sequences to assist with splicing, regulation of alternative splicing, a component of hnRNP proteins (heterogeneous nuclear ribonucleoprotein), processing, transport, or localization. Most RBPs have multiple RNA binding domains that include different types of RNA binding motifs that recognize RNA sequences or targets. The RNA recognition motif known as RRM is the most abundant RNA binding domain. In the invention the RNA binding domain can be an RRM from any one or more of the organisms described herein. In one embodiment the RNA binding domain can be an RRM superfamily protein, for example RRM_1. In other embodiments the RNA binding domain can be a protein from the PFAM 0076 family. SEQ ID NO: 1 is the polypeptide sequence of an RNA binding domain with two RNA Recognition Motif (RRM) domains in the N-terminal half of the coding sequence. Orthologs are found in many green algae (Chlorophytes) and plants. The recombinant algal cell of the invention can have a genetic modification to a nucleotide sequence encoding an RNA binding domain that has at least 50% sequence identity or at least 60% sequence identity at least 70% sequence identity or at least 75% or at least 80% or at least 85% or at least 90% or at least 95% or at least 98% amino acid sequence identity with SEQ ID NO: 1, or with the RRM domain of SEQ ID NO: 3, or to a sequence of at least 100 or at least 150 or at least 200 or at least 250 or at least 300 contiguous amino acids within SEQ ID NO: 1 or SEQ ID NO: 3. In various embodiments the RNA binding domain is encoded by a nucleotide sequence having at least 60% sequence identity at least 70% sequence identity or at least 75% or at least 80% or at least 85% or at least 90% or at least 95% or at least 98% amino acid sequence identity with SEQ ID NO: 50.

In some embodiments nucleotide orthologs can encode an RRM domain having at least 70% sequence identity or at least 75% or at least 80% or at least 85% or at least 90% or at least 95% or at least 98% (and, optionally, in any of the embodiments less than 100%) amino acid sequence identity with SEQ ID NO: 1 or SEQ ID NO: 3.

In some embodiments the genetic modification to the nucleic acid sequence is an attenuation or a deletion, but in other embodiments can be an insertion, a point mutation, a disruption, or any of the genetic modifications described herein. In one embodiment the genetic modification inserts a stop codon into a nucleic acid sequence or gene encoding an RNA binding domain described herein, or into a nucleic acid sequence or gene encoding a trehalose biosynthesis enzyme described herein, or into a nucleic acid sequence or gene encoding an SGI1 polypeptide. In one embodiment the genetic modification is a Lys36 to stop mutation (L36Stop or L36*) inserted into a nucleic acid sequence encoding SEQ ID NO: 1 (or, for example, an L15* inserted into a nucleic acid sequence encoding SEQ ID NO: 3), or into a nucleic acid sequence or gene having at least at least 60% or at least 65% or at least 70% or at least 75% or at least 80% or at least 85% or at least 90% or at least 95% or at least 97% or at least 98% (and, optionally, less than 100% in any embodiment) sequence identity to SEQ ID NOs: 1 or 3 or, similarly, to a sequence encoding at least 100 or 150 or 200 or 250 or 300 contiguous amino acids of SEQ ID NOs: 1 or 3. The stop codon or other modification can also be made at many other loci or locations within a nucleic acid sequence or gene or regulatory sequence encoding an RNA binding domain or trehalose biosynthetic pathway enzyme, for example at a promoter, terminator, or other regulatory sequence. Such modifications can achieve an attenuation of expression in the gene or in the activity of the encoded polypeptide. Analogous modifications can be made to the sequence(s) for similar effect. Such attenuation or other mutation can also cause a loss of function in the RNA binding domain, trehalose biosynthetic pathway enzyme, or SGI1 polypeptide, and result in the effect of increase lipid productivity.

SGI1 Polypeptide

As described herein, SGI1 or "Significant Growth Improvement 1" polypeptide is a polypeptide that includes a Response Regulator receiver or "RR" domain (pfam PF00072) and a Myb-like binding domain, referred to herein simply as a "myb" domain (pfam PF00249), where the RR domain is positioned N-terminal to the myb domain or the myb domain is C-terminal to the RR domain. The amino acid sequence of an SGI1 polypeptide that encompasses the RR domain and myb domain can include a stretch of amino acids that occurs between the RR and myb domains that may be poorly conserved or not conserved among SGI1 polypeptides. The amino acid sequence occurring between the RR domain and myb domain may be referred to herein as a linker between the two domains. The linker may be of any length, and in various examples may range in length from one to about 300 amino acids, from 10 to about 200 amino acids, or from 20 to about 150 amino acids in length. The linker region can optionally include a nuclear localization sequence (NLS).

An RR domain within an SGI1 protein can be characterized as pfam PF00072, or as a "signal receiver domain" or simply "receiver domain", and/or can be classified as cd00156 in the conserved domain database (CDD), as COG0784 in the Clusters of Orthologous Groups of proteins database, or as an Interpro "CheY-like superfamily" domain, IPR011006. The RR domain is found in bacterial two-component regulatory systems (like the bacterial chemotaxis two-component system that includes a polypeptide known as CheY), in which it receives a signal from a sensor partner. The RR domain of such systems is often found N-terminal to a DNA binding domain and can include a phosphoacceptor site. Alignment of the RR domains of algal SGI1 attenuation mutant strains can be shown. Sub-sequences of the RR domain from *Parachlorella* sp. WT-1185, *Coccomyxa subellipsoidea, Ostreococcus lucimarinus, Chlamydomonas reinhardtii, Chromochloris zofingiensis, Volvox carteri, Tetraselmis* sp. 105, *Oocystis* sp. WT-4183, and *Micromonas* sp. RCC299 show substantial homology.

A myb domain within an SGI1 protein can be characterized, for example, as pfamPF00249: "Myb-like DNA-binding domain", and/or may be identified as conserved domain TIGR01557 "myb-like DNA-binding domain, SHAQKYF class", or as an Interpro Homeobox-like domain superfamily domain (IPR009057) and/or an Interpro Myb domain (IPROI 7930). Alignment and substantial homology was also shown of the Myb domains of algal SGI1-KO strains. Shown are sub-sequences of the Myb domains from *Parachlorella* sp. WT-1185, *Coccomyxa subellipsoidea, Ostreococcus lucimarinus, Chlamydomonas reinhardtii, Chromochloris zofingiensis, Volvox carteri, Tetraselmis* sp. 105, *Oocystis* sp. WT-4183, and *Micromonas* sp. RCC299.

In addition to having an RR domain N-terminal to a myb domain, an SGI1 protein as provided herein can have a score of 300 or higher, 320 or higher, 340 or higher, 350 or higher, 360 or higher, or 370 or higher with an e-value of less than about 1e-10, 1e-50, 1e-70, or 1e-100, when scanned with a Hidden Markov Model (HMM) designed to score proteins on the basis of how well a protein's amino acid sequence matches the conserved amino acids of a region of SGI1 homologs in algae. The region of SGI1 polypeptides used to develop the HMI is the amino acid sequence that includes (proceeding in the N-terminal to C-terminal direction) the RR domain, the linker, and the myb domain. In a HMM, highly conserved amino acid positions are weighted more heavily than poorly conserved amino acid positions within a compared region of the polypeptides to arrive at the score. Polypeptides having scores of at least about 300, or of 350 or greater, such as for example 370 or greater, when scanned with an HMM model based on protein sequences of algal SGI1 polypeptides that include a single continuous sequence that includes the RR domain, linker, and myb domain developed using include, without limitation, polypeptides of the algal and plant species *Parachlorella* sp. 1185 (SEQ ID NO:8), *Coccomyxa subellipsoidea* (SEQ ID NO:9), *Ostreococcus lucimarinus* (SEQ ID NO:10), *Chlamydomonas reinhardtii* (SEQ ID NO:11), *Chromochloris zofingiensis* (SEQ ID NO: 12), *Volvox carteri* (SEQ ID NO:13), *Tetraselmis* sp. 105 (SEQ ID NOs: 14-16, ocystis sp. (SEQ ID NO:17), *Micromonas* sp. RCC299 (SEQ ID NO:18), and *Micromonas pusilla* (SEQ ID NO:19), *Sphagnum fallax* (SEQ ID NO:20), and *Physcomitrella patens* (SEQ ID NO:21). Additional SGI1 orthologs from additional algae species are identifiable by persons of ordinary skill in the art.

The SGI1 polypeptide encoded by a nucleic acid comprised by the recombinant algal or plant cells of the invention can have at least 50%, at least 55%, at least 60%, at least 65%, at least 70%, at least 75%, at least 80%, at least 85%, at least 90%, at least 95%, at least 96%, at least 97%, at least 98%, or at least 99% (and, optionally, in any embodiment less than 100%) amino acid sequence identity to any SGI1 polypeptide sequence of SEQ ID NOs: 6-21, or to fragments of any of them comprising a consecutive sequence of at least 100, or at least 125, or at least 150, or 200 or more amino acid residues of the entire protein where the polypeptide has an RR domain and a myb domain, and the RR domain can be N-terminal to the myb domain, where the SGI1 polypeptide is a naturally occurring polypeptide or a variant thereof. In various embodiments, the SGI1 polypeptide is from a plant or algal species, i.e., is a naturally-occurring polypeptide of a plant or algal species. A gene or nucleotide sequence encoding an SGI1 polypeptide as provided herein, for example a gene that is disrupted or whose expression is attenuated in a mutant as provided herein, can be a naturally-occurring gene of a plant or algal species that encodes a polypeptide as disclosed herein.

In various embodiments the encoded SGI1 polypeptide can have a (Myb domain) amino acid sub-sequence having at least 75% or at least 80% or at least 85% or at least 90% or at least 95% or at least 98% (and, optionally, in any embodiment less than 100%) sequence identity to a Myb domain sequence of any of SEQ ID NO: 22-30, or to a consecutive sequence of at least 25, or at least 30, or at least 50 or at least 75 amino acid residues of the entire sequence. In various embodiments any of these myb domains can be present in an SGI1 polypeptide with any of the RR domains described herein (e.g. SEQ ID NO: 31-48).

An SGI1 gene that encodes a polypeptide having the sequence of a naturally-occurring algal SGI polypeptide can be a gene having a naturally-occurring gene sequence, or can have a sequence that varies from the sequence of a naturally-occurring gene. In various embodiments, an SGI1 gene that is attenuated, mutated, or disrupted in a mutant photosynthetic organism as disclosed herein can be a gene that is identified through homology searching, for example, using one or more sequences disclosed herein as queries, and/or by HMM scanning, where the HMl is built from amino acid sequences, for example upon multiple alignment of at least six SGI1 polypeptides, where the amino acid sequences include an RR domain and a myb domain, where the RR domain is N-terminal to the myb domain, and where there is a linker sequence between the RR and myb domains that does not belong to either domain.

In some embodiments, an SGI1 polypeptide can be the sequence of an algal or plant SGI1 polypeptide, or is a variant of a naturally-occurring algal or plant SGI1 polypeptide, and can contain a Response Regulator receiver domain as a sub-sequence, for example a sub-sequence of any of SEQ ID NO: 6-21, which can be a consecutive sequence of at least 25, or at least 30, or at least 50 or at least 75 amino acid residues of the entire sequence. The Response Regulator receive domain can contain an amino acid sub-sequence having at least 50%, at least 55%, at least 60%, at least 65%, at least 70%, at least 75%, at least 80%, at least 85%, at least 90%, at least 95%, at least 96%, at least 97%, at least 98%, or at least 99% (and, optionally, in any embodiment less than 100%) sequence identity to any one of the Response Regulator receiver domains of SEQ ID NO: 31-48, or to a consecutive sequence of at least 25, or at least 30, or at least 50 or at least 75 amino acid residues of the entire sequence.

Persons of ordinary skill know how to calculate the percent of "sequence identity" between two sequences. In one embodiment the percent of sequence identity can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268). In one embodiment the search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx can be the BLOSUM62 matrix (Henikoff (1992), Proc. Natl. Acad. Sci. USA 89, 10915-10919). For blastn the scoring matrix can be set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Recombinant Alga

The recombinant mutant algae of the invention demonstrate a significant increase in the production of lipid in the organism, which can be measured (for example) using fatty acid methyl esters (FAME) analysis. The increase in lipid production can be measured as an increase in total FAME produced by the organisms. The recombinant cells of the invention having a genetic modification to a nucleic acid sequence or gene encoding a trehalose biosynthesis pathway enzyme disclosed herein and/or a genetic modification to a nucleic acid sequence encoding an RNA binding domain disclosed herein and, optionally for any of them, a genetic modification to a nucleic acid sequence encoding an SGI1 polypeptide disclosed herein, can exhibit at least 50% or at least 60% or at least 70% or at least 80% or at least 90% or at least 100% greater lipid productivity compared to a corresponding control alga. In other embodiments the increase in lipid productivity can be 15-35% or 15-40% or 25-45% or 15-50% or 25-70% or 25-90% or 25-100% or 25-150% or 25-200%. In one embodiment lipid productivity is measured using total fatty acid methyl ester assay (FAME) known to persons of ordinary skill in the art.

In another embodiment the recombinant cells of the invention having the genetic modification to one or more trehalose biosynthesis pathway enzyme(s) and/or a genetic modification to one or more RNA binding domain(s) and, optionally for any of them, a genetic modification to one or more nucleic acid sequence(s) encoding SGI1 polypeptide, exhibit at least 50% or at least 60% or at least 70% or at least 80% or at least 90% or at least 100% or at least 150% or at least 200% greater biomass productivity versus a control alga. In other embodiments the increase in biomass productivity can be 15-35% or 15-40% or 25-45% or 15-50% or 25-70% or 50-100% or 50-200%. In one embodiment the biomass productivity can be measured as total organic carbon (TOC) using assays known to persons of ordinary skill in the art.

The recombinant cells or organisms of the invention can have the disclosed higher amounts of lipid productivity and/or the higher disclosed amounts of biomass productivity.

Increased Lipid Productivity

Any of the recombinant algal cells disclosed herein can exhibit increased lipid productivity. For example, recombinant algal cells having a genetic modification to one or more nucleic acid sequence(s) encoding a trehalose biosynthetic enzyme (e.g. trehalose-6-phosphate synthase/phosphatase) and/or to one or more nucleic acid sequence(s) encoding an RNA binding domain and, optionally with either or both of them, a genetic modification to one or more nucleic acid sequence(s) encoding SGI1 polypeptide, exhibit higher lipid productivity.

In any embodiment lipid productivity can be measured using the fatty acid methyl ester (FAME) profile, which is known to persons of ordinary skill in the art. In various embodiments any of the recombinant algal cells or organisms of the invention can produce at least 20% more or at least 25% more or at least 30% more or at least 35% more, or at least 50% more or at least 60% more or at least 70% more or at least 80% more or at least 90% more or at least 100% more or at least 125% more or at least 150% more or at least 200% more lipid product than a corresponding (control) cell or organism. In one embodiment the lipid productivity can be measured using the FAME profile of the respective cells or organisms.

An increase in lipid production or lipid productivity can also be measured in grams per square meter per day of the surface of a cultivation vessel (e.g. a flask, photobioreactor, cultivation pond). In various embodiments the recombinant alga of the invention produce at least 3 or at least 4 or at least 5 or at least 6 or at least 7 grams per square meter per day of lipid, which can be measured by the FAME profile. In any of the embodiments the high lipid and/or high biomass productivity phenotype can be obtained under nitrogen deplete conditions, which can be with semi-continuous dilutions (e.g. dilution by about 30% or by about 40% or by about 50%, once per day, and replacing with fresh medium). In one embodiment the lipid product is a fatty acid and/or derivative of a fatty acid. In one embodiment the fatty acids and/or derivatives of fatty acid comprise one or more species of molecules having a carbon chain between C8-C18 or C8-C20 or C8-C22 or C8-C24.

In any of the embodiments the genetic modification to a gene or nucleic acid sequence encoding a RBD domain described herein and/or a gene or nucleic acid sequence encoding a trehalose biosynthetic pathway enzyme described herein, and optionally with either or both of them, a genetic modification to a nucleic acid sequence encoding an SGI1 polypeptide described herein, can result in an attenuation of expression of the respective genes. The genetic modification of any one or more of these genes or nucleic acid sequences can be a knockout, a targeted mutation and gene replacement, a gene replacement, a promoter replacement, a deletion, an insertion, a substitution, a functional deletion, a disruption in a gene or in its regulatory sequence, as well as the introduction of transgenes into the organism.

Biomass Productivity

The recombinant algal cells of the invention can also have higher biomass productivity than a corresponding organism not having a genetic modification to the gene or nucleic acid sequence encoding one or more trehalose biosynthetic pathway enzyme(s) described herein and/or to one or more gene(s) or nucleic acid sequence(s) encoding an RBD domain described herein and, optionally with either or both of them, a genetic modification to a gene or nucleic acid sequence encoding one or more SGI1 polypeptide(s) described herein. Biomass can be measured using the total organic carbon (TOC) analysis, known to persons of ordinary skill in the art. The recombinant cells can have at least 20% higher or at least 25% higher or at least 30% higher or at least 35% higher, or at least 50% higher or at least 60% higher or at least 70% higher or at least 80% higher or at least 90% higher or at least 100% higher or at least 125% higher or at least 150% higher or at least 200% higher biomass productivity than a corresponding (control) cell or organism, which can be measured by total organic carbon analysis. Biomass productivity can be measured as mg/ml of culture per time period (e.g. 1 day or 2 days or 3 days or 4 days or 5 days).

In any of the embodiments the recombinant alga can have the amounts of higher biomass productivity and/or higher lipid productivity stated herein under nitrogen deplete conditions. Thus, in one embodiment the recombinant alga of the invention can have higher total organic carbon production than a corresponding (control) cell or organism, which higher amount can be produced under nitrogen deplete or low nitrogen conditions. In one embodiment biomass productivity can be evaluated by measuring an increase in the total organic carbon of the cells.

Methods of Producing Lipid

The invention also provides methods for producing a composition containing lipids. The methods involve subjecting a culture of algal organisms described herein to at least one treatment of uv radiation (or gamma radiation, or both) to produce a recombinant algal organism described herein, cultivating the recombinant algal organisms in a suitable medium (such as any described herein), and thereby producing a composition containing lipids. Optionally the lipids can be isolated from the recombinant algal organisms. The recombinant alga can be cultivated in any suitable media, such as any of those described herein. The uv treatment can involve, for example, subjecting the culture to uv light (or gamma radiation, or both) for a suitable period of time or under a suitable uv regimen. The recombinant alga can be cultivated for at least 2 days or at least 3 days, or at least 4 days, or at least 5 days, or at least 6 days, or at least 10 days, or at least 20 days, or from 2-10 days, or from 2-20 days or from 2-25 days.

Any of the recombinant cells or organisms of the invention can be cultivated in batch, semi-continuous, or continuous culture. In some embodiments the culture medium can be nutrient replete, or nitrogen deplete (−N). In some embodiment the culturing is under photoautotrophic conditions, and inorganic carbon (e.g., carbon dioxide or carbonate) can be the sole or substantially the sole carbon source in the culture medium. Nitrogen deplete conditions can be achieved by utilizing a culture medium that has no significant source of nitrogen available for cell growth. In various embodiments nitrogen deplete conditions can involve culturing in a buffer having less than 0.5 mM of nitrogen in any available form external to the cell or organism. In some embodiments the cells can be cultured in 0.5 mM or less of KNO3 or urea as a nitrogen source.

The invention also provides methods of producing a biofuel involving cultivating a recombinant algal organism described herein. The methods can also include a step of harvesting a biofuel from a recombinant algal organism of the invention. The recombinant organism can be cultivated in any growth medium, such as any described herein. In one embodiment the recombinant organism is cultivated in a nitrogen deplete medium. In various embodiments the cultivating can occur for a period of at least 3 days or at least 5 days or at least 7 days or at least 15 days or at least 20 days.

FAME and TOC Analysis Methods

The lipid productivity of the cells or organisms can be measured by any method accepted in the art, for example as an increase or decrease in fatty acid methyl esters (FAME) comprised in the cell, i.e. analysis of the cell or organism's FAME profile. In some embodiments any of the recombinant algal cells or organisms of the invention can have higher biomass productivity versus corresponding control cells or organisms. In some embodiments any of the recombinant algal cells or organisms of the invention can have both higher lipid productivity and higher biomass productivity compared to a corresponding control cell or organism. Biomass productivity can be measured by any methods accepted in the art, for example by measuring the total organic carbon (TOC) content of a cell. Embodiments of both methods are provided in the Examples.

"FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. In some embodiments lipid productivity is assessed as FAME productivity in milligrams per liter (mg/L), and for algae, may be reported as grams per square meter per day (g/m2/day). In semi-continuous assays, mg/L values are converted to g/m2/day by taking into account the area of incident irradiance (the SCPA flask rack aperture of 1½ inches×3⅜", or 0.003145 m2) and the volume of the culture (550 ml). To obtain productivity values in g/m2/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise. The term "fatty acid product" includes free fatty acids, mono-di, or tri-glycerides, fatty aldehydes, fatty alcohols, fatty acid esters (including, but not limited to, wax esters); and hydrocarbons, including, but not limited to, alkanes and alkenes).

EXAMPLES

Example 1—Production of SGI1 Mutants

The production of algal strains containing a genetic modification in a nucleic acid sequence encoding an SGI1 polypeptide is known in the art and is detailed in US 2018/0186842, published Jul. 5, 2018, and which is hereby incorporated by reference in its entirety, including all tables, figures, and claims.

Briefly, wild-type *Parachlorella* sp. (a Chlorophyte, or green algae species) obtained from marine environments were mutagenized with uv radiation in a STRATALINKER® 2400 uv crosslinker (AGILENT TECHNOLOGIES® Inc., Santa Clara, CA) and selected based on low chlorophyll fluorescence after low light acclimation.

The cells were grown to mid-log phase and then diluted to $1\times10_6$ (1e6) cells/mL with a nutrient replete growth medium. The cell suspensions were transferred to a Petri dish and placed within a STRATALINKER® 2400 UV crosslinker (AGILENT TECHNOLOGIES® Inc. Santa Clara, CA) with the plate lid removed. UV irradiation was carried out with 10,000, 25,000, and 50,000 µJ/cm2. After irradiation, cell suspensions were pipetted into a shake flask wrapped in foil to prevent light exposure for twenty-four hours during recovery. Following mutagenesis and recovery cells from pale colored colonies were selected and allowed to grow from between one and five days in low (100 µmol photons m-2 sec-I) light, after which they were sorted by flow cytometry to select cells having low chlorophyll fluorescence.

Further primary screening of antenna-reduced lines isolated through flow cytometry was conducted through the selection of pale green or yellow colonies visually after sorted cells were plated. In order to screen putative antenna-reduced lines from other reduced pigment mutants and false positives, selected colonies were subjected to a medium-throughput secondary cultivation screen to acclimate the isolates to low light conditions prior to photo-physiological measurements. Chlorophyll fluorescence was monitored during low light acclimation to select colonies that retained the reduced chlorophyll fluorescence characteristic of the high light acclimated state. Clones that were selected demonstrated only small increases in chlorophyll (relative to wild type cells) when transferred from high to low light.

Semi-continuous culture assays in constant high light (approximately 1,700 µmol photons m-2 sec-1) using 165 ml cultures in 75 cm2 tissue culture flasks were performed to identify strains having increased productivity (increased rate of biomass production, measured as TOC accumulation) with respect to the wild type progenitor. Two 75 cm2 flasks were inoculated with seed culture of a given mutant strain with CO2-enriched air (1% CO2) bubbled through the cultures. Samples for TOC analysis were taken from the culture removed for the dilution. Isolates were identified having increased productivity.

Genome sequencing and genotyping of resultant strains revealed mutations including distinct SNPs. The effect of higher biomass productivity was found to be related to an SNP in the sequence of SGI1 polypeptide at amino acid 250, which was changed from Leu to Pro (i.e. a Leu250Pro SNP). The gene encoding SGI1 polypeptide in *Parachlorella* sp. has the nucleotide sequence of SEQ ID NO: 6, and the coding sequence of SEQ ID NO: 7, which encodes the amino acid sequence of SEQ ID NO: 8. The SNP was found to result in a Leu250Pro mutation in SGI1 polypeptide. This mutation was recapitulated in a wild-type Cas9 editor strain of *Parachlorella* sp. to produce "SGI1 mutants," and these cells were then used in subsequent procedures.

Example 2—Mutagenesis

The SGI1 mutants from Example 1 were irradiated with uv light in a STRATALINKER® 2400 uv crosslinker (Agilent Technologies®, Santa Clara, CA). Irradiation was done in four dosages with duplicates per dosage. Cells were diluted to a concentration of $5\times10^6$ (5e6) cells/ml and irradiated on agar plates with approximately $5\times10^7$ (5e7) cells total per petri dish. Irradiation dosages included 16 seconds at 27,000 uJ/cm$^2$, 12 seconds at 20,000×uJ/cm$^2$, 8 seconds at 13,000 uJ/cm$^2$, and 6 seconds at 10,000 uJ/cm$^2$.

Example 3—Growth and Bodipy Staining

Mutagenized cells were then grown to a suitable concentration as measured by OD730 of 3.0 in flasks containing PM074 media. Cells were then transferred to media containing PM123 media (aquarium salts, PROLINE A®, and PROLINE (Pentair Aquatic Eco-Systems®, Inc.)) and a final OD730 of 0.1 (PROLINE A® and PROLINE B® together include 8.8 mM NaNO3, 0.361 mM NaH2PO4·H2O, 10× F/2 Trace metals, and 10× F/2 Vitamins (Guillard (1975) "Culture of phytoplankton for feeding marine invertebrates," eds. Smith, W. L. and Chanley, M. H., Plenum Presse, New York, pp. 26-60). After growing to suitable concentration (OD730 of 2.8) cells were spun down in a centrifuge and re-suspended in flasks containing nitrogen-free PM67 media (aquarium salts, K2HPO4, vitamin mix, chelated trace metal mix). Cells were placed in a glass tank flask and a final concentration of cells of OD730 of 1.4 was reached and cells were placed under a constant stream of 1% CO2 in air.

After 48 hours of batch growth in nitrogen deplete media (i.e. the culture medium had no nitrogen source) an aliquot of cells was removed and subjected to staining with the lipid-specific dye BODIPY (boron-dipyrromethene). Mutant cells with the highest level of BODIPY staining were enriched by fluorescence activated cell sorting (FACS). Enriched cell populations were grown and re-inoculated and allowed to grow as above, and again subjected BODIPY staining and FACS at 48 h under nitrogen deplete (−N) batch growth. This iterative process was repeated for a total of five rounds of sorting, with the final sort resulting in single cell isolates.

Example 4—Fame and Toc Analysis

Figure 1B:
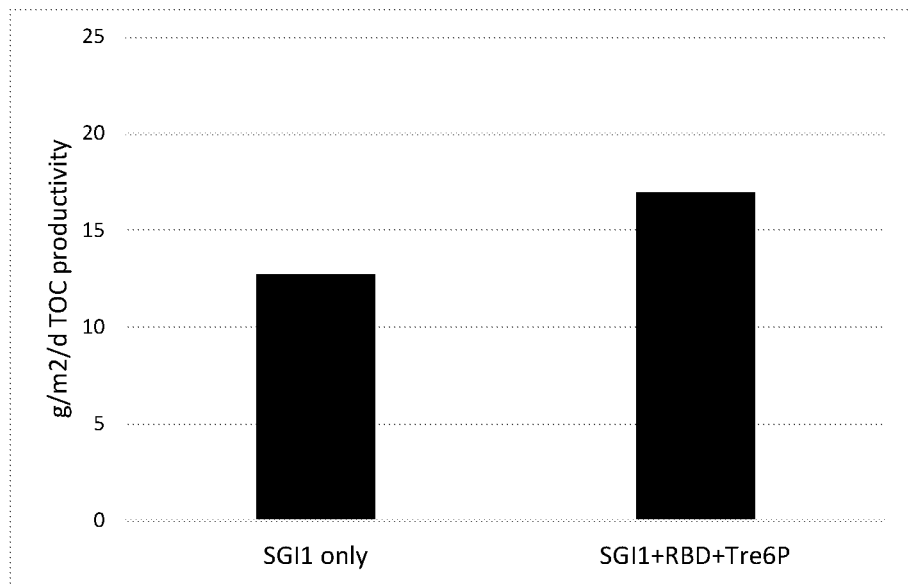
FIG. 1B shows aerial lipid productivity (as TOC) as the mean of the first two days in nitrogen deplete conditions.

Once rendered axenic from bacterial contamination by treatment of cultures with streptomycin at 0.6 mg/ml, isolates having the SGI1 mutation plus the RNA binding domain (RBD) and trehalose-6-phosphate synthase/phosphatase (Tre6P) attenuations were cultivated under nitrogen-deplete growth conditions and compared to the parental SGI1-KO only mutant strain for nitrogen-deplete batch lipid and biomass productivity. The FAME and TOC measurements show the amount of fixed carbon that is partitioned to lipids and nitrogen-deplete lipid productivity. FIG. 1a shows that the isolates exhibited an increase in FAME/TOC ratio (an indicator of how much fixed carbon is partitioned to lipids) compared to the SGI1-KO only mutants, and FIG. 1b shows higher TOC productivity. Thus, mutants having the SGI1+RBD+Tre6P attenuations were isolated and had improved lipid productivity versus mutants having the SGI1-KO alone.

Total organic carbon (TOC) of the algal culture samples was determined by diluting 2 mL of cell culture to a total volume of 20 mL with DI water. Three injections per measurement were injected into a TOC high sensitivity analyzer for determination of Total Carbon (TC) and Total Inorganic Carbon (TIC). The combustion furnace was set to 720° C., and TOC was determined by subtracting TIC from TC. The 4-point calibration range was from 2 ppm to 200 ppm corresponding to 20-2000 ppm for non-diluted cultures with a correlation coefficient of $r^2$ (r squared) greater than 0.999.

To determine lipid content, FAME analysis was performed on 2 mL samples that were dried using an evaporator. To the dried pellets the following was added: 500 μL of 500 mM KOH in methanol, 200 μL of tetrahydrofuran containing 0.05% butylated hydroxyl toluene, 40 μL of a 2 mg/ml C11:0 free fatty acid/C13:0 triglyceride/C23:0 fatty acid methyl ester internal standard mix and 500 μL of glass beads (425-600 um diameter). The vials were capped with open top PTFE septa-lined caps and placed in a tissue homogenizer at 1.65 krpm for 7.5 minutes. The samples were then heated at 80° C. for five minutes and allowed to cool. For derivatization, 500 μL of 10% boron trifluoride in methanol was added to the samples prior to heating at 80° C. for 30 minutes. The tubes were allowed to cool prior to adding 2 mL of heptane and 500 μL of 5 M NaCl. The samples were then vortexed for five minutes at 2 krpm and finally centrifuged for three minutes at 1 krpm. The heptane layer was sampled using an autosampler. Quantitation used the 80 μg of C23:0 FAME internal standard.

Example 5—Genotyping of Mutants

Genomic DNA was isolated from these mutants and from the SGII only mutant parental strain (STR0012) and the wild-type corresponding control strain (STR00I0). Isolated gDNA was sequenced using Next Generation sequencing on an Illumina® instrument ILLUMINA®, Inc., San Diego, CA). Sequence reads were processed, mapped to the wild type reference genome and analyzed by a small variants caller algorithm (derived from the FREEBAYES™ polymorphism detection software, which is a Bayesian genetic variant detector designed to find small polymorphisms, specifically SNPs, indels (insertions and deletions), MNPs (multi-nucleotide polymorphisms), and complex events (composite insertion and substitution events) smaller than the length of a short-read sequencing alignment. Analysis of small nucleotide polymorphisms (SNPs) and small insertions/deletions (InDels) revealed the sequenced strains to be genetic siblings of each other having a core set of 28 polymorphisms shared across the strains.

The SNPs shown in Table 1 revealed the candidate genes where the underlying causative mutations causing the high lipid phenotype might occur. Fifteen SNPs were either intergenic or present in introns of a gene; assessment of transcriptomics and RNA sequence data from the new mutants indicated that these SNPs had no impact on neighboring gene expression or intron splicing.

But thirteen of the 28 SNPs were prioritized for genetic recapitulation based on the deduced change in coding sequence of the encoded gene. One of the 13 sibling high lipid mutants, named Strain 600 (STR0600), was selected for all further experiments. The 13 mutants were identified as noted in Table 1.

TABLE 1

| | | | | |
|---|---|---|---|---|
| Downstream gene variant | Haloacid dehalogenase-like hydrolase domain-containing protein 2 | SNP | G | A |
| Downstream gene variant | Conserved predicted protein | MNP | GG | AA |
| Downstream gene variant | Glucuronoxylan 4-O-methyltransferase 1 | SNP | C | T |
| Intron variant | SNF2 domain-containing protein/helicase domain-containing protein/F-box family protein isoform 3 | SNP | T | C |

TABLE 1-continued

| | | | | |
|---|---|---|---|---|
| Intron variant | Amino acid transmembrane transporter | SNP | C | T |
| Intron variant | AarF domain-containing kinase | SNP | G | A |
| Upstream gene variant | Conserved predicted protein | SNP | T | A |
| Upstream gene variant | Conserved predicted protein | Deletion | CTCATCAC | CTCAC |
| Upstream gene variant | Zinc finger ccch domain-containing protein 29 | SNP | G | A |
| Upstream gene variant | D-amino acid aminotransferase | SNP | T | A |
| Intron variant | Exostosin family protein isoform 1 | SNP | C | A |
| Upstream gene variant | Conserved predicted protein | SNP | T | G |
| Intron variant | Exostosin family protein isoform 1 | Insertion | ATT | ATTT |

Example 6—Genetic Recapitulation

To determine the mutation(s) that are the cause of the high lipid phenotype, knockouts, and/or exact recapitulation of SNPs observed in STR0600 were re-created in a markerless Cas9/Cre expression strain containing a SGI1 knockout (SGI1-KO). In addition, a variant of STR00600 in which Cas9/Cre expression cassettes were integrated in a markerless fashion was generated in order to examine the effect of reverting SNPs back to wild type. Thus individual SNPs could be evaluated to determine which were necessary to produce the high lipid phenotype, and whether the phenotype might have a complex genetic underpinning where one SNP is not sufficient to recapitulate the phenotype.

All strains generated were tested for the high lipid and/or high biomass productivity phenotype under nitrogen deplete (−N) batch conditions in a simplified assay conducted in T25 flasks containing PM153 buffer for an OD730 of 0.1. PM153 is a nutrient replete medium that is based on PM074 but includes urea instead of nitrate as the nitrogen source. It is made by adding 1.3 ml Proline® F/2 Algae Feed Part A (Pentair Aquatic Eco-Systems) and 1.3 ml 'Solution C' to a final volume of 1 liter of a solution of aquarium salts (17.5 g/L), and then adding 4 ml if 1.1 M filter-sterilized urea. Solution C is 38.75 g/L NaH2PO4 H2O, 758 mg/L thiamine HCl, 3.88 mg/L vitamin Bl2, and 3.84 mg/L biotin.

PM074 is a nutrient replete medium. While any suitable algal growth medium can be employed in the invention, PM074 is made by adding 1.3 ml Proline® F/2 Algae Feed Part A (Pentair Aquatic Eco-Systems, Inc., Apopka, FL) and 1.3 ml Proline® F/2 Algae Feed Part B to a final volume of 1 liter of a solution of Instant Ocean salts (35 g/L) (Pentair Aquatic Eco-Systems Inc., Apopka, FL). Proline A® and Proline B® together include 8.8 mM NaNO3, 0.361 mM NaH2PO4·H2O, 10× F/2 Trace metals, and 10× F/2 Vitamins (Guillard (1975) *Culture of phytoplankton for feeding marine invertebrates* in "Culture of Marine Invertebrate Animals." (eds: Smith W. L. and Chanley M. H.) Plenum Press, New York, USA. pp 26-60).

For biomass and lipid productivities, strains were pre-acclimated in a 14:10 diel 1% CO2 incubator and scaled to 1000 ml in PM153 media. Cultures were normalized to about 350 mg/l TOC, which is 60% of the empirically determined steady state standing biomass density for a daily 40% dilution rate. The total culture volume was 420 ml in a 500 ml square polycarbonate bottle. Flasks were kept at 30° C. using a water bath, stirred via magnetic bar and 1% CO2 bubbled at 300 ml/min. Light was supplied by LED panels through a 0.0875 m2 aperture and programmed to a 14:10 diel cycle. For nitrogen replete biomass productivity measurements, samples were taken for OD730, Flow Cytometry, FAME and TOC analysis at dusk and the cultures diluted back 40% with PM153 in a semi-continuous manner for 8-9 days. Following the nitrogen replete semi-continuous mode, the flask was removed at dusk, pelleted and the supernatant discarded. The strains were resuspended in PM152 (nitrogen-deplete) media and normalized to about 250 mg/l TOC as empirically determined to give maximal lipid productivity. The cultures were placed back into new 500 ml bottles at 420 ml volume as above. The cultures were grown in batch mode to test lipid productivity during nitrogen deplete induction with sampling again at dusk.

Figure 2A:
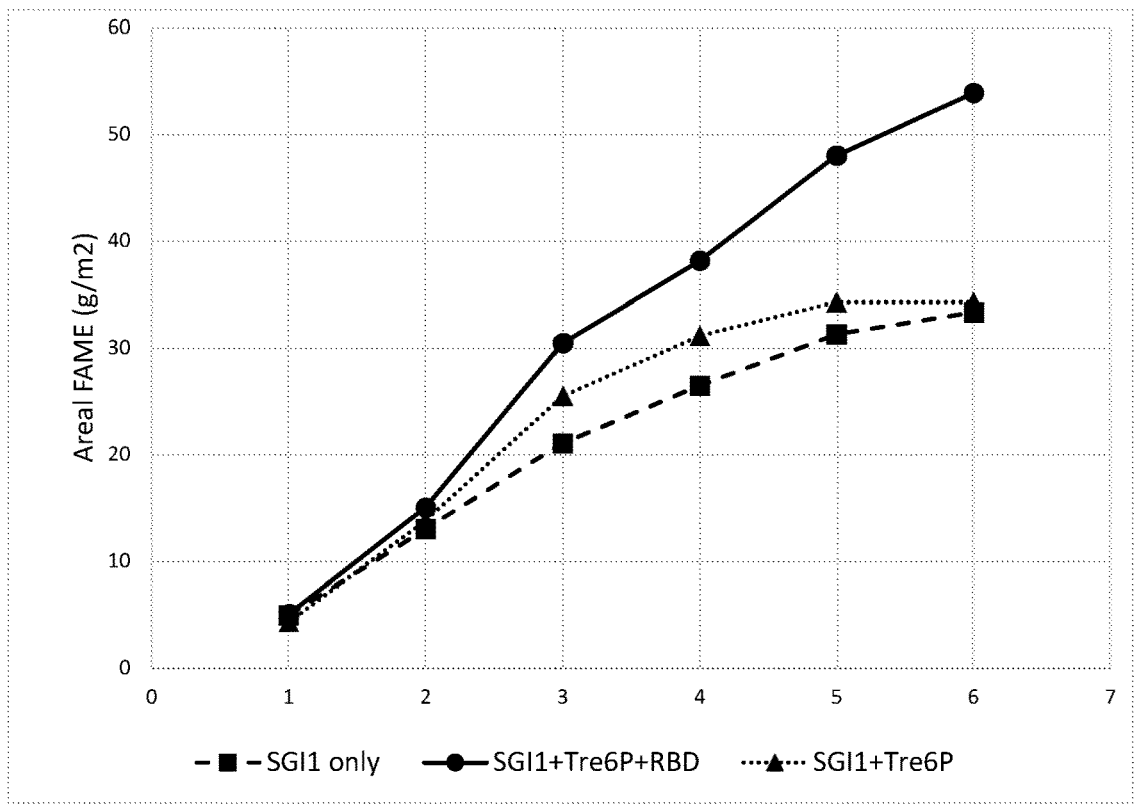
FIGS. 2A-2C, in FIG. 2A the Tre6P recapitulation (SGI1+Tre6P) showed increased areal FAME productivity over the SGI1-KO strain (SGI1 "knock out" only) in the early stages of nitrogen starvation. By Day 6 levels fall to the same level as the SGI1-KO strain.
Figure 2B:
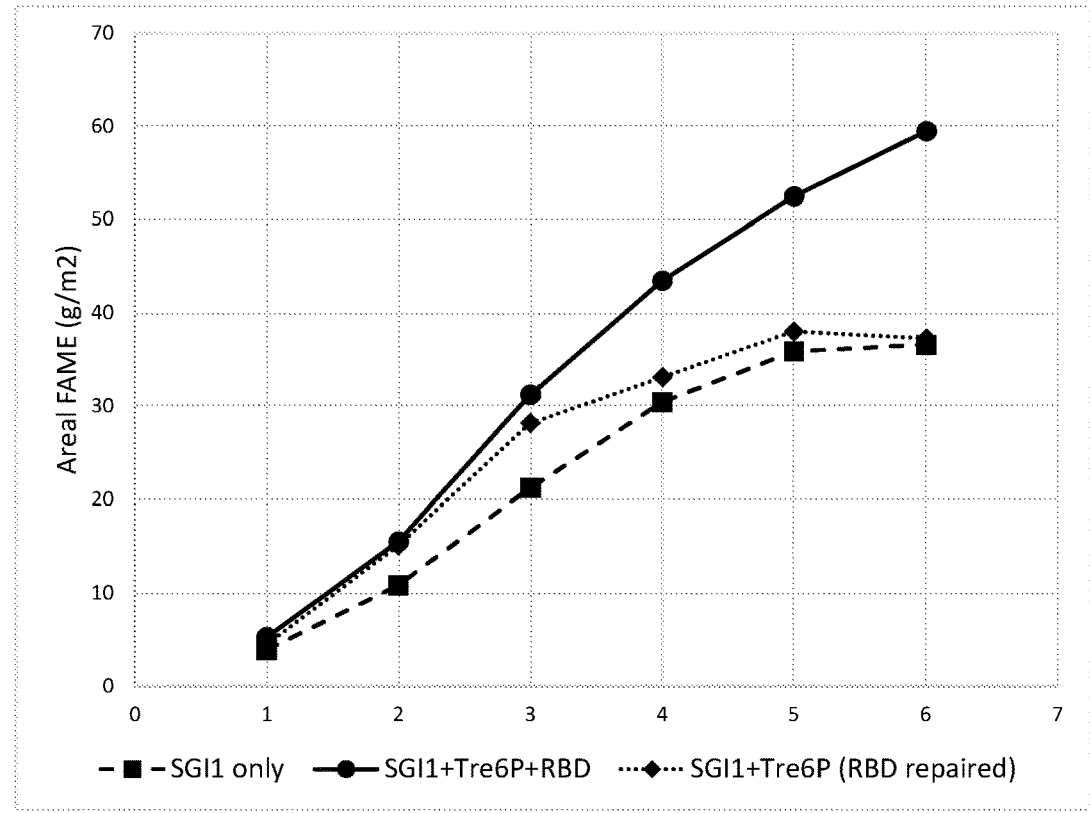
Figure 2C:
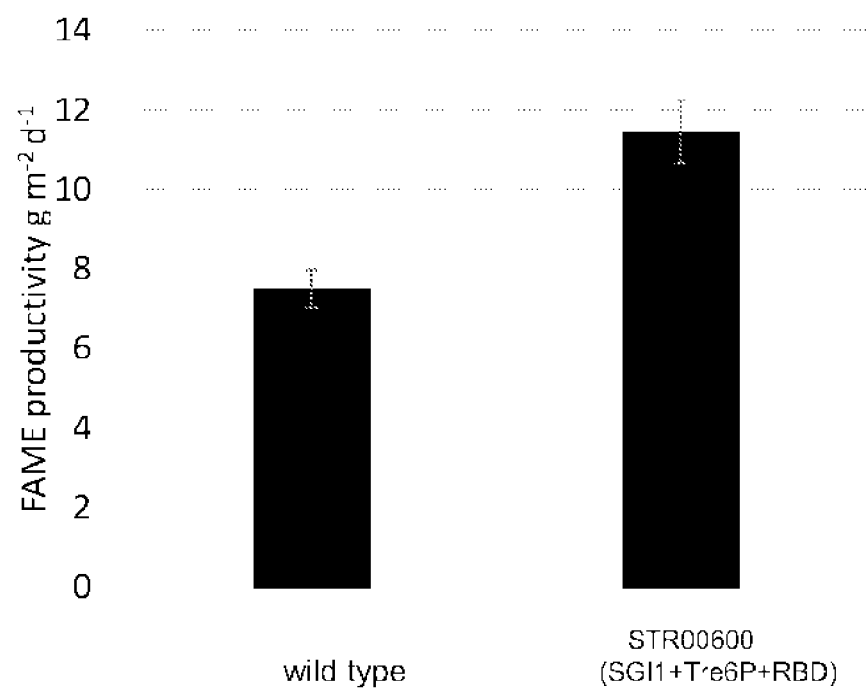
Figure 3A:
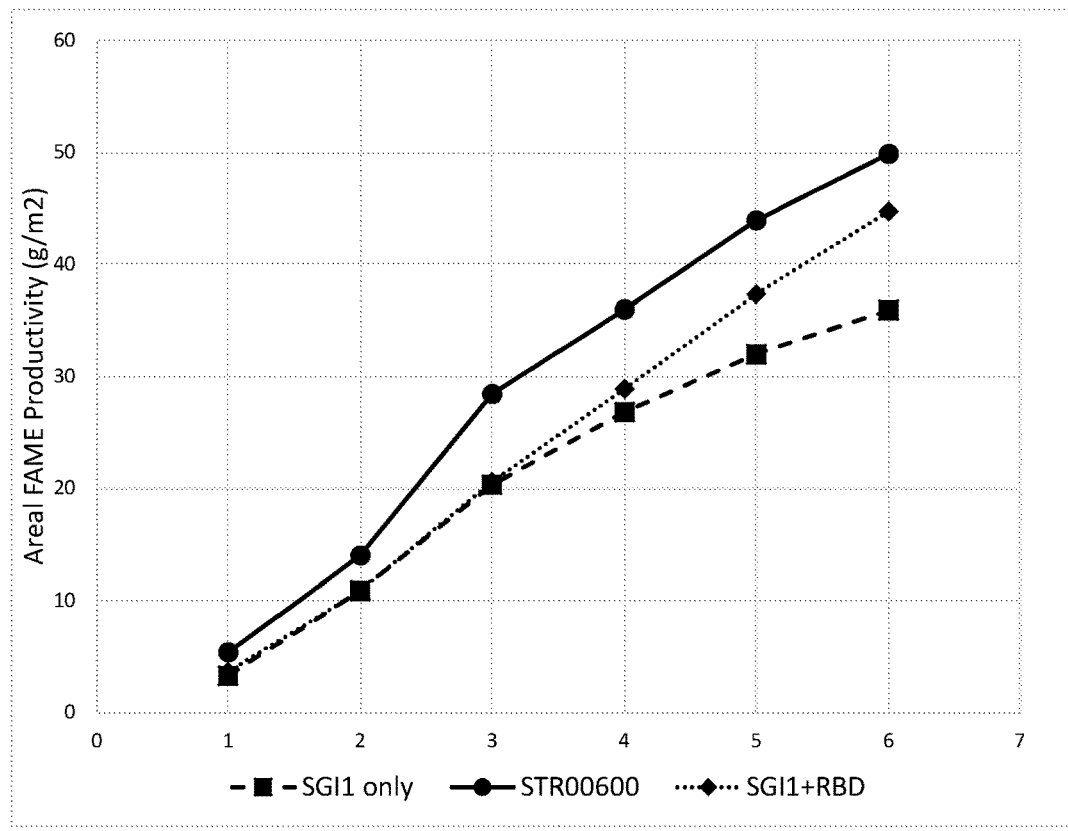
FIGS. 3A-3B shows late improvements in lipid productivity driven by the RBD deletion.
Figure 3B:
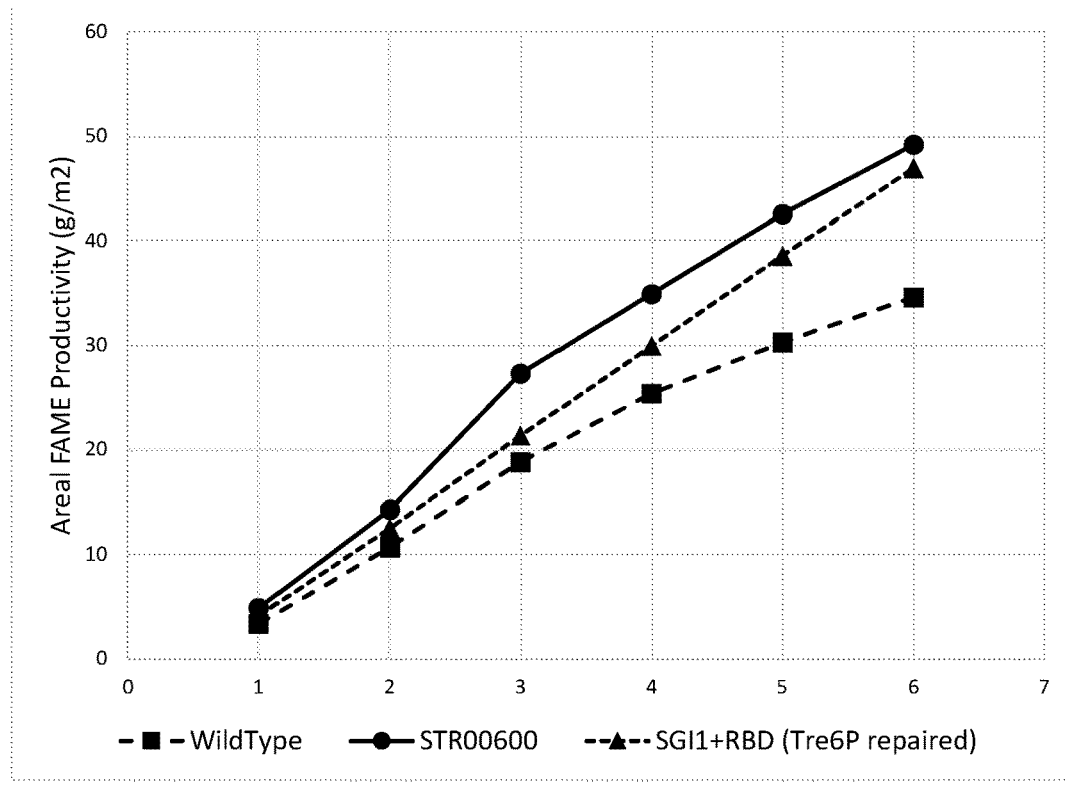
Figure 5A:
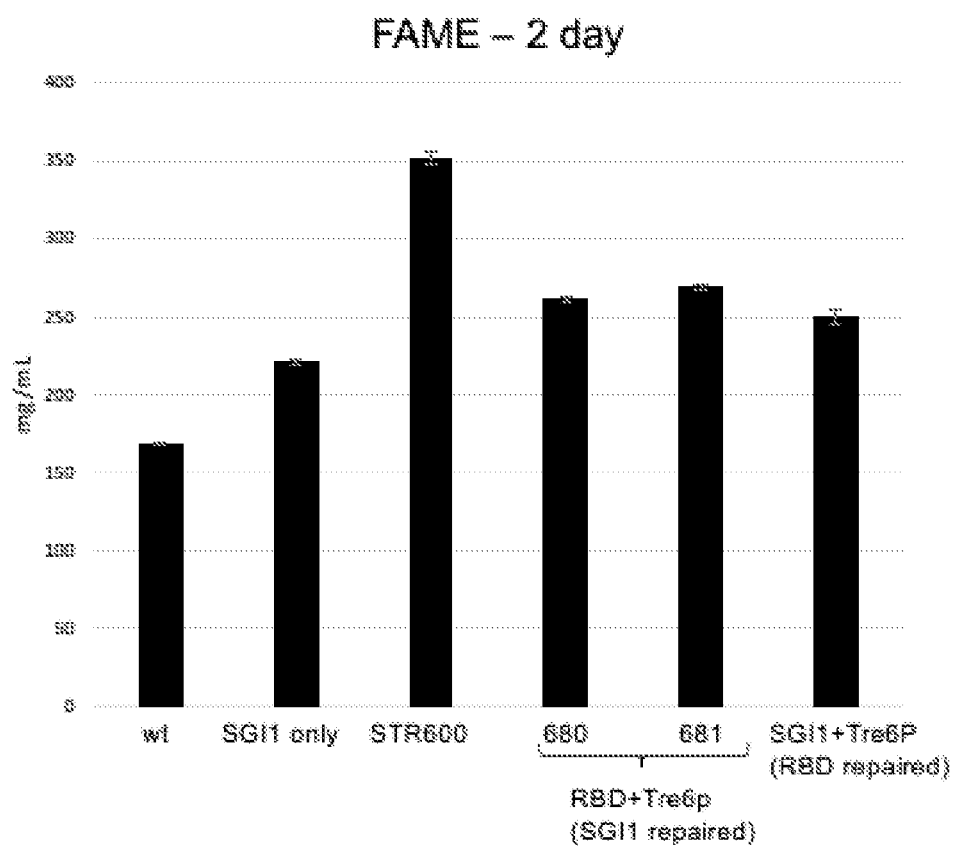
FIGS. 5A-5B shows mutation repair strains versus SGI1-only as background strain.
Figure 5B:
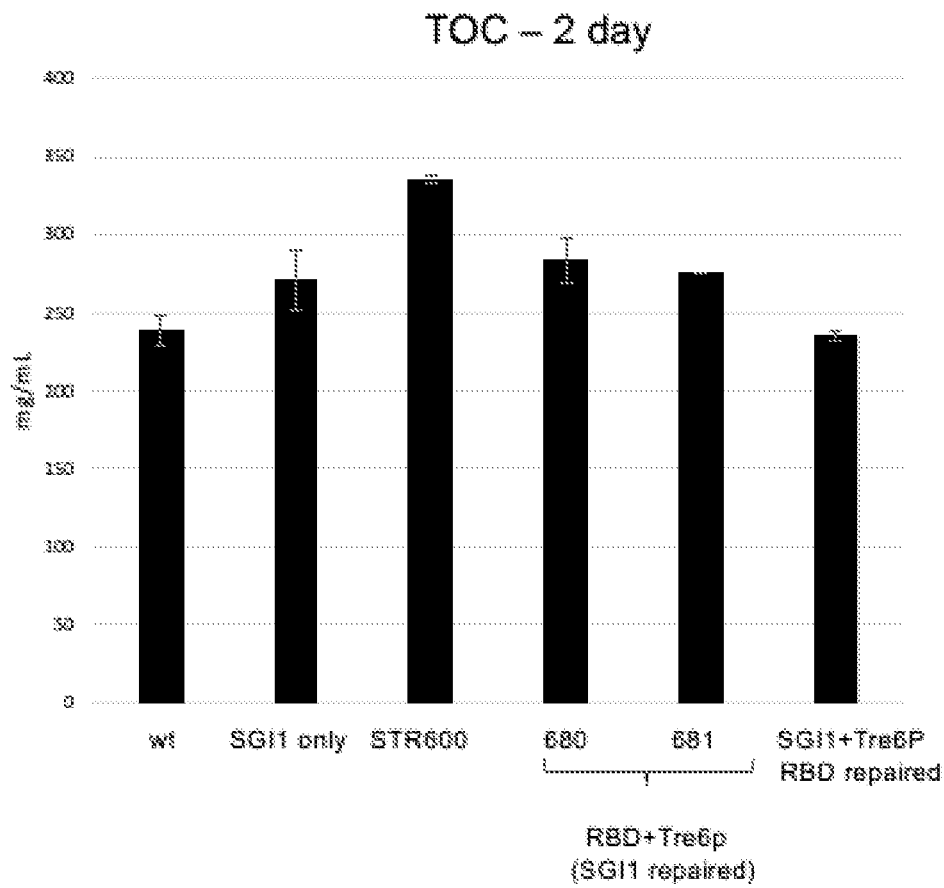

Two mutations were identified as giving rise to the high lipid phenotype. The mutations identified were a Glu723Val (E723V) mutation in the encoded Tre6P enzyme (SEQ ID NO: 2), and a Lys36Stop (Lys36*) mutation in the encoded RBD (SEQ ID NO: 1). It was observed that 1) introducing the Tre6P SNP into a SGI1-KO mutant to produce a mutant having the SGI1-KO+Tre6P attenuation provided a strain with increased lipid productivity, as shown in FIG. 2a; 2) repair of the RBD attenuation to wild-type in Strain 600 (SGI1+RBD+Tre6P) to produce a strain having the SGI1+Tre6P attenuation, resulted in a strain having a decreased lipid productivity (FIG. 2b); 3) introducing the RBD attenuation into the SGI1-only mutant strain resulted in increased lipid productivity under nitrogen deplete batch growth, as shown in FIG. 3a; 4) Tre6P repair in the SGI1+Tre6P+RBD (STR0600) strain resulted in a reduced −N batch lipid productivity, as shown in FIG. 3b, but was still higher than the wild type strain (STR0010) and reached almost as high as the STR0600 having all three modifications; 5) repair of the SGI1 mutation in STR00600 resulted in a reduced −N (nitrogen deplete) batch lipid productivity and TOC productivity, as shown in FIGS. 5a and 5b. FIG. 2c also shows significantly higher FAME productivity for the SGI1+ Tre6P+RBD mutant strain (STR0600) under batch conditions.

Figure 4A:
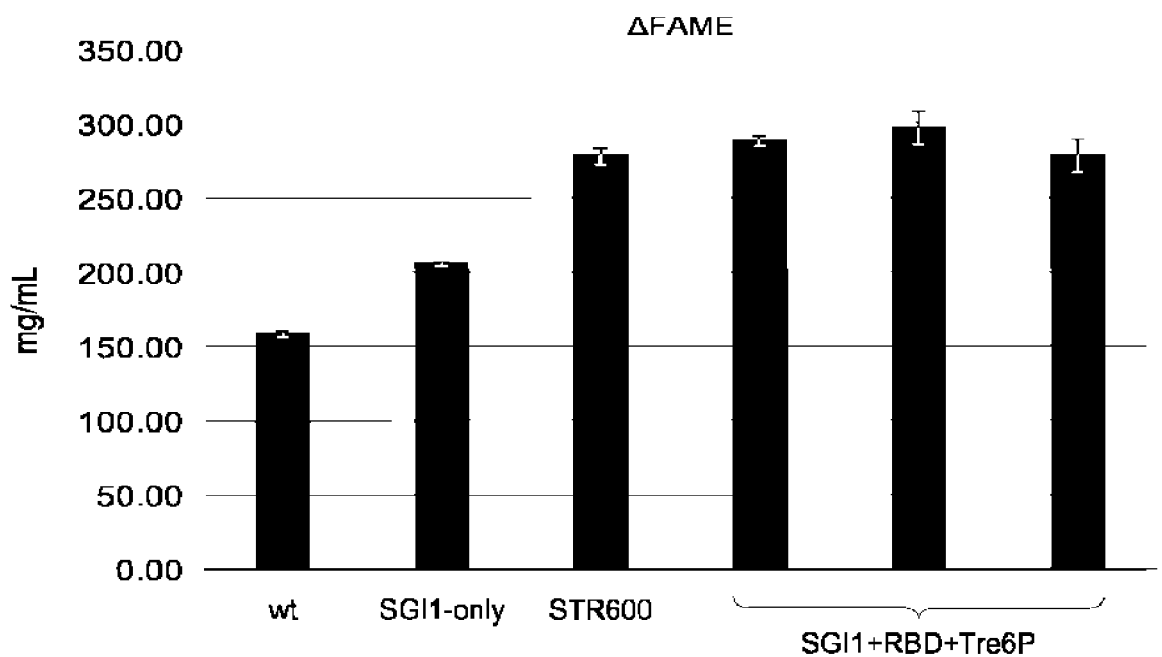
FIGS. 4A-4B shows assay data for RBD and Tre6P mutations stacked into an SGI1 only strain. The data represent the average and standard deviation for biological duplicate cultures, where FAME and TOC productivities are determined over the first two days under nitrogen deplete conditions.
Figure 4B:
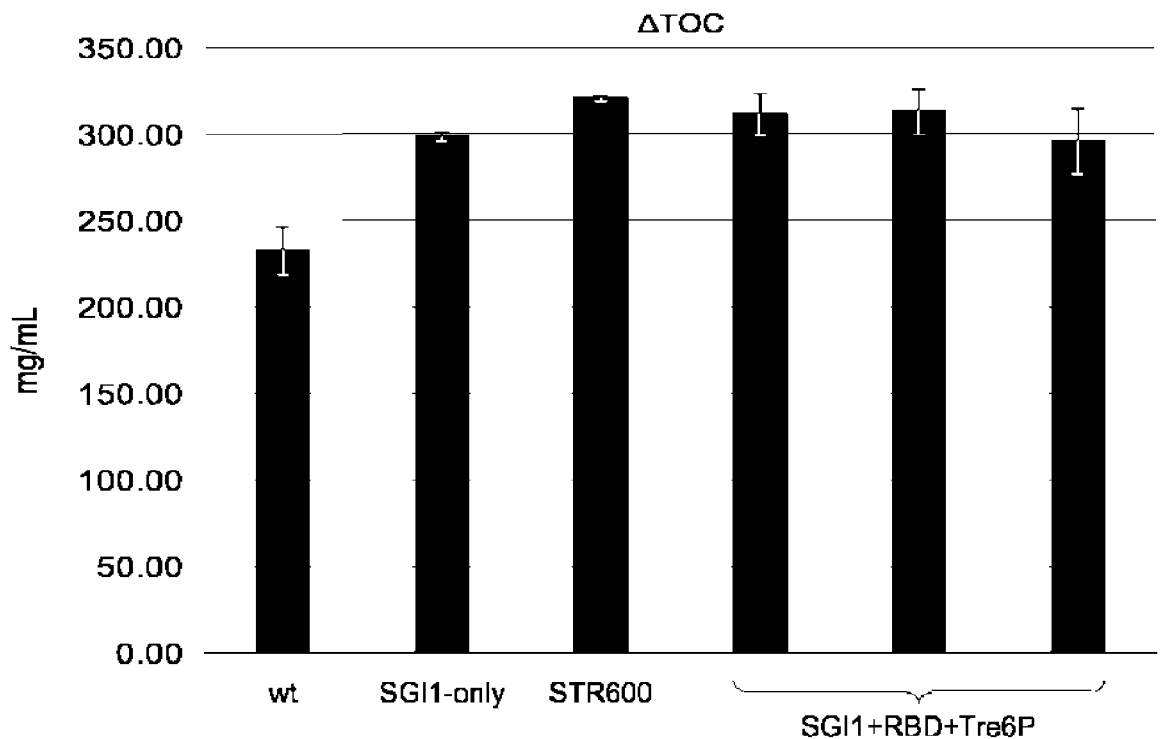

As noted, the strain designated STR0600 has all three genetic modifications, 1) the SGI1 mutation, 2) the RBD mutation, and 3) Tre6P mutations. FIGS. 4a-4b show that the SGI1-only mutant (STR012) exhibited an approximately 30% higher FAME production and TOC production versus the wild-type. FIGS. 4a-4b also show three independent lines that were generated having the SGI1 mutation as well as the RBD and Tre6P attenuations—all three lines showed a lipid productivity and TOC equivalent to STR0600. FIGS. 5a and 5b show two strains (680, 681) having only the RBD and Tre6P mutations, and one having only the SGI1 and Tre6P mutations—these strains showed greater FAME accumulation at Day 2 (55%, 59%, and 49% for FAME, respectively) than wild-type (STR010). The strains also showed 19%, 15% higher TOC accumulation than wild-type for 2-day TOC accumulation). RBD repair resulted in a drop in lipid productivity to a level below the STR0600 and similar to that of the 680 and 681 (RBD+Tre6p) strains.

Therefore, it was shown that the RBD and Tre6P mutations can be "stacked" in an SGI1 mutation strain to recapitulate the high lipid phenotype of STR0600, and the mutations giving rise to the phenotype resolved.

Example 7—Mutation Identification

The genomes of the organisms were sequenced and amino acid sequences of the encoded RBD and Tre6P polypeptides were determined to be SEQ ID NO: 1 and SEQ ID NO: 2, respectively, from the *Parachlorella* sp. Analyses of functional annotation and orthologs present in other organisms revealed that the gene encoding the RNA binding domain protein (SEQ ID NO: 1) has two RNA Recognition Motif (RRM) domains in the N-terminal half of the coding sequence. BLAST searching revealed that orthologs are broadly distributed in green algae with about 50% sequence identity and about 75% positive amino acid identity within amino acid chemical classes (aliphatic, hydroxyl or sulfur-containing, cyclic, aromatic, basic, and acidic and their amide) with the RRM domain observed in maize. The Musashi-like proteins of this class are well characterized RBD proteins (J Cell Sci. 2002 Apr. 1; 115(Pt 7):1355-9), and the function of this class of proteins is believed to be the targeted regulation of translation of mRNAs, and the encoded RNA binding domains in the present case may therefore have similar or the same function.

Figure 6:
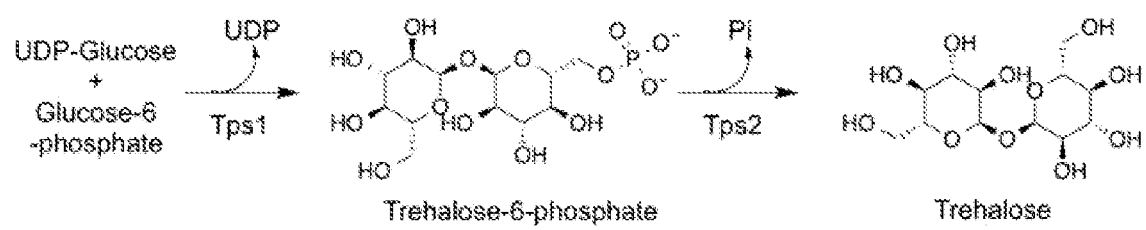
FIG. 6 provides a graphical illustration of a biosynthetic pathway from the conversion of glucose-6-phosphate and UDP-glucose into trehalose-6-phosphate and then trehalose.

SEQ ID NO: 2 is the sequence of a trehalose-6-phosphate synthase/phosphatase from *Parachlorella* sp. that could catalyze reactions analogous to both the Tsp1 and Tsp2 reactions of *Candida albicans*, presented as an example in FIG. 6. The Glu723 was found to be well conserved in homologues as Glu or, in some cases, aspartic acid. Nevertheless, in the recombinant alga of the invention it was found to have mutated to valine and was found to be an E723V mutation.

Although the invention has been described with reference to the above examples, it will be understood that modifications and variations are encompassed within the spirit and scope of the invention. Accordingly, the invention is limited only by the following claims.

What is claimed:

1. A recombinant Chlorophyte algal cell comprising: a disruption in a nucleic acid sequence encoding an RNA binding domain having at least 90% sequence identity to SEQ ID NO: 1; wherein the recombinant Chlorophyte alga exhibits increased lipid productivity versus a corresponding control algal cell not having the genetic modification.

2. The recombinant Chlorophyte alga of claim 1, wherein the nucleic acid sequence encoding the RNA binding domain has at least 95% sequence identity to SEQ ID NO: 1.

3. The recombinant Chlorophyte alga of claim 2, further comprising a disruption in a nucleic acid sequence encoding an SGII polypeptide having at least 90% sequence identity to SEQ ID NO: 8.

4. The recombinant Chlorophyte alga of claim 1, further comprising a Leu250Pro mutation in a nucleic acid sequence encoding an SGII polypeptide.

5. The recombinant Chlorophyte alga of claim 3 further comprising a Leu250Pro mutation in a nucleic acid sequence encoding an SGII polypeptide.

6. The recombinant Chlorophyte algal of claim 1, wherein the nucleic acid sequence encoding the RNA binding domain has at least 90% sequence identity to SEQ ID NO: 3.

7. The recombinant Chlorophyte alga of claim 1, wherein the alga is of the Class Trebouxiophyceae.

8. The recombinant Chlorophyte alga of claim 1, wherein the recombinant algal cell is an alga of the genus *Parachlorella*.

9. The recombinant Chlorophyte alga of claim 3 wherein the recombinant alga has at least 5 grams per square meter per day of lipid production.

10. The recombinant Chlorophyte alga of claim 3, wherein the recombinant alga has higher biomass productivity per unit time.

11. The recombinant Chlorophyte alga of claim 10, wherein the recombinant alga has higher biomass productivity when cultivated under nitrogen deplete conditions.

12. The recombinant Chlorophyte alga of claim 3 wherein the recombinant alga has higher total organic carbon production when cultivated under nitrogen deplete conditions.

13. The recombinant Chlorophyte alga of claim 3 wherein the recombinant alga is a Chlorophyte alga of a genus selected from the group consisting of:

*Chlorella, Parachlorella, Picochlorum, Tetraselmis,* and *Oocystis*.

14. The recombinant Chlorophyte alga of claim 13, wherein the recombinant alga is an alga of the genus *Parachlorella*.

15. The recombinant Chlorophyte alga of claim 1 further comprising a disruption in a nucleic acid sequence encoding an SGII polypeptide having at least 90% sequence identity to SEQ ID NO: 8.

* * * * *

SEQUENCE LISTING

```
<160> NUMBER OF SEQ ID NOS: 50

<210> SEQ ID NO 1
<211> LENGTH: 351
<212> TYPE: PRT
<213> ORGANISM: Parachlorella sp
<220> FEATURE:
<221> NAME/KEY: misc_feature
<223> OTHER INFORMATION: RBD domain

<400> SEQUENCE: 1

Met Ser Ser Glu Glu Ile Ser Lys Asp Met Glu Ala Ser Ser Ser
1               5                   10                  15

Gly Asp Gly Gly Gly Lys Leu Phe Leu Gly Gly Leu Ser Trp Asp Thr
            20                  25                  30

Thr Glu Glu Lys Leu Arg Glu His Phe Gly Val Tyr Gly Asp Ile His
        35                  40                  45

Glu Ala Val Val Met Lys Asp Arg Thr Thr Gly Arg Pro Arg Gly Phe
    50                  55                  60

Gly Phe Val Thr Phe Lys Asp Ala Glu Val Ala Asp Arg Val Val Gln
65                  70                  75                  80

Asp Ile His Val Ile Asp Gly Arg Gln Ile Asp Ala Lys Lys Ser Val
                85                  90                  95

Pro Gln Glu Gln Lys Pro Lys Ala Arg Lys Ile Phe Val Gly Gly Leu
            100                 105                 110

Ala Pro Glu Thr Thr Glu Ala Asp Phe Lys Glu Tyr Phe Glu Arg Tyr
        115                 120                 125

Gly Ser Ile Ser Asp Val Gln Ile Met Gln Asp His Met Thr Gly Arg
    130                 135                 140
```

```
Ser Arg Gly Phe Gly Phe Ile Thr Phe Glu Glu Asp Ala Ala Val Glu
145                 150                 155                 160

Lys Val Phe Ala Gln Gly Ala Met Gln Glu Leu Gly Gly Lys Arg Ile
                165                 170                 175

Glu Ile Lys His Ala Thr Pro Lys Gly Ser Ser Pro Thr Thr Pro
            180                 185                 190

Gly Gly Arg Ser Ser Gly Gly Arg Gly Gln Gly Tyr Gly Arg Ala
            195                 200                 205

Met Pro Met Pro Phe Gly Gln Leu Ala Gly Ser Pro Tyr Gly Tyr Gly
        210                 215                 220

Leu Phe His Phe Pro Pro Gly Val Met Pro His Ala Thr Pro Tyr Ser
225                 230                 235                 240

Met Gly Tyr Ala Asn Pro Tyr Leu Met Met Gln Gln Ile Ser Gly Tyr
                245                 250                 255

Pro Gly Ala Thr Pro Tyr Pro Phe Ala Gly Leu Tyr Gly Gly Gln Gly
            260                 265                 270

Arg Gly Ala Ser Gln Gln Leu Gln Gln Ala Gln His Thr Ser Gln Gln
            275                 280                 285

Leu Ser Ser Ser Gly Ala Gly Pro Val Thr Arg Leu Gln Gly Gln Gln
290                 295                 300

Gln Gln Met Pro Gly Gln Gly Ser Arg Gln Gln His Pro Gln Ala Pro
305                 310                 315                 320

Tyr Pro Arg Pro Leu Ala Gly Ser Gly Arg Gly Lys Gly Lys Val Asp
                325                 330                 335

Ser Ala Ser Glu Leu Ser Asn His His His Ser Ala Ala His Ser
            340                 345                 350

<210> SEQ ID NO 2
<211> LENGTH: 853
<212> TYPE: PRT
<213> ORGANISM: Parachlorella sp
<220> FEATURE:
<221> NAME/KEY: misc_feature
<223> OTHER INFORMATION: Trehalose-6-phosphate synthase/phosphatase

<400> SEQUENCE: 2

Met Gly Thr Phe Ser Arg Lys Ser Phe Ser Asn Leu Ala Ala Leu Ala
1               5                   10                  15

Asp Gly Asp Phe Gly Gln Gly Ser Gln Asn Asp Leu Arg Gly Gly Gly
            20                  25                  30

Pro Leu Ser Leu Ser Ser Ala Ala Asn Arg Thr Ser Arg Asn Ser Ile
        35                  40                  45

Asp Ser Asp Gly Arg Arg Leu Gln Arg Leu Ile Phe Val Ser Asn His
50                  55                  60

Leu Pro Leu Arg Val Ser Lys Gly Ala Thr Asp Trp Asn Phe Glu Trp
65                  70                  75                  80

Asp Asp Asp Ala Leu Ile Ala Gln Ala Lys Glu Gly Leu Pro Glu Asp
                85                  90                  95

Met Glu Ala Leu Tyr Val Gly Cys Leu Pro Val Glu Val Asp Pro Gln
            100                 105                 110

Asp Gln Asp Glu Val Ser Leu Gln Leu Gln Lys Gln His Asn Cys Phe
        115                 120                 125

Pro Val Phe Leu Gly Thr Glu Leu Lys Thr Asn Tyr Tyr Arg Lys Phe
    130                 135                 140

Cys Lys Gln Gln Leu Trp Pro Ile Leu His Tyr Leu Ile Pro Leu Asn
145                 150                 155                 160
```

```
Pro Thr Ser Leu Gly Arg Phe Asp Pro Gly Leu Trp Ala Ser Tyr Val
            165                 170                 175

Arg Ala Asn Lys Val Phe Ala Asp Lys Met Val Glu Val Leu Gly Ser
            180                 185                 190

Leu Glu Asp Asp Phe Val Trp Val His Asp Tyr His Leu Leu Val Leu
            195                 200                 205

Pro Ser Leu Leu Arg Lys Arg Phe His Arg Ile Lys Cys Gly Ile Phe
210                 215                 220

Leu His Ser Pro Phe Pro Ser Ser Glu Val Phe Arg Thr Phe Pro Arg
225                 230                 235                 240

Glu Glu Ile Ile Arg Ser Met Leu Asn Ala Asp Leu Ile Gly Phe His
            245                 250                 255

Thr Phe Asp Tyr Ala Arg His Phe Leu Ser Cys Cys Ala Arg Met Leu
            260                 265                 270

Gly Leu Glu His Lys Thr Ser Arg Gly Ala Ile Ile Ile Glu Tyr Tyr
            275                 280                 285

Gly Arg Asp Val Gly Ile Lys Ile Met Pro Thr Gly Val Lys Pro Ser
290                 295                 300

Arg Phe Leu Ser Ala Phe Ser Trp Lys Asp Thr Glu Trp Arg Arg Gly
305                 310                 315                 320

Glu Leu Ala Ala Gln Phe Lys Gly Lys Thr Val Leu Leu Gly Met Asp
            325                 330                 335

Asp Leu Asp Val Phe Lys Gly Ile Glu Leu Arg Leu Ala Ala Phe Lys
            340                 345                 350

Asp Val Leu Glu Tyr His Pro Glu Trp Lys Gly Arg Leu Val Leu Leu
            355                 360                 365

Gln Val Thr Thr Thr Arg Ala Pro Gly Arg Asp Val Asp Asp Leu Phe
            370                 375                 380

Asp Phe Ile Thr Lys Gln Val Glu Glu Ile Asn Glu Arg Phe Gly Ala
385                 390                 395                 400

Pro Gly Tyr Gln Pro Val Val Trp Phe Asn Arg Pro Val Pro Met Tyr
            405                 410                 415

Glu Arg Ile Ala Met Leu Ser Ile Ala Asp Val Ala Val Thr Thr Ala
            420                 425                 430

Thr Arg Asp Gly Met Asn Leu Met Pro Tyr Glu Tyr Val Val Cys Arg
            435                 440                 445

Gln Gly Pro Pro Gly Leu Ala Glu Thr Glu Gly Pro Arg His Ser Gln
450                 455                 460

Leu Val Val Ser Glu Phe Val Gly Cys Ser Pro Ser Leu Ser Gly Ala
465                 470                 475                 480

Ile Arg Val Asn Pro Trp Ser Ile Glu Ala Val Arg Asp Ala Leu Tyr
            485                 490                 495

Gly Ala Ile Arg Met Pro Ile Glu Glu Arg His Ile Arg His Glu Lys
            500                 505                 510

His Trp Lys Tyr Val Ser Ser His Thr Val Gln Phe Trp Ala Lys Ser
            515                 520                 525

Tyr Val Thr Asp Leu Gln Arg Phe Thr Ala Asn His Ser Lys Leu Gln
            530                 535                 540

Cys Phe Asp Leu Gly Phe Ala Leu Asp Thr Phe Arg Met Val Ala Leu
545                 550                 555                 560

Thr Ser Asn Phe Arg Lys Leu Gln Thr Asp Thr Val Val Lys Ala Tyr
            565                 570                 575
```

```
Gln Arg Ala Lys Lys Arg Val Leu Leu Leu Asp His Asp Gly Thr Leu
                580                 585                 590

Met Ala Pro Ser Ser Ile Ser Ser Arg Pro Thr Asp His Val Leu Ala
            595                 600                 605

Thr Leu Arg Gln Leu Thr Ser Asp Pro Arg Asn Thr Val Tyr Ile Ile
        610                 615                 620

Ser Gly Arg Ala Arg Thr Glu Leu Gln Glu Trp Phe Lys Ser Val Pro
625                 630                 635                 640

Asn Leu Gly Leu Ala Ala Glu His Gly Phe Tyr Leu Trp Thr Pro Gly
                645                 650                 655

Ser Ala Asp Trp Ala Val Gln Asp Pro Asp Met Gly Phe Gly Trp Lys
            660                 665                 670

Glu Ile Val Glu Pro Ile Leu Gln Val Tyr Thr Glu Ser Thr Asp Gly
        675                 680                 685

Ser His Ile Glu Ala Lys Glu Ser Ala Leu Val Trp His Tyr Arg Asp
690                 695                 700

Ala Asp Pro Asp Phe Gly Ser Trp Gln Ala Lys Glu Leu Leu Asp His
705                 710                 715                 720

Leu Glu Gly Ile Ile Ser Asn Glu Pro Val Glu Ile Val Ala Gly Gln
                725                 730                 735

Asn Ile Val Glu Val Lys Pro Gln Gly Val Ser Lys Gly Lys Val Val
            740                 745                 750

Glu Arg Ile Leu His Asp Cys Leu Thr Ala Ser Gln Ala Pro Glu Phe
        755                 760                 765

Val Leu Cys Val Gly Asp Asp Arg Ser Asp Glu Asp Met Phe Thr Ala
770                 775                 780

Met Glu Asn Met Gln Phe Ser Pro His Met Pro Val Glu Val Phe Ala
785                 790                 795                 800

Cys Thr Val Gly Gln Lys Pro Ser Lys Ala Pro Phe Tyr Val Asn Asp
                805                 810                 815

Pro Ala Glu Val Gly Gly Cys Gly Ser Arg Met Cys Gly Gly Lys Gly
            820                 825                 830

Gly Glu Gly Ala Ser Ala Pro Glu Thr His Gly Ile Gly Glu Gly Gly
        835                 840                 845

Gly Gly Met His Leu
    850

<210> SEQ ID NO 3
<211> LENGTH: 69
<212> TYPE: PRT
<213> ORGANISM: Parachlorella sp
<220> FEATURE:
<221> NAME/KEY: misc_feature
<223> OTHER INFORMATION: RNA Recognition Motif (RRM) of RNA binding
      domain protein of SEQ ID NO: 3
<220> FEATURE:
<221> NAME/KEY: misc_feature
<223> OTHER INFORMATION: RNA Recognition Motif (RRM) of RNA binding
      domain protein of SEQ ID NO: 1

<400> SEQUENCE: 3

Leu Phe Leu Gly Gly Leu Ser Trp Asp Thr Thr Glu Glu Lys Leu Arg
1               5                   10                  15

Glu His Phe Gly Val Tyr Gly Asp Ile His Glu Ala Val Val Met Lys
                20                  25                  30

Asp Arg Thr Thr Gly Arg Pro Arg Gly Phe Gly Phe Val Thr Phe Lys
            35                  40                  45
```

```
Asp Ala Glu Val Ala Asp Arg Val Gln Asp Ile His Val Ile Asp
 50                  55                  60

Gly Arg Gln Ile Asp
 65
```

<210> SEQ ID NO 4
<211> LENGTH: 234
<212> TYPE: PRT
<213> ORGANISM: Parachlorella sp
<220> FEATURE:
<221> NAME/KEY: misc_feature
<223> OTHER INFORMATION: trehalose-6-phosphate phosphatase/synthase
      active site domain

<400> SEQUENCE: 4

```
Leu Leu Asp His Asp Gly Thr Leu Met Ala Pro Ser Ser Ile Ser Ser
 1               5                  10                  15

Arg Pro Thr Asp His Val Leu Ala Thr Leu Arg Gln Leu Thr Ser Asp
                 20                  25                  30

Pro Arg Asn Thr Val Tyr Ile Ile Ser Gly Arg Ala Arg Thr Glu Leu
             35                  40                  45

Gln Glu Trp Phe Lys Ser Val Pro Asn Leu Gly Leu Ala Ala Glu His
 50                  55                  60

Gly Phe Tyr Leu Trp Thr Pro Gly Ser Ala Asp Trp Ala Val Gln Asp
 65                  70                  75                  80

Pro Asp Met Gly Phe Gly Trp Lys Glu Ile Val Glu Pro Ile Leu Gln
                 85                  90                  95

Val Tyr Thr Glu Ser Thr Asp Gly Ser His Ile Glu Ala Lys Glu Ser
            100                 105                 110

Ala Leu Val Trp His Tyr Arg Asp Ala Asp Pro Asp Phe Gly Ser Trp
        115                 120                 125

Gln Ala Lys Glu Leu Leu Asp His Leu Glu Gly Ile Ile Ser Asn Glu
130                 135                 140

Pro Val Glu Ile Val Ala Gly Gln Asn Ile Val Glu Val Lys Pro Gln
145                 150                 155                 160

Gly Val Ser Lys Gly Lys Val Val Glu Arg Ile Leu His Asp Cys Leu
                165                 170                 175

Thr Ala Ser Gln Ala Pro Glu Phe Val Leu Cys Val Gly Asp Asp Arg
            180                 185                 190

Ser Asp Glu Asp Met Phe Thr Ala Met Glu Asn Met Gln Phe Ser Pro
        195                 200                 205

His Met Pro Val Glu Val Phe Ala Cys Thr Val Gly Gln Lys Pro Ser
    210                 215                 220

Lys Ala Pro Phe Tyr Val Asn Asp Pro Ala
225                 230
```

<210> SEQ ID NO 5
<211> LENGTH: 81
<212> TYPE: PRT
<213> ORGANISM: Parachlorella sp
<220> FEATURE:
<221> NAME/KEY: misc_feature
<223> OTHER INFORMATION: trehalose-6-phosphate phosphatase/synthase
      conserved domain

<400> SEQUENCE: 5

```
Phe Gly Trp Lys Glu Ile Val Glu Pro Ile Leu Gln Val Tyr Thr Glu
 1               5                  10                  15

Ser Thr Asp Gly Ser His Ile Glu Ala Lys Glu Ser Ala Leu Val Trp
```

```
                    20                  25                  30
His Tyr Arg Asp Ala Asp Pro Asp Phe Gly Ser Trp Gln Ala Lys Glu
            35                  40                  45

Leu Leu Asp His Leu Glu Gly Ile Ile Ser Asn Glu Pro Val Glu Ile
        50                  55                  60

Val Ala Gly Gln Asn Ile Val Glu Val Lys Pro Gln Gly Val Ser Lys
65                  70                  75                  80

Gly

<210> SEQ ID NO 6
<211> LENGTH: 4531
<212> TYPE: DNA
<213> ORGANISM: Parachlorella sp
<220> FEATURE:
<221> NAME/KEY: misc_feature
<223> OTHER INFORMATION: SGI1 gene

<400> SEQUENCE: 6
atgtctggtt cagctggatc gggccaggct actctcagac atgacggtgg ctctgctggc      60
ggcagtgggc ctgtctcaga cggttttttca ccggccggcc tgaaggtaaa gtagaaagac    120
actcatacac atcttggttc ggcgttgaaa gtaggtcatt aacatactct ataaccaata    180
tttgtaggtt ctggtcgtgg acgacgacct catgtgcctt aaggtggtgt cagccatgtt    240
gaagaggtgc agctatcaag gtgaggtctt tactggtgtc tgttattgct gtaacatcat    300
ttcgctgttg cacaatttaa acatttgtaa tttactgttg ttattgcagt ggccacttgt    360
agcagtggca gcgaggcact gacacttcta cgtgaacgca acgaggacgg atcctccgac    420
cagttcgacc tcgtactgtc agatgtttac atgccgggta tgtcgtattc ctttgtaaac    480
tttacaatat gcgtctagtt tgacgcgtac actttgtaca ctttgcaaaa acgcaccctg    540
cgaggtctgc catttggtca ctacaacttg ccaccttgg ttgcaagttt gcaagttcgc     600
tctacgtcaa cgctgcaaaa tgaaccaatt gttttgcact gacccctgcca accttcattt    660 gtggctgcag acatggacgg tttcaagctg cttgaacaca tcggtctaga gttggagctt    720
cccgttatca gtaagttgat cgagccgagt ccagagcgaa gcctgcttct atactattag    780
cagctgtctt ttgatatttg acagcttgac ttgatatggt cacagagcat acttgcaacc    840
aggttacctg ttgaactagc aactgtgccc aagcatctct tcaagcacct ccgtcagtcc    900
atagggtact gttgatttgt actctgcaat actgcactgt aatgcgctgt gaatcactgc    960
ccttcacctc tagatggtgc ttccctggag ccctccccca cctccgcctc aagcccctca   1020
catgcctctc ccccccctgc agtgatgtca tccaacgggg acacgaatgt cgtgctgcgg   1080
ggggtcaccc acggggctgt ggactttctg atcaagcccg ttcgaattga ggagctgcgg   1140
aacgtgtggc agcacgtggt gcgtcgtcgt tccatggcgc tggccaggac gccagacgag   1200
gggggacact cggacgagga ctctcaggtg cccttggcag cttctgggcg gcttgctgtg   1260
tcggatgcca cttggactgg ggatgcacga ggggtggggg acaatgggaa gatgggccat   1320
agtaggccag agttgatggc agtggtggtg gggggagta ggcgggagag aagcagccat    1380
cctggtgttg gttttgatga ttgagtgcat ggggatgatg cacaggtgag ctgactggat   1440
gccttgtctt gctgtgctgc gctgcagcgg cacagtgtga aacgcaagga gtcggagcag   1500
agcccgctgc agctcagcac agagcagggc gggaacaaga agccaagagt ggtgtggtcg   1560
gtggagatgc accaacaggt gtgcttgcgg gcggtgtat acgggggagg ggggccagct    1620
gctggctgac ctggcgtgcg cggtgcattg cacttggcga tgagggggcgt gcttcagtat   1680
```

```
gtagctggga cgcaattggt tgtgctgtgt gaccagtgca caaaatacat ccctgaattc    1740
cagtgggttg aacagagttg tcctggaggt gggaagcaaa cgcgcacgtg gtagagggga    1800
gcagggtgca gaacagccgc agcaggggtg ttgcgcagtg tgcaggtatc ctgcctccat    1860
gccccgggcc atgggcatac tacgctggta ccgtcaggat gggcgttgag cctggcttgg    1920
ggggcagggg gcgagcgaat gcggaatggg agcggcaggt gctgggaggg tggctgactg    1980
gcttgcagga gcgcaagtcc tgtcggggc gtcgtcctgt tccctcctgc ccgcttcacc     2040
cacgttcact ctcatgcctc cacactcctg ctgctgacac acctgtcgcc acctccgctg    2100
cagtttgtga acgcggtcaa ctccctgggc attgacaagg cggtgcccaa gcggattctg    2160
gacctgatga acgtggaggg gctgacgcgc gagaacgtgg ccagccatct gcaggtgcct    2220
gccatgaccc ctcccaccag ggacctggtg ttttgacacc ctggaactcc tctttgacgg    2280
agcctccagt tcaattccag caatcgaatt gaatcaaaaa gcatgtgcac ccacgtgctg    2340
tttgaatgtc ccatgtggta ggaaacacaa ctgcccctt gccatttgct ggagggtgcc     2400
cgctgcgcca tgcccgagtg cgctgtgctc agcgttgtgc tgcgccccc gctgactgaa     2460 gctgacagcg tgcggctgag gagggtactg ggggaggggg ggtgggaggc ggccgctggc    2520
ggcggaaggg agggtgtgca cgcatggaca cagggccttt ccgccctgca cggcctctac    2580
tgcaccctgc cacgtgatgt atcgacatgg tgggccatgc tgtgctgtgc cgctgcagaa    2640
gtaccgcctg tacctgaagc gggtggaggg agtgcaatcg ggtgcggcag cctccaagca    2700
gcaccagcac ccgcagtatc accagcagca gcagcagcag caagcgcaac ctcgtgcagc    2760
tgtctcccct gcagcagctt cctttggtgc cctttccttg ggagcccgc agcaggcgca     2820 gcagggcatg ccgcagctgg ggatgcctgt gcaggtgaag actgccccc ccccctccc      2880 cctttccatc ttccctccat cagcctgctg ttccttaccc ttgtcaaccc gtctctcctt    2940
tttcgcaagc agcgcaccac ccccatgca cgccttgcct ggcactgttg tcagctgccc     3000
ccctagaaat acacaaggtg tgggtgcaac tggtgggacc cctccccccc cccccctggg    3060
gctgcagggt ctccctccaa acttggcagc catgggatcc cagccgccgc acatcccctt    3120
ccagcaggcc ctggccatgc aggcggcggc tgcggcggct gcagcagcg gcgcgctccc     3180 cgggagtctg cccccctaca tgccacccc ggggatgatg ccccccggca tgccgggggg     3240
ggtccccggt atgggagggg tggtgggca tcctcaggta cgggcagcac atgagtgggc    3300 agggtattg gagaggggaa gggcagggag gttgcatgtg aggggctgca tggcaaagag     3360
gctgcagcgc aggtgttgct tgcagcactt ccctcggtg gcgcttgcat caaattttga     3420
atcctccccc gatgggcacg cccgtgtgtg ggggggggtg ggatggggga tggggtggt    3480 tttgtggcat gtcgggcgct ttcatctacc cgggcccctg ccctgcctg tacgcgtgcg     3540 catgtgtgca gatgcccgcc ccagggatgg actttgcggg tttcaacggg tatggcaacg    3600
ctgcgggggg gctgatgttt ggcgggcagc agcaggcgca gcacgcgcag cagcacgcgt    3660
cagcgcaagc gggctcgctg gcgcagcagc aggcgcagca agtatccatg ggcttgggcc    3720
ttatgccccc ccgttgggg ttccgcccca cctcgctcgc cgcgccagcc ccgcgctccg     3780
cagcaactga gcccgccgca gccccactcc ccctgacgtc ctcgccgcca gctgcttcag    3840
caggcggcag cggcggccca gcagcagctg ctccgcagca cagcagcggc gccgcagcag    3900
cccaagcccc ccatcaccac ccacagtgct cggagcaggg agcggggggg ctcccgcccc    3960
cgctgcccgc gtccagcgcc ccgcagtcct atccctctccc tcccccctcc tcgcaggccg    4020
```

```
ctttgcatga cccggacgaa cactaccccc caggctcggc agaggtgagc acgtcccccc    4080 gcccctccc ccccccccc ccccttccc ttcaccctgg cttggcgtgc aatgaaaccc        4140
taaataaccc taaaacctca ttatcagttg caaattggac ccgtgaagcg ggcgggggca     4200
actgcgctct gctggtgtca gcgctgtctc tgccggttcc tgcccagcgt gcgcctgcat     4260
gcaagggggg atggggggggg ggaggcattt aacaataggc cagtcatctc caatccaccg   4320
tcaatttcag ccccctcccc ccccctccct catcccttg cagatgcacc accagcacct     4380
cccagggctg tgtggcttta acccggacga cctgctgggg gggcagctgg gggacatggg    4440
gttcctgggg gagctggggg gggcggtggg aggaaagcac gaacaggacg acttcctgga    4500
cctgctgctg aaggggagg aggagctgtg a                                    4531
```

<210> SEQ ID NO 7
<211> LENGTH: 1860
<212> TYPE: DNA
<213> ORGANISM: Parachlorella sp
<220> FEATURE:
<221> NAME/KEY: misc_feature
<223> OTHER INFORMATION: SGI1 gene coding sequence

<400> SEQUENCE: 7

```
atgtctggtt cagctggatc gggccaggct actctcagac atgacggtgg ctctgctggc      60
ggcagtgggc ctgtctcaga cggttttca ccggccggcc tgaaggttct ggtcgtggac      120
gacgacctca tgtgccttaa ggtggtgtca gccatgttga agaggtgcag ctatcaagtg    180
gccacttgta gcagtggcag cgaggcactg acacttctac gtgaacgcaa cgaggacgga    240
tcctccgacc agttcgacct cgtactgtca gatgtttaca tgccggacat ggacggtttc    300
aagctgcttg aacacatcgg tctagagttg gagcttcccg ttatcatgat gtcatccaac    360
ggggacacga atgtcgtgct gcgggggtc acccacgggg ctgtggactt tctgatcaag    420
cccgttcgaa ttgaggagct gcggaacgtg tggcagcacg tggtgcgtcg tcgttccatg    480
gcgctggcca ggacgccaga cgaggggga cactcggacg aggactctca gcggcacagt    540
gtgaaacgca aggagtcgga gcagagcccg ctgcagctca gcacagagca gggcgggaac   600
aagaagccaa gagtggtgtg gtcggtggag atgcaccaac agtttgtgaa cgcggtcaac   660
tccctgggca ttgacaaggc ggtgcccaag cggattctgg acctgatgaa cgtggagggg   720
ctgacgcgcg agaacgtggc cagccatctg cagaagtacc gcctgtacct gaagcgggtg   780
gagggagtgc aatcgggtgc ggcagcctcc aagcagcacc agcacccgca gtatcaccag   840
cagcagcagc agcagcaagc gcaacctcgt gcagctgtct cccctgcagc agcttccttt   900
ggtgcccttt ccttgggagc cccgcagcag gcgcagcagg gcatgccgca gctggggatg  960
cctgtgcagg gtctccctcc aaacttggca gccatgggat cccagccgcc gcacatcccc  1020
ttccagcagg ccctggccat gcaggcggcg gctgcggcgg ctgcagccag cggcgcgctc  1080
cccgggagtc tgcccccta catgccaccc cggggatga tgcccccgg catgccgggg     1140 ggggtccccg gtatgggagg ggtggtgggg catcctcaga tgcccgcccc agggatggac  1200
tttgcgggtt caacgggta tggcaacgct gcgggggggc tgatgtttgg cgggcagcag   1260
caggcgcagc acgcgcagca gcacgcgtca gcgcaagcgg gctcgctggc gcagcagcag   1320
gcgcagcaag tatccatggg cttgggcctt atgcccccc cgttggggtt cccgcccacc    1380
tcgctcgccg cgccagcccc gcgctccgca gcaactgagc ccgccgcagc ccactcccc    1440 ctgacgtcct cgccgccagc tgcttcagca ggcggcagcg gcggcccagc agcagctgct   1500
```

```
ccgcagcaca gcagcggcgc cgcagcagcc caagcccccc atcaccaccc acagtgctcg    1560
gagcagggag cggggggggct cccgcccccg ctgcccgcgt ccagcgcccc gcagtcctat    1620
cccctccctc ccccctcctc gcaggccgct ttgcatgacc cggacgaaca ctaccccca     1680 ggctcggcag agatgcacca ccagcacctc ccagggctgt gtggctttaa cccggacgac    1740
ctgctggggg ggcagctggg ggacatgggg ttcctggggg agctgggggg ggcggtggga    1800
ggaaagcacg aacaggacga cttcctggac ctgctgctga aggggagga ggagctgtga     1860

<210> SEQ ID NO 8
<211> LENGTH: 619
<212> TYPE: PRT
<213> ORGANISM: Parachlorella sp
<220> FEATURE:
<221> NAME/KEY: misc_feature
<223> OTHER INFORMATION: SGI1 polypeptide

<400> SEQUENCE: 8
```

Met Ser Gly Ser Ala Gly Ser Gly Gln Ala Thr Leu Arg His Asp Gly
1               5                   10                  15

Gly Ser Ala Gly Gly Ser Gly Pro Val Ser Asp Gly Phe Ser Pro Ala
            20                  25                  30

Gly Leu Lys Val Leu Val Val Asp Asp Leu Met Cys Leu Lys Val
        35                  40                  45

Val Ser Ala Met Leu Lys Arg Cys Ser Tyr Gln Val Ala Thr Cys Ser
50                  55                  60

Ser Gly Ser Glu Ala Leu Thr Leu Leu Arg Glu Arg Asn Glu Asp Gly
65                  70                  75                  80

Ser Ser Asp Gln Phe Asp Leu Val Leu Ser Asp Val Tyr Met Pro Asp
                85                  90                  95

Met Asp Gly Phe Lys Leu Leu Glu His Ile Gly Leu Glu Leu Glu Leu
            100                 105                 110

Pro Val Ile Met Met Ser Ser Asn Gly Asp Thr Asn Val Val Leu Arg
        115                 120                 125

Gly Val Thr His Gly Ala Val Asp Phe Leu Ile Lys Pro Val Arg Ile
130                 135                 140

Glu Glu Leu Arg Asn Val Trp Gln His Val Val Arg Arg Ser Met
145                 150                 155                 160

Ala Leu Ala Arg Thr Pro Asp Glu Gly Gly His Ser Asp Glu Asp Ser
                165                 170                 175

Gln Arg His Ser Val Lys Arg Lys Glu Ser Glu Gln Ser Pro Leu Gln
            180                 185                 190

Leu Ser Thr Glu Gln Gly Gly Asn Lys Lys Pro Arg Val Val Trp Ser
        195                 200                 205

Val Glu Met His Gln Gln Phe Val Asn Ala Val Asn Ser Leu Gly Ile
210                 215                 220

Asp Lys Ala Val Pro Lys Arg Ile Leu Asp Leu Met Asn Val Glu Gly
225                 230                 235                 240

Leu Thr Arg Glu Asn Val Ala Ser His Leu Gln Lys Tyr Arg Leu Tyr
                245                 250                 255

Leu Lys Arg Val Glu Gly Val Gln Ser Gly Ala Ala Ser Lys Gln
            260                 265                 270

His Gln His Pro Gln Tyr His Gln Gln Gln Gln Gln Ala Gln
        275                 280                 285

Pro Arg Ala Ala Val Ser Pro Ala Ala Ser Phe Gly Ala Leu Ser
290                 295                 300

Leu Gly Ala Pro Gln Gln Ala Gln Gln Gly Met Pro Gln Leu Gly Met
305                 310                 315                 320

Pro Val Gln Gly Leu Pro Asn Leu Ala Ala Met Gly Ser Gln Pro
            325                 330                 335

Pro His Ile Pro Phe Gln Gln Ala Leu Ala Met Gln Ala Ala Ala
            340                 345                 350

Ala Ala Ala Ala Ser Gly Ala Leu Pro Gly Ser Leu Pro Pro Tyr Met
            355                 360                 365

Pro Pro Pro Gly Met Met Pro Pro Gly Met Pro Gly Gly Val Pro Gly
            370                 375                 380

Met Gly Gly Val Val Gly His Pro Gln Met Pro Ala Pro Gly Met Asp
385                 390                 395                 400

Phe Ala Gly Phe Asn Gly Tyr Gly Asn Ala Ala Gly Gly Leu Met Phe
                405                 410                 415

Gly Gly Gln Gln Gln Ala Gln His Ala Gln Gln His Ala Ser Ala Gln
            420                 425                 430

Ala Gly Ser Leu Ala Gln Gln Ala Gln Gln Val Ser Met Gly Leu
            435                 440                 445

Gly Leu Met Pro Pro Pro Leu Gly Phe Pro Pro Thr Ser Leu Ala Ala
    450                 455                 460

Pro Ala Pro Arg Ser Ala Ala Thr Glu Pro Ala Ala Ala Pro Leu Pro
465                 470                 475                 480

Leu Thr Ser Ser Pro Pro Ala Ala Ser Ala Gly Gly Ser Gly Gly Pro
            485                 490                 495

Ala Ala Ala Ala Pro Gln His Ser Ser Gly Ala Ala Ala Ala Gln Ala
            500                 505                 510

Pro His His His Pro Gln Cys Ser Glu Gln Gly Ala Gly Gly Leu Pro
            515                 520                 525

Pro Pro Leu Pro Ala Ser Ser Ala Pro Gln Ser Tyr Pro Leu Pro Pro
    530                 535                 540

Pro Ser Ser Gln Ala Ala Leu His Asp Pro Asp Glu His Tyr Pro Pro
545                 550                 555                 560

Gly Ser Ala Glu Met His His Gln His Leu Pro Gly Leu Cys Gly Phe
                565                 570                 575

Asn Pro Asp Asp Leu Leu Gly Gly Gln Leu Gly Asp Met Gly Phe Leu
            580                 585                 590

Gly Glu Leu Gly Gly Ala Val Gly Gly Lys His Glu Gln Asp Asp Phe
            595                 600                 605

Leu Asp Leu Leu Leu Lys Gly Glu Glu Leu
    610                 615

<210> SEQ ID NO 9
<211> LENGTH: 302
<212> TYPE: PRT
<213> ORGANISM: Coccomyxa subellipsoidea
<220> FEATURE:
<221> NAME/KEY: misc_feature
<223> OTHER INFORMATION: SGI1 polypeptide, NCBI Accession XP_005652114

<400> SEQUENCE: 9

Met Gly Leu Lys Ala Arg Ala Ala Ser Val Ser Val His Ser Ser Ala
1               5                   10                  15

Asn Asn Thr Ala Ser Pro Leu Ser Ser Gly Arg Arg Gly Phe Pro His
            20                  25                  30

Ser Gly Glu Met Ser Gly Glu Asp Leu Ala Arg Ser Asp Ser Trp Glu

```
            35                  40                  45
Met Phe Pro Ala Gly Leu Lys Val Leu Val Asp Asp Asp Pro Leu
 50                  55                  60

Cys Leu Lys Val Val Glu His Met Leu Arg Arg Cys Asn Tyr Gln Val
 65                  70                  75                  80

Thr Thr Cys Pro Asn Gly Lys Ala Ala Leu Glu Lys Leu Arg Asp Arg
                 85                  90                  95

Ser Val His Phe Asp Leu Val Leu Ser Asp Val Tyr Met Pro Asp Met
                100                 105                 110

Asp Gly Phe Lys Leu Leu Glu His Ile Gly Leu Glu Leu Asp Leu Pro
            115                 120                 125

Val Ile Met Met Ser Ser Asn Gly Glu Thr Asn Val Val Leu Arg Gly
130                 135                 140

Val Thr His Gly Ala Val Asp Phe Leu Ile Lys Pro Arg Val Glu
145                 150                 155                 160

Glu Leu Arg Asn Val Trp Gln His Val Arg Arg Lys Arg Asp Gln
                165                 170                 175

Ala Val Ser Gln Ala Arg Asp Ser Arg Asp Ile Ser Asp Glu Glu Gly
            180                 185                 190

Thr Asp Asp Gly Lys Pro Arg Asp Lys Lys Arg Lys Glu Val Ile Leu
            195                 200                 205

Val Leu Trp Trp Asp Met Gln Arg Arg Asp Ser Asp Asp Gly Val Ser
210                 215                 220

Ala Lys Lys Ala Arg Val Val Trp Ser Val Glu Met His Gln Gln Phe
225                 230                 235                 240

Val Gln Ala Val Asn Gln Leu Gly Ile Asp Lys Ala Val Pro Lys Arg
                245                 250                 255

Ile Leu Asp Leu Met Asn Val Asp Gly Leu Thr Arg Glu Asn Val Ala
            260                 265                 270

Ser His Leu Gln Val Pro His Leu Ser Ile Phe Ser Pro Leu Phe Ala
            275                 280                 285

Glu Leu Met Ser Thr Leu Pro Arg Arg Cys Phe Tyr Asp Phe
290                 295                 300

<210> SEQ ID NO 10
<211> LENGTH: 270
<212> TYPE: PRT
<213> ORGANISM: Ostreococcus lucimarinus
<220> FEATURE:
<221> NAME/KEY: misc_feature
<223> OTHER INFORMATION: SGI1 polypeptide, NCBI Accession XP_001415508

<400> SEQUENCE: 10

Phe Pro Ala Gly Leu Gly Val Leu Val Asp Asp Asp Leu Leu Cys
 1               5                  10                  15

Leu Lys Val Val Glu Lys Met Leu Lys Ala Cys Lys Tyr Lys Val Thr
                 20                  25                  30

Ala Cys Ser Thr Ala Lys Thr Ala Leu Glu Ile Leu Arg Thr Arg Lys
             35                  40                  45

Glu Glu Phe Asp Ile Val Leu Ser Asp Val His Met Pro Asp Met Asp
 50                  55                  60

Gly Phe Lys Leu Leu Glu Ile Ile Gln Phe Glu Leu Ala Leu Pro Val
 65                  70                  75                  80

Leu Met Met Ser Ala Asn Ser Asp Ser Ser Val Val Leu Arg Gly Ile
                 85                  90                  95
```

```
Ile His Gly Ala Val Asp Tyr Leu Leu Lys Pro Val Arg Ile Glu Glu
            100                 105                 110

Leu Arg Asn Ile Trp Gln His Val Val Arg Arg Asp Tyr Ser Ser Ala
        115                 120                 125

Lys Ser Gly Ser Glu Asp Val Glu Ala Ser Ser Pro Ser Lys Arg
    130                 135                 140

Ala Lys Thr Ser Gly Ser Asn Ser Lys Ser Glu Glu Val Asp Arg Thr
145                 150                 155                 160

Ala Ser Glu Met Ser Ser Gly Lys Ala Arg Lys Lys Pro Thr Gly Lys
                165                 170                 175

Lys Gly Gly Lys Ser Val Lys Glu Ala Glu Lys Lys Asp Val Val Asp
            180                 185                 190

Asn Ser Asn Ser Lys Lys Pro Arg Val Val Trp Ser Ala Glu Leu His
        195                 200                 205

Ala Gln Phe Val Thr Ala Val Asn Gln Leu Gly Ile Asp Lys Ala Val
    210                 215                 220

Pro Lys Arg Ile Leu Asp Leu Met Gly Val Gln Gly Leu Thr Arg Glu
225                 230                 235                 240

Asn Val Ala Ser His Leu Gln Lys Tyr Arg Leu Tyr Leu Lys Arg Leu
                245                 250                 255

Gln Gly Asn Asp Ala Arg Gly Gly Asn Ala Ser Ser Thr
            260                 265                 270

<210> SEQ ID NO 11
<211> LENGTH: 941
<212> TYPE: PRT
<213> ORGANISM: Chlamydomonas reinhardtii
<220> FEATURE:
<221> NAME/KEY: misc_feature
<223> OTHER INFORMATION: SGI1 polypeptide

<400> SEQUENCE: 11

Met Asp Ser Gln Gly Val Lys Leu Glu Glu His Pro Gly His Thr Gly
1               5                   10                  15

Gly His Trp Gln Gly Phe Pro Ala Gly Leu Arg Leu Leu Val Val Asp
            20                  25                  30

Asp Asp Pro Leu Cys Leu Lys Val Val Glu Gln Met Leu Arg Lys Cys
        35                  40                  45

Ser Tyr Glu Val Thr Val Cys Ser Asn Ala Thr Thr Ala Leu Asn Ile
    50                  55                  60

Leu Arg Asp Lys Asn Thr Glu Tyr Asp Leu Val Leu Ser Asp Val Tyr
65                  70                  75                  80

Met Pro Asp Met Asp Gly Phe Arg Leu Leu Glu Leu Val Gly Leu Glu
                85                  90                  95

Met Asp Leu Pro Val Ile Met Met Ser Ser Asn Gly Asp Thr Ser Asn
            100                 105                 110

Val Leu Arg Gly Val Thr His Gly Ala Cys Asp Tyr Leu Ile Lys Pro
        115                 120                 125

Val Arg Leu Glu Glu Leu Arg Asn Leu Trp Gln His Val Val Arg Arg
    130                 135                 140

Arg Arg Gln His Ala Gln Glu Ile Asp Ser Asp Glu Gln Ser Gln Glu
145                 150                 155                 160

Arg Asp Glu Asp Gln Thr Arg Asn Lys Arg Lys Ala Asp Ala Ala Gly
                165                 170                 175

Val Thr Gly Asp Gln Cys Arg Leu Asn Gly Ser Gly Ser Gly Gly Ala
            180                 185                 190
```

```
Ala Gly Pro Gly Ser Gly Gly Ala Gly Gly Met Thr Asp Glu Met
        195                 200                 205

Leu Met Met Ser Gly Gly Glu Asn Gly Ser Asn Lys Lys Ala Arg Val
    210                 215                 220

Val Trp Ser Val Glu Met His Gln Gln Phe Val Asn Ala Val Asn Gln
225                 230                 235                 240

Leu Gly Ile Asp Lys Ala Val Pro Lys Lys Ile Leu Glu Ile Met Gly
                245                 250                 255

Val Asp Gly Ser Ala Gly Arg Leu Ala Asp Thr Ser Gly Arg Asp Val
                260                 265                 270

Cys Gly Thr Val Tyr Arg Leu Tyr Leu Lys Arg Val Ser Gly Val Thr
                275                 280                 285

Pro Ser Gly His His His Asn Ala Ala His Lys Ser Asn Lys Pro Ser
    290                 295                 300

Pro His Thr Thr Pro Pro Pro Ala Leu Pro Gly Gln Ala Gly Thr
305                 310                 315                 320

His Pro Ala Asn Gln Ala Thr Ala Ile Pro Pro Pro Gln Pro Gly
                325                 330                 335

Ser Gly Thr Ala Ala Gly Ala Gly Ala Ala Ala Gly Thr Gly Gly
                340                 345                 350

Gly Ala Ala Ala Ala Asn Gly His Ala Ala Thr Thr Gly Ala Gly Thr
                355                 360                 365

Pro Gly Ala Ala Pro Gly Ala Gly Gly Val Gly Gly Thr Gly Ala
    370                 375                 380

Gly Gly Leu Gly Ser Gly Pro Asp Gly Ala Ala Ala Ala Gly Pro
385                 390                 395                 400

Gly Pro Gly Ala Ala Val Pro Gly Gly Leu Gly Gly Leu Pro Leu Pro
                405                 410                 415

Pro Gly Ala Gly Pro Gly Pro Gly Pro Gly Gly Phe Gly Gly Pro Ser
                420                 425                 430

Pro Pro Pro Pro Pro His Pro Ala Ala Leu Leu Ala Asn Pro Met Ala
                435                 440                 445

Ala Ala Val Ala Gly Leu Asn Gln Ser Leu Leu Asn Ala Met Gly Ser
    450                 455                 460

Leu Gly Val Gly Val Gly Gly Met Ser Pro Leu Gly Pro Val Gly Pro
465                 470                 475                 480

Leu Gly Pro Leu Gly Gly Leu Pro Gly Leu Pro Gly Met Gln Pro Pro
                485                 490                 495

Pro Leu Gly Met Gly Gly Leu Gln Pro Gly Met Gly Pro Leu Gly Pro
                500                 505                 510

Leu Gly Leu Pro Gly Met Gly Gly Leu Pro Gly Leu Pro Gly Met Asn
                515                 520                 525

Pro Met Ala Asn Leu Met Gln Gly Met Ala Ala Gly Met Ala Ala
    530                 535                 540

Asn Gln Met Asn Gly Met Gly Gly His Met Gly Gly His Met Gly Gly
545                 550                 555                 560

Met Asn Gly Pro Met Gly Ala Leu Ala Gly Met Asn Gly Leu Asn Gly
                565                 570                 575

Ala Met Met Gly Gly Leu Pro Gly Met Gly Gly Pro Gln Asn Met Phe
                580                 585                 590

Gln Ala Ala Ala Ala Ala Ala Ala Gln Gln Gln Gln Gln Gln Gln Glu
                595                 600                 605
```

-continued

```
Gln Gln His Ala Met Met Gln Gln Ala Ala Ala Gly Leu Leu Ala Ser
    610                 615                 620
Gln Gln Gln Gln Gln Gln Gln Gln Gln Gln Gln Gln Gln Gln Gln Ala
625                 630                 635                 640
Leu Gln Gln Gln Gln Gln Gly Met Ala Val Ser Pro Pro Gly Pro
            645                 650                 655
His Asn Ala Thr Pro Asn Gly Gln Leu His Thr His Pro Gln Ala His
        660                 665                 670
His Pro His Gln His Gly Leu His Ala His Ala His Pro His Gln His
    675                 680                 685
Leu Asn Thr Ala Pro Ala Gly Ala Leu Gly Leu Ser Pro Pro Gln Pro
690                 695                 700
Pro Ala Gly Leu Leu Ser Ala Ser Gly Leu Ser Ser Gly Pro Asp Gly
705                 710                 715                 720
Ser Gly Leu Gly Ser Gly Val Gly Gly Leu Leu Asp Gly Leu Gln Gln
            725                 730                 735
His Pro His His Pro Gln Leu Gln Leu Ala Gly Ser Leu Gly Thr Gly
        740                 745                 750
Gly Thr Gly Arg Ser Ser Gly Ala Ala Gly Arg Gly Ser Leu Asp Leu
    755                 760                 765
Pro Ala Asp Leu Met Gly Met Ala Leu Leu Asp Phe Pro Pro Val Pro
770                 775                 780
Val Pro Gly Gly Ala Asp Val Gly Met Ala Gly Ala Gly Gly Gly Ala
785                 790                 795                 800
Ala Gly Ala His His Gly His Gln Gly His Gln Gly Ile Gly Gly
            805                 810                 815
Gly Ala Gly Val Gly Ile Ala Gly Gly Val Gly Cys Gly Val Pro Ala
        820                 825                 830
Ala Ala His Gly Leu Glu Pro Ala Ile Leu Met Asp Asp Pro Ala Asp
    835                 840                 845
Leu Gly Ala Val Phe Ser Asp Val Met Tyr Gly Thr Pro Gly Gly Gly
850                 855                 860
Gly Val Pro Gly Gly Val Pro Gly Gly Val Gly Leu Gly Leu Gly
865                 870                 875                 880
Ala Gly Gln Val Pro Ser Gly Pro Ala Gly Ala Gly Leu His Ser
            885                 890                 895
His His His Gln His His His Gln His His Leu Gly His Val Val
        900                 905                 910
Pro Val Gly Gly Val Asp Pro Leu Ala Gly Asp Ala Ala Lys Met Ala
    915                 920                 925
Met Asn Asp Asp Asp Phe Phe Asn Phe Leu Leu Lys Asn
930                 935                 940

<210> SEQ ID NO 12
<211> LENGTH: 523
<212> TYPE: PRT
<213> ORGANISM: Chromochloris zofingiensis
<220> FEATURE:
<221> NAME/KEY: misc_feature
<223> OTHER INFORMATION: SGI1 polypeptide

<400> SEQUENCE: 12

Met Asp Gly Phe Lys Leu Leu Glu Thr Val Gly Leu Glu Leu Asp Leu
1               5                   10                  15
Pro Val Ile Met Met Ser Ser Asn Gly Glu His Thr Thr Val Met Arg
            20                  25                  30
```

Gly Val Thr His Gly Ala Cys Asp Phe Leu Ile Lys Pro Val Arg Ile
            35                  40                  45

Glu Glu Leu Arg Asn Ile Trp Gln His Val Ile Arg Arg Thr Arg His
    50                  55                  60

Pro Val Phe Arg Asp Leu Glu Pro Asp His Glu Gly Gly Asp Tyr
65                  70                  75                  80

Glu Ala Ser Lys Lys Arg Lys Asp Leu Tyr Arg Gly Glu Asn Ser Ser
                85                  90                  95

Gly Ser Gly Gly Ala Gly Gly Leu Glu Arg Asp Asp Asp Gly Ser Ala
            100                 105                 110

Ser Lys Lys Pro Arg Val Val Trp Ser Val Glu Met His Gln Gln Phe
            115                 120                 125

Val Gln Ala Val Asn Gln Leu Gly Ile Asp Lys Ala Val Pro Lys Lys
            130                 135                 140

Ile Leu Glu Leu Met Asn Val Asp Gly Leu Thr Arg Glu Asn Val Ala
145                 150                 155                 160

Ser His Leu Gln Lys Tyr Arg Leu Tyr Leu Lys Arg Val Gln Gly Val
                165                 170                 175

Gln Ala Pro Phe Gly Leu Pro Asn Ile Gln Leu Pro Arg Gln Thr Ser
            180                 185                 190

Ser Lys Gly Ala Gly Ser Ser Ser Gln Gln His His Gln Gln
            195                 200                 205

Gln His Gln Gln Gln His Gln His Gln His Gln Thr Ala Leu Gly Thr
            210                 215                 220

Gly Gln Gln Gln Ser His Gln Leu Gln Pro Cys Pro Val Ser Thr Ala
225                 230                 235                 240

Thr Pro Val Met Pro Ser Pro Asp Ala Met Val Ala Ala Ser Met Met
                245                 250                 255

Ser Ser Gln Ala Met Ala Ala Met Ala Pro Gly Val Met Asn Pro Met
            260                 265                 270

Thr Ala Met Asn Ser Met Met Ala Gly Leu Asn Pro Asn Met Met Gly
            275                 280                 285

Met Ala Ala Gly Leu Gly Leu Ala Gly Leu Gly Ile Gly Gly Met Ala
            290                 295                 300

Gly His Pro Val Pro Asn Pro Met Leu Ala Gly Met Gly Pro Met Gly
305                 310                 315                 320

Leu Gly Leu Pro Pro Pro Pro Gly Met Pro Pro Pro Pro Gly Met
                325                 330                 335

Pro Pro Gly Met Pro Pro Gly Met Pro Pro Gly Met Pro Ala Met Met
                340                 345                 350

Gln Gly Leu Ser Met Ala Gly Met Ser His Leu Ala Ala Ala Gly Met
            355                 360                 365

Arg Pro Pro Pro Gly Ala Leu Gly Gly His Leu Gly Gly Pro Gly Leu
            370                 375                 380

Ser Pro Phe Gly Pro Pro Pro Pro Gly Ala Asp Pro Ala Asn Met
385                 390                 395                 400

Met Ala Asn Met Ser Ser Met Met Ala Asn Met Gln Ala Ala Leu Ala
                405                 410                 415

Phe Gln Ala Asp Ala Ala Ala Ala Gln His Gln Ala Ala Ser Thr
            420                 425                 430

Gly Ser Val Ala Pro Gly Arg Gln Gln Gln Val His Gln His Gln Gln
            435                 440                 445

```
Ala Val Gly Met Ala Val Asp Asp Ala Ala Phe Pro Ser Pro Gly
            450                 455                 460

Cys Arg Pro Asn Gly Ser Ala Asp Ala Gly Ala Gln Ser Ala Ala Glu
465                 470                 475                 480

Pro Asn Asp Phe Ser Arg Val Phe Asp Asp Pro Phe Ala Gln Pro Ala
                    485                 490                 495

Ala Ser Pro Ser Gly Ala Ala Ala Gly Ser Asn Glu Ala Pro Gly
                500                 505                 510

Met Asp Asp Phe Leu Asp Phe Phe Leu Lys Ser
            515                 520
```

<210> SEQ ID NO 13
<211> LENGTH: 832
<212> TYPE: PRT
<213> ORGANISM: Volvox carteri
<220> FEATURE:
<221> NAME/KEY: misc_feature
<223> OTHER INFORMATION: SGI1 polypeptide

<400> SEQUENCE: 13

```
Met Asp Gly Arg Ala Glu Gly Thr Val Ala Ile Lys Gln Glu Asp His
1               5                   10                  15

Ala Ser Gly His Trp His Asn Phe Pro Ala Gly Leu Arg Leu Leu Val
                20                  25                  30

Val Asp Asp Asp Pro Leu Cys Leu Lys Val Val Glu Gln Met Leu Arg
            35                  40                  45

Lys Cys Ser Tyr Asp Val Thr Thr Cys Thr Asn Ala Thr Met Ala Leu
50                  55                  60

Asn Leu Leu Arg Asp Lys Ser Thr Glu Tyr Asp Leu Val Leu Ser Asp
65                  70                  75                  80

Val Tyr Met Pro Asp Met Asp Gly Phe Lys Leu Leu Glu Val Val Gly
                85                  90                  95

Leu Glu Met Asp Leu Pro Val Ile Met Met Ser Ser Asn Gly Asp Thr
            100                 105                 110

Ser Asn Val Leu Arg Gly Val Thr His Gly Ala Cys Asp Tyr Leu Ile
        115                 120                 125

Lys Pro Val Arg Leu Glu Glu Leu Arg Asn Leu Trp Gln His Val Val
130                 135                 140

Arg Arg Arg Arg Gln Leu Asn Leu Asp Met Asp Ser Asp Glu His Ser
145                 150                 155                 160

Gln Glu Arg Asp Asp Gln Gly Arg Lys Arg Lys Ala Asp Thr Ala
                165                 170                 175

Gly Cys Ile Gly Asp Gln Leu Arg Met Met Gly Ala Gly Cys Ser Gly
            180                 185                 190

Gly Ala Asn Gly Leu Gly Ser Thr Gly Asn Leu Gly Ala Val Ala Thr
        195                 200                 205

Gly Ser Ala Gly Leu Gly Leu Gly Leu Gly Thr Ala Ala Asp Glu Leu
    210                 215                 220

Gly Leu Gly Leu Asp Asn Gly Ser Ser Lys Lys Ala Arg Val Val Trp
225                 230                 235                 240

Ser Val Glu Met His Gln Gln Phe Val Asn Ala Val Asn Gln Leu Gly
                245                 250                 255

Ile Asp Lys Ala Val Pro Lys Lys Ile Leu Glu Ile Met Asn Val Asp
            260                 265                 270

Gly Leu Thr Arg Glu Asn Val Ala Ser His Leu Gln Lys Tyr Arg Leu
        275                 280                 285
```

```
Tyr Leu Lys Arg Val Ser Gly Ala Gln Gln Pro Gly Gln Asn Arg Val
    290                 295                 300

Ser Arg Pro Ser Pro Pro Gln Pro Gln Ser Pro Gln Val Pro Ser Gln
305                 310                 315                 320

Gln Gln Gln Ser Leu Pro Gly Gly Gly Ala Ala Ala Ala Gly Ala
                325                 330                 335

Gly Gln Leu Gln Gly Gly Gly Ala Ala Ala Ala Ala Ser Leu
            340                 345                 350

Ala Ser Ile Leu Ala Gly Gly Pro Ala Gly Gly Ala Gly Ala
        355                 360                 365

Gly Pro Pro Gly Gly Gly Gln Leu Gly Ala Asp Gly Gly Pro
    370                 375                 380

Gly Pro Gly Leu Ser Ser Ala Val Ala Asn Ala Met Ser Ala Ala
385                 390                 395                 400

Ala Ala Gly Gly Phe Pro Thr Pro Pro Pro Pro Pro His Pro
                405                 410                 415

Ala Ala Leu Leu Ala Ala Asn Pro Met Met Ala Ala Ala Gly Leu
            420                 425                 430

Asn Pro Leu Leu Gly Ala Met Gly Gly Leu Gly Val Gly Pro Leu Gly
        435                 440                 445

Pro Leu Asn Pro Leu Asn Gly Met Pro Met Pro Gly Met Gln Pro Pro
450                 455                 460

Leu Gly Leu Leu Pro Gly Leu Pro Gly Pro Gly Gln Leu Gly Leu
465                 470                 475                 480

Gly Pro Leu Gly Pro Ile Gly Leu Pro Gly Pro Gly Pro Leu Pro Ser
                485                 490                 495

Leu Pro Ala Gly Leu Pro Leu Asn Pro Met Ala Asn Gly Leu Gln Gln
            500                 505                 510

Met Ala Ala Ala Asn Leu Met Gln Gly Met Ala Gly Met Gly Gln Leu
            515                 520                 525

Pro Ala Leu Ser Met Asn Gly Met Asn Gly Ile Met Gly Pro Leu Pro
530                 535                 540

Gly Val Gly Leu Pro Gly Pro Gln Gln His Leu Phe Pro Gln Gln Gln
545                 550                 555                 560

Gln Pro His Leu Gln Gln Gln Gln Gln Gln Gln Gln Lys Asp Leu
                565                 570                 575

Gln Met Ala Gln Lys Gln His Gln Ala Ala Ala Ala Ala Ala Val
            580                 585                 590

Ala Ala Ala Val Ala Ala Ala Gln His Gln Gln Gln Pro Gln Ala
        595                 600                 605

Gln Gln Gln Pro Gln Pro Gln Gln Gln Gln Pro Gly Lys Leu
    610                 615                 620

Pro Gln Ala Thr Val Gly Thr Pro Ala Leu Ala Ser Pro Ala Gly Ala
625                 630                 635                 640

Leu Pro Arg Gln Pro Ser Gly Gln His Pro His Thr Leu Ser Ser Ser
                645                 650                 655

Ser Leu His Thr Gln Gln Pro His Gln Gln Leu Leu His Ser Gln
            660                 665                 670

Pro Ser Ser Thr His Leu Ala Thr Asn Asn Thr Leu Ala Met Ala Pro
            675                 680                 685

Ala Leu Asn Gly Thr Leu Asp Val Gly Gly Lys Gly His Leu His Ala
        690                 695                 700
```

```
Ala Gly Gly Gln Gly Ala Gly Ala Gly Ala Val Leu Asp Ile
705             710             715             720

Pro Pro Asp Leu Ile Gly Gly Leu Ile Glu Asp Gly Phe Gly Ala Pro
            725             730             735

Pro Gly Pro Thr Ile Gln Leu Ala His Gly Thr Ala Ala Val Leu Asp
            740             745             750

Pro Thr Met Leu Leu Asp Glu Gly Asp Asn Ser Asp Phe Ala Ala Val
            755             760             765

Phe Gln Glu Met Ser Ser Tyr Gly Gly Gly Val Ile Gly Gly Gly
            770             775             780

Gly Ser Gly Ala Gly Ala Met Gly Val Leu Gly His Gly Leu Leu Ala
785             790             795             800

Ala Gly Gly Pro Val Met Val Asp Val Ala Ala Gly Leu Ala Gly Val
            805             810             815

Thr Glu Thr Ala Thr Arg Val Asp Asp Asp Phe Leu Asn Phe Leu Leu
            820             825             830

<210> SEQ ID NO 14
<211> LENGTH: 446
<212> TYPE: PRT
<213> ORGANISM: Tetraselmis sp.
<220> FEATURE:
<221> NAME/KEY: misc_feature
<223> OTHER INFORMATION: SGI1 polypeptide 5172

<400> SEQUENCE: 14

Met Ser Cys Thr Val Ala Ser Phe Pro Pro Ala Gly Gly Gln Gly
1               5               10              15

Ser Pro Ala Thr Pro Val Pro Tyr Gln Asp Leu Leu Val Lys Arg Gln
            20              25              30

Asp Gln Trp Ser Asn Phe Pro Ala Gly Leu Arg Val Leu Val Ala Asp
        35              40                  45

Asn Asp Pro Ala Ser Leu Gln Gln Val Glu Lys Met Leu Lys Lys Cys
50              55                  60

Ser Tyr Gln Val Thr Leu Cys Ser Ser Gly Lys Asn Ser Leu Glu Ile
65              70              75                  80

Leu Arg Lys Arg Arg Glu Glu Phe Asp Leu Val Leu Ala Asp Ala Asn
            85              90                  95

Leu Pro Asp Ile Asp Gly Phe Lys Leu Leu His Val Cys His Thr Glu
            100             105             110

Leu Ser Leu Pro Val Val Leu Met Ser Gly Thr Ser Asp Thr Gln Leu
            115             120             125

Val Met Arg Gly Val Met Asp Gly Ala Arg Asp Phe Leu Ile Lys Pro
130             135             140

Leu Arg Val Glu Glu Leu Lys Val Leu Trp Gln His Leu Val Arg Phe
145             150             155             160

Thr Ser Glu Ile Thr Lys Thr Asp Ala Gln Leu Asn Val Val Lys Val
            165             170             175

Glu Leu Asp Gly Gly Arg Pro Ala Gly Glu Val Ser Thr Ser Gln Asn
            180             185             190

Gly Ser Gln Cys Thr Glu Arg Glu Gly Glu Gly Asn Ser Ser Lys Lys
            195             200             205

Gln Arg Met Asn Trp Ser Asp Glu Met His Gln Gln Phe Val Asn Ala
            210             215             220

Val Asn Gln Leu Gly Ile Asp Lys Ala Val Pro Lys Arg Ile Leu Asp
225             230             235             240
```

```
Leu Met Ser Val Glu Gly Leu Thr Arg Glu Asn Val Ala Ser His Leu
                245                 250                 255

Gln Lys Tyr Arg Ile Tyr Leu Lys Arg Met Ala Asn His Gln Glu Asn
            260                 265                 270

Gly Lys Gln Ala Val Met Ser Thr Asp Thr Ile Ala Arg Ala Glu Ala
        275                 280                 285

Ala Tyr Gln Gly Gly Met Pro Gln Gly Gln Gln Met Met Gln Gln Glu
    290                 295                 300

His Ser Gly Gln Ala Val Gln Tyr Ser Gln Pro His Ala Pro Gly Gly
305                 310                 315                 320

Leu His Gln Gln Ala Met Pro Ala Gln Met His Met Gly Met Met Pro
                325                 330                 335

Ala Gly Pro Gln Pro Gly Ser Met Gln Met Ala Pro His His Val Met
            340                 345                 350

Gln Met Pro Asn Gly Gln Val Met Val Met Gln Met Gly Pro Arg
        355                 360                 365

Pro Gly Met Pro Pro Gly Met Pro Gln Gln Met Met Ala Ser Ser Gln
    370                 375                 380

Gln Met Gly Met Leu Gln Pro Gly Met Pro Ala Gly Gln Met Leu His
385                 390                 395                 400

Phe Gln His Pro Gln Gln Val His Gln His Pro Pro Ser Ser Gly Pro
                405                 410                 415

Met His Ala Val Gln His Met Glu Tyr Ala Tyr Ser Gln Pro Met Gln
            420                 425                 430

Met Ala Gly Trp Pro Val Gln Gly Gln Pro Gly Asn Gln Ala
        435                 440                 445

<210> SEQ ID NO 15
<211> LENGTH: 490
<212> TYPE: PRT
<213> ORGANISM: Tetraselmis sp.
<220> FEATURE:
<221> NAME/KEY: misc_feature
<223> OTHER INFORMATION: SGI1 polypeptide 5185

<400> SEQUENCE: 15

Met Thr Pro Thr Pro Pro Met Ser Cys Thr Val Ala Ser Phe Pro Pro
1               5                   10                  15

Ala Ala Gly Gly Gln Gly Ser Pro Ala Thr Pro Val Pro Tyr Gln Asp
            20                  25                  30

Leu Leu Val Lys Arg Gln Asp Gln Trp Ser Asn Phe Pro Ala Gly Leu
        35                  40                  45

Arg Val Leu Val Ala Asp Asn Asp Pro Ala Ser Leu Gln Gln Val Glu
    50                  55                  60

Lys Met Leu Lys Lys Cys Ser Tyr Gln Val Thr Leu Cys Ser Ser Gly
65                  70                  75                  80

Lys Asn Ser Leu Glu Ile Leu Arg Lys Arg Glu Glu Phe Asp Leu
                85                  90                  95

Val Leu Ala Asp Ala Asn Leu Pro Asp Ile Asp Gly Phe Lys Leu Leu
            100                 105                 110

His Val Cys His Thr Glu Leu Ser Leu Pro Val Val Leu Met Ser Gly
        115                 120                 125

Thr Ser Asp Thr Gln Leu Val Met Arg Gly Val Met Asp Gly Ala Arg
    130                 135                 140

Asp Phe Leu Ile Lys Pro Leu Arg Val Glu Glu Leu Lys Val Leu Trp
```

```
            145                 150                 155                 160
        Gln His Leu Val Arg Phe Thr Ser Glu Ile Thr Lys Thr Asp Ala Gln
                        165                 170                 175

Leu Asn Val Val Lys Val Glu Leu Asp Gly Gly Arg Pro Ala Gly Glu
                        180                 185                 190

Val Ser Thr Ser Gln Asn Gly Ser Gln Cys Thr Glu Arg Glu Gly Glu
                        195                 200                 205

Gly Asn Ser Ser Lys Lys Gln Arg Met Asn Trp Ser Asp Glu Met His
        210                 215                 220

Gln Gln Phe Val Asn Ala Val Asn Gln Leu Gly Ile Asp Lys Ala Val
        225                 230                 235                 240

Pro Lys Arg Ile Leu Asp Leu Met Ser Val Glu Gly Leu Thr Arg Glu
                        245                 250                 255

Asn Val Ala Ser His Leu Gln Lys Tyr Arg Ile Tyr Leu Lys Arg Met
                        260                 265                 270

Ala Asn His Gln Glu Asn Gly Lys Gln Ala Val Met Ser Thr Asp Thr
                        275                 280                 285

Ile Ala Arg Ala Glu Ala Ala Tyr Gln Gly Gly Met Pro Gln Gly Gln
                        290                 295                 300

Gln Met Met Gln Gln Glu His Ser Gly Gln Ala Val Gln Tyr Ser Gln
        305                 310                 315                 320

Pro His Ala Pro Gly Gly Leu His Gln Gln Ala Met Pro Ala Gln Met
                        325                 330                 335

His Met Gly Met Met Pro Ala Gly Pro Gln Pro Gly Ser Met Gln Met
                        340                 345                 350

Ala Pro His His Val Met Gln Met Pro Asn Gly Gln Val Met Val Met
                        355                 360                 365

Gln Gln Met Gly Pro Arg Pro Gly Met Pro Pro Gly Met Pro Gln Gln
                        370                 375                 380

Met Met Ala Ser Ser Gln Gln Met Gly Met Leu Gln Pro Gly Met Pro
        385                 390                 395                 400

Ala Gly Gln Met Leu His Phe Gln His Pro Gln Gln Val His Gln His
                        405                 410                 415

Pro Pro Ser Ser Gly Pro Met His Ala Gly Gly Glu Met Ile Asp Pro
                        420                 425                 430

Gly Ser Met Gln Arg Leu His Gln Gln Pro His Tyr Ile Gly Pro Asn
                        435                 440                 445

Gly Gln His Met Pro Ala Pro Ala Met Gly Met Pro Ser Gly Thr Val
                        450                 455                 460

Gln His Met Glu Tyr Ala Tyr Ser Gln Pro Met Gln Met Ala Gly Trp
        465                 470                 475                 480

Pro Val Gln Gly Gln Pro Gly Asn Gln Ala
                        485                 490

<210> SEQ ID NO 16
<211> LENGTH: 574
<212> TYPE: PRT
<213> ORGANISM: Tetraselmis sp.
<220> FEATURE:
<221> NAME/KEY: misc_feature
<223> OTHER INFORMATION: SGI1 polypeptide 5230

<400> SEQUENCE: 16

Met Thr Met Pro Leu Gly Gly Gly Leu Cys Met Lys Asp Arg Ile His
1               5                   10                  15
```

```
Gly Asp Glu Arg Tyr Arg Ser Lys Ala Lys Arg Gln Val Asn Thr Ile
             20                  25                  30
Phe Ala Phe Thr Gln Arg Asn Thr Trp Arg Gly Arg Phe Arg Leu Cys
         35                  40                  45
Ser Tyr Arg Thr Thr Glu Leu Leu Gly Gly Ser Lys Thr Thr Glu Pro
     50                  55                  60
Gly Arg Gly Thr Phe Val Leu Gln Ile Phe Met Cys Val Lys Asn Ala
 65                  70                  75                  80
Ser Ile Asp Asp Gly Ser Arg His Ile Ser Thr Ser Arg Gly Leu Glu
                 85                  90                  95
Ser Val Leu Lys Arg Arg Gly Gln Gly Ala Pro Ala Ala Pro Val
             100                 105                 110
Pro Tyr His Asp Leu Leu Val Lys Arg Gln Asp Gln Trp Ser Asn Phe
         115                 120                 125
Pro Ala Gly Leu Arg Val Leu Val Ala Asp Asn Asp Pro Ala Ser Leu
     130                 135                 140
Gln Gln Val Glu Lys Met Leu Lys Lys Cys Ser Tyr Gln Val Thr Leu
145                 150                 155                 160
Cys Ser Ser Gly Lys Asn Ser Leu Glu Ile Leu Arg Lys Arg Arg Glu
                 165                 170                 175
Glu Phe Asp Leu Val Leu Ala Asp Ala Asn Leu Pro Asp Ile Asp Gly
             180                 185                 190
Phe Lys Leu Leu His Val Cys His Thr Glu Leu Ser Leu Pro Val Val
         195                 200                 205
Leu Met Ser Gly Thr Ser Asp Thr Gln Leu Val Met Arg Gly Val Met
210                 215                 220
Asp Gly Ala Arg Asp Phe Leu Ile Lys Pro Leu Arg Val Glu Glu Leu
225                 230                 235                 240
Lys Val Leu Trp Gln His Leu Val Arg Phe Thr Ser Glu Ile Thr Lys
             245                 250                 255
Thr Asp Ala Gln Leu Asn Val Val Lys Val Glu Leu Asp Ser Gly Arg
         260                 265                 270
Pro Ala Gly Glu Val Ser Thr Ser Gln Asn Gly Ser Gln Cys Ala Glu
     275                 280                 285
Arg Glu Gly Glu Gly Asn Ser Ser Lys Lys Gln Arg Met Asn Trp Ser
 290                 295                 300
Asp Glu Met His Gln Gln Phe Val Asn Ala Val Asn Gln Leu Gly Ile
305                 310                 315                 320
Asp Lys Ala Val Pro Lys Arg Ile Leu Asp Leu Met Ser Val Glu Gly
             325                 330                 335
Leu Thr Arg Glu Asn Val Ala Ser His Leu Gln Lys Tyr Arg Ile Tyr
         340                 345                 350
Leu Lys Arg Met Ala Asn His Gln Glu Asn Gly Lys Gln Ala Val Met
     355                 360                 365
Ser Thr Asp Thr Ile Ala Arg Ala Glu Ala Tyr Gln Gly Gly Met
 370                 375                 380
Pro Gln Gly Gln Gln Met Met Gln Gln Glu His Ser Gly Gln Ala Val
385                 390                 395                 400
Gln Tyr Ser Gln Pro His Ala Pro Ser Gly Leu His Gln Ala Met
             405                 410                 415
Pro Ala Gln Met His Met Gly Met Met Pro Ala Gly Pro Gln Pro Gly
         420                 425                 430
Ser Met Gln Met Ala Pro His His Val Met Gln Met Pro Asn Gly Gln
```

```
                435                 440                 445
Val Met Val Met Gln Met Gly Pro Arg Pro Gly Met Pro Gly
    450                 455                 460

Met Pro Gln Met Met Ala Ser Ser Gln Gln Met Gly Met Leu Gln
465                 470                 475                 480

Pro Gly Met Pro Ala Gly Gln Met Leu His Phe Gln His Pro Gln Gln
                485                 490                 495

Val His Gln His Pro Ser Ser Gly Pro Met His Ala Gly Gly Glu
                500                 505                 510

Met Ile Asp Pro Gly Ser Met Gln Arg Leu His Gln Gln Pro His Tyr
            515                 520                 525

Ile Val Pro Asn Ala Gln His Met Pro Ala Pro Ala Met Gly Met Pro
        530                 535                 540

Pro Gly Ala Val Gln His Met Glu Tyr Ala Tyr Ser Gln Pro Met Gln
545                 550                 555                 560

Met Ala Gly Trp Pro Val Gln Gly Gln Pro Gly Ser Gln Ala
                565                 570
```

<210> SEQ ID NO 17
<211> LENGTH: 674
<212> TYPE: PRT
<213> ORGANISM: Oocystis sp.
<220> FEATURE:
<221> NAME/KEY: misc_feature
<223> OTHER INFORMATION: SGI1 polypeptide 5549

<400> SEQUENCE: 17

```
Met Leu Ala Phe Thr His Gln Arg Met Thr Thr Ala Pro Ala Leu Ala
1               5                   10                  15

Val Ala Thr Ser His Phe Phe Ala His Val Arg Val Thr Thr Gly Ser
            20                  25                  30

Ser Ala Ile Ala Thr Val Phe Ala Ala Arg Ser Arg Gly Ser Gly Leu
        35                  40                  45

Leu Ala Gly Phe Asn Thr Met Glu Asn Val Lys Val Glu Val Pro Glu
    50                  55                  60

Val Val Pro Glu Asn Val Asn Phe Pro Ala Gly Leu Lys Val Leu Val
65                  70                  75                  80

Val Asp Asp Asp Pro Leu Cys Leu Lys Val Ile Asp Gln Met Leu Arg
                85                  90                  95

Arg Cys Asn Tyr Ala Ala Thr Thr Cys Gln Ser Ser Leu Glu Ala Leu
            100                 105                 110

Glu Leu Leu Arg Ser Ser Lys Glu Asn His Phe Asp Leu Val Leu Ser
        115                 120                 125

Asp Val Tyr Met Pro Asp Met Asp Gly Phe Lys Leu Leu Glu Ile Ile
    130                 135                 140

Gly Leu Glu Met Gly Leu Pro Val Ile Met Met Ser Ser Asn Gly Glu
145                 150                 155                 160

Thr Gly Val Val Phe Arg Gly Val Thr His Gly Ala Val Asp Phe Leu
                165                 170                 175

Ile Lys Pro Val Arg Ile Glu Glu Leu Arg Asn Leu Trp Gln His Val
            180                 185                 190

Val Arg Lys Thr Met Val Val Pro Ser Asn Asp Lys Ala Thr Ser Glu
        195                 200                 205

Glu Asp Gly Glu Glu Ser Lys His Arg Val Asp Arg Lys Arg Lys Glu
    210                 215                 220
```

-continued

```
Ser Phe His Ser Arg Ala Arg Glu Gln Val Glu Ile Ala Cys Ser Val
225                 230                 235                 240

Val Pro Ala Leu Leu Trp Pro Thr Val Pro Pro Ser Ser Val His Pro
            245                 250                 255

Thr Ser Ser Ser Phe Leu Arg Ser His Val Leu Leu Leu Gln Arg Ser
        260                 265                 270

Ser Gly Gly Lys Asp Val Leu Asp Glu Gly Gly Ser Asn Ala Lys Lys
    275                 280                 285

Pro Arg Val Val Trp Ser Val Glu Met His Gln Gln Phe Val Asn Ala
290                 295                 300

Val Asn Gln Leu Gly Ile Asp Lys Ala Val Pro Lys Arg Ile Leu Asp
305                 310                 315                 320

Leu Met Asn Val Asp Gly Leu Thr Arg Glu Asn Val Ala Ser His Leu
                325                 330                 335

Gln Lys Tyr Arg Leu Tyr Leu Lys Arg Val Ala Gly Ile Asn Thr Ala
            340                 345                 350

Thr Gly Ser Arg Asn Gly Lys Gly Arg Ser Asp Val Ser Gly Leu Ser
        355                 360                 365

Gly Met Pro Asn Gly Ser Leu Pro Met Pro Gly Met Met Pro Pro His
    370                 375                 380

Met Ala Ala Gly Met Leu Leu Ala Gly Met Ala Ala Asp Val Gly Pro
385                 390                 395                 400

Arg Pro His Pro Phe Pro Ile Met Pro Met Pro Ala Met Ala Leu Gln
                405                 410                 415

Gly Met His Gly Gly Met Ala Gln Met Met Gln Leu Pro Pro Gly Met
            420                 425                 430

Pro Pro Pro Met Met Met Pro Met Ala Pro Leu Leu Pro Ser Gln Leu
        435                 440                 445

Ala Ala Leu Gly Gln Gln Gln Gln Gln Gln Gln Gln Gln Gln Val Ala
    450                 455                 460

Arg Ser Glu Ser Met Pro Ser Glu Asn Gly Val Ala Gly Pro Ser Gly
465                 470                 475                 480

Ser Phe Thr Ala Met Leu Asn Gly Pro Ala Pro Met Glu Ser Ser Pro
                485                 490                 495

Phe Ala Ala Leu Gln Val Phe Gly Pro Pro Gln Gly Met Glu Gln Leu
            500                 505                 510

Thr Gln Gln Gln Gln Gln Gln Gln Ala Gly Ala Ala Ala Phe Val
        515                 520                 525

Ala Ala Phe Ala Ala Asn Gly Gly Asp Met Gln Gly Gly Gly Gly
    530                 535                 540

Gly Pro Gly Pro Met Leu Gly Gly Ala Gly Gly Ala Gly Pro Leu Leu
545                 550                 555                 560

Gly Gly Val Gly Gly Gly Asp Pro Leu His Gly Gly Gly Gly Ser Ser
                565                 570                 575

Ala Leu Gly Gly Arg Pro Met Met Ser Ala Glu Gln Pro Met Gly Gly
            580                 585                 590

Ser Gly Gly Leu Ala Ser Asn Ser Leu Thr Val Gln Gln Asn Asp Leu
        595                 600                 605

Ala Gln Met Cys Ser Gln Leu Asp Val Asn Gly Leu Gln Ala Val Ala
    610                 615                 620

Ala Ala Ala Ala Ala Gly Ala Met Gly Ala Pro Gly Gly Ala Gly Gly
625                 630                 635                 640

Ala Met Pro Pro Ser Ser Val Gly Gly Val Gly Pro Asp Met Lys Leu
```

```
                    645                 650                 655
Thr Glu Gln Asp Asp Phe Phe Ser Phe Leu Leu Lys Asp Ser Asn Leu
                660                 665                 670

Ile Asp

<210> SEQ ID NO 18
<211> LENGTH: 488
<212> TYPE: PRT
<213> ORGANISM: Micromonas sp.
<220> FEATURE:
<221> NAME/KEY: misc_feature
<223> OTHER INFORMATION: RCC299, SGI1 polypeptide

<400> SEQUENCE: 18

Met Ser Thr Pro Ala Val Ser Lys Gly Phe Pro Ile Gly Leu Arg Val
1               5                   10                  15

Leu Val Val Asp Asp Pro Leu Cys Leu Lys Ile Val Glu Lys Met
            20                  25                  30

Leu Lys Arg Cys Gln Tyr Glu Val Thr Thr Phe Ser Arg Gly Ala Glu
        35                  40                  45

Ala Leu Lys Thr Leu Arg Glu Arg Lys Asp Asp Phe Asp Ile Val Leu
    50                  55                  60

Ser Asp Val His Met Pro Asp Met Asp Gly Phe Lys Leu Leu Glu His
65                  70                  75                  80

Ile Ala Leu Glu Leu Asp Ile Pro Val Met Met Ser Ala Asn Cys
                85                  90                  95

Ala Thr Asp Val Val Leu Arg Gly Ile Ile His Gly Ala Val Asp Tyr
            100                 105                 110

Leu Leu Lys Pro Val Arg Ile Glu Glu Leu Arg Asn Ile Trp Gln His
        115                 120                 125

Val Val Arg Arg Lys Arg Glu Ser Ser Gln Gly Asn Leu Arg Ser Gly
130                 135                 140

Glu Gly Gly Ser Asn Gly Arg Thr Val Ser Gly Gly Ser Thr Gly Glu
145                 150                 155                 160

Gly Gly Gly Lys Asp Ser Lys Gly Ser Ser Glu Gln His Gly Asp Ala
                165                 170                 175

Lys Asp Lys Thr Gly Ser Ala Gly Gly Ser Gly Gly Ser Ser Lys Arg
            180                 185                 190

Lys Lys Gly Ser Gly Lys Lys Gly Asp Glu Gly Thr Asp Glu Val Lys
        195                 200                 205

Asp Gly Ser Gly Gly Asp Glu Asn Glu Asp Ser Ser Ala Leu Lys Lys
210                 215                 220

Pro Arg Val Val Trp Ser Ala Glu Leu His Gln Gln Phe Val Thr Ala
225                 230                 235                 240

Val Asn Gln Leu Gly Ile Asp Lys Ala Val Pro Lys Arg Ile Leu Asp
                245                 250                 255

Leu Met Gly Val Gln Gly Leu Thr Arg Glu Asn Val Ala Ser His Leu
            260                 265                 270

Gln Lys Tyr Arg Leu Tyr Leu Lys Arg Leu Gln Gly Val Asn Ser Gly
        275                 280                 285

Gly Ala Pro Gly Gly Gly Pro Gly Phe Met Ser Pro Ile Ala Leu Asp
    290                 295                 300

Gly Ser Met Val Gln Gly Gly Pro Gly Gly Arg Val Gly Ser Pro Ala
305                 310                 315                 320

Ile Gly Gly Pro Asn Gly Pro Ile Met Val Gly His Gly His Ile Asp
```

```
                    325                 330                 335
Pro Ala Met Leu Ala Gly Gly Ala Pro Gln Thr Ile Gln Met Gly Met
                340                 345                 350

Val Tyr Gly Gly Pro Gly Met Gly Pro Pro Gln Met Met Ala Pro Asn
            355                 360                 365

Gly Lys Gly Gly Gly Met Pro Gly Gly Tyr Val Met Gln Pro Gly
    370                 375                 380

Gln Met Met Ala Pro Asn Gly Gln Met Met Pro Val Gly Gln Met Gly
385                 390                 395                 400

Pro Gly Gly Met Met Val Gln Gly Pro Gly Gly Met Met Gln Met
            405                 410                 415

His Asp Gly Gly Met Met Asn Gly Asn Gly Ser Tyr Gly Ser Leu Gln
            420                 425                 430

Asn Met Lys Gln Gly Asn Gly Val Val Met Met Pro Asn Gly Gly Met
            435                 440                 445

Gly Gly Val Asp Gly Ala Ile Pro Asn Met Ala Thr Gly Leu Ile Asn
    450                 455                 460

Gly Gln Gly Leu Pro Asp Asp Val Leu Asp Met Phe Leu Lys Asp
465                 470                 475                 480

Gly Leu Pro Glu Gly Glu Gly Phe
                485

<210> SEQ ID NO 19
<211> LENGTH: 544
<212> TYPE: PRT
<213> ORGANISM: Micromonas pusilla
<220> FEATURE:
<221> NAME/KEY: misc_feature
<223> OTHER INFORMATION: SGI1 polypeptide

<400> SEQUENCE: 19

Met Thr Ala Glu Lys Lys Glu Leu Lys Val Phe Pro Ala Gly Leu Arg
1               5                   10                  15

Val Leu Val Val Asp Asp Asp Pro Leu Cys Leu Arg Ile Val Glu Lys
            20                  25                  30

Met Leu Lys Arg Cys Gln Tyr Glu Val Thr Thr Phe Ser Arg Gly Ala
        35                  40                  45

Glu Ala Leu Glu Thr Leu Arg Ala Arg Arg Asp Asp Phe Asp Ile Val
    50                  55                  60

Leu Ser Asp Val His Met Pro Asp Met Asp Gly Phe Lys Leu Leu Glu
65                  70                  75                  80

His Ile Ala Leu Glu Leu Asp Val Pro Val Met Met Ser Ala Asn
            85                  90                  95

Cys Ala Thr Asp Val Val Leu Arg Gly Ile Ile His Gly Ala Val Asp
            100                 105                 110

Tyr Leu Leu Lys Pro Val Arg Leu Glu Glu Leu Arg Asn Ile Trp Gln
        115                 120                 125

His Val Val Arg Arg Gln Arg Glu Pro Ser Lys Asp Gly Ala Ala Gly
    130                 135                 140

Lys Gly Gly Gly Ala Ser Gly Ala Pro Glu Val Ser Gly Asp Thr His
145                 150                 155                 160

Ala Asn Thr Asp Asp Lys Gln Asp Gly Asn Ala Thr Asp Ser Lys Gly
            165                 170                 175

Ser Gly Ser Gln Lys Arg Lys Ser Gly Lys Ser Gly Asp Asp Gly Gly
        180                 185                 190
```

```
Lys Asp Gly Gly Gly Ser Gly Lys Asp Gly Asp Ala Ser Asn Lys
            195                 200                 205

Gly Asn Asn Lys Arg Lys Lys Gly Lys Ser Asn Asp Ala Thr Glu
210                 215                 220

Thr Ala Gly Gly Ala Gly Val Glu Asp Asn Asp Asp Thr Ser Gly Leu
225                 230                 235                 240

Lys Lys Pro Arg Val Val Trp Ser Pro Glu Leu His Gln Gln Phe Val
                245                 250                 255

Thr Ala Val Asn Gln Leu Gly Ile Asp Lys Ala Val Pro Lys Arg Ile
                260                 265                 270

Leu Asp Leu Met Gly Val Gln Gly Leu Thr Arg Glu Asn Val Ala Ser
            275                 280                 285

His Leu Gln Lys Tyr Arg Leu Tyr Leu Lys Arg Leu Gln Gly Val Asn
        290                 295                 300

Asn Asn Gly Thr Val Pro Ser Gly Ala Ala Gly Phe Met Thr Gly Leu
305                 310                 315                 320

Ala Ile Asp Gly Val Gly Gly Val Met Gly Pro Pro Thr Thr Gly Ser
                325                 330                 335

Pro Ala Met Asn Gly Pro Gly Gly Pro Gly Gly Gly Leu Val Met Gly
                340                 345                 350

Pro Gly His Met Gly Gly Pro His Met Asp Gly Ser Gly Met Met His
            355                 360                 365

Met Gly Pro Gly Gly Pro Met Ala Gly Met Thr Val Val Tyr Gly Gly
        370                 375                 380

Gly Met Pro Gly Gly Met Pro Gly Gly Ala Asp Ser Lys Asn Gly Ala
385                 390                 395                 400

Ser Gly Gln Pro Pro Pro Gly Gly Tyr Val Val Met Gly Gly Pro His
                405                 410                 415

Gly Gly Gly Pro Gly Gly Ala Pro Met Met Met Gln His Gly Gly Met
                420                 425                 430

Val Pro Gly Pro Gly Pro Gly Leu Val Pro Gly Pro Gly Gly Ser Leu
            435                 440                 445

Met Met Pro Ala Gly Met Met Pro Asp Gly Gly Gly Met Val Gly
        450                 455                 460

Val His Val Gly Pro Gly Val Met Gly Gln His Gln Leu Gly Gly
465                 470                 475                 480

Lys His Ser Ser Gly Ala Gly Met Ala Gly Gly Ser Ala Ala Gly
                485                 490                 495

Lys Gly Ala Gln Arg Gly Gly Val Gly Gly Ala Phe Asp Val Pro Pro
            500                 505                 510

Thr Asn Gly Ser Leu Asp Ala Asp Glu Ile Gly Asp Asp Val Leu Thr
            515                 520                 525

Met Phe Leu Lys Asp Gly Leu Pro Glu Met Asn Asp Gly Asp Ala Leu
        530                 535                 540
```

<210> SEQ ID NO 20
<211> LENGTH: 776
<212> TYPE: PRT
<213> ORGANISM: Sphagnum fallax
<220> FEATURE:
<221> NAME/KEY: misc_feature
<223> OTHER INFORMATION: SGI1 polypeptide

<400> SEQUENCE: 20

```
Met Ser Gly Gly Asp Leu Ser Arg Val Arg Glu Gly Thr Ala Asp Leu
1               5                   10                  15
```

Asp Pro Val Met Ala Ser His Gln His Pro Pro Arg Gln Gln Ser
            20                  25                  30

His Gln Gln Pro Lys Asn His Gln Gln Glu Ala His Gln Gln His Cys
        35                  40                  45

Ser Ser Ala Glu Thr Thr Ser Pro Asn Asn Thr Ala Arg Gly Ala Gly
50                  55                  60

Ala Thr Tyr Gly Lys Met Glu Pro Ala Asp Asp Phe Pro Ala Gly Leu
65                  70                  75                  80

Arg Ile Leu Val Val Asp Asp Pro Thr Cys Leu Ala Ile Leu Lys
                85                  90                  95

Lys Met Leu Gln Gln Cys Ser Tyr Gln Val Thr Thr Cys Gly Arg Ala
            100                 105                 110

Thr Arg Ala Leu Glu Leu Leu Arg Glu Asp Lys Asp Lys Phe Asp Leu
        115                 120                 125

Val Ile Ser Asp Val Tyr Met Pro Asp Met Asp Gly Phe Lys Leu Leu
130                 135                 140

Glu Leu Val Gly Leu Glu Met Asp Leu Pro Val Ile Met Met Ser Gly
145                 150                 155                 160

Asn Gly Glu Thr Ser Val Val Met Lys Gly Ile Thr His Gly Ala Cys
            165                 170                 175

Asp Tyr Leu Leu Lys Pro Val Arg Ile Glu Glu Leu Ser Asn Ile Trp
        180                 185                 190

Gln His Val Val Arg Lys Leu Arg Ser Glu Pro Lys Glu His Ser Ala
    195                 200                 205

Ser Leu Glu Asp Gly Asp Arg Gln Arg Arg Gly Ala Glu Asp Ala
210                 215                 220

Asp Asn Thr Ser Ser Ala Ala Asp Thr Ala Asp Gly Ile Trp Arg Asn
225                 230                 235                 240

Lys Lys Lys Lys Glu Ala Lys Glu Asp Glu Glu Asp Phe Glu Gln Asp
            245                 250                 255

Asn Asp Asp Pro Ser Thr Leu Lys Lys Pro Arg Val Val Trp Ser Val
        260                 265                 270

Glu Leu His Gln Gln Phe Val Ser Ala Val Asn Gln Leu Gly Ile Asp
    275                 280                 285

Lys Ala Val Pro Lys Arg Ile Leu Glu Leu Met Ser Val Gln Gly Leu
290                 295                 300

Thr Arg Glu Asn Val Ala Ser His Leu Gln Lys Tyr Arg Leu Tyr Leu
305                 310                 315                 320

Lys Arg Leu Ser Gly Val Thr Ser Gln Ser Asn Ser Leu Asn Val Ser
            325                 330                 335

Phe Gly Gly Pro Asp Ala Gly Tyr Gly Gly Leu Phe Gly Leu Asp Glu
        340                 345                 350

Met Ser Asp Tyr Arg Asn Leu Val Thr Asn Gly His Leu Pro Ala Gln
    355                 360                 365

Thr Ile Ala Ala Leu His His Ala Asn Met Ala Gly Arg Leu Gly Ala
370                 375                 380

Ser Ser Gly Met Val Gly Pro Ser Ser Pro Leu Asp Pro Ser Val Leu
385                 390                 395                 400

Ala Gln Ile Ala Ala Leu Gln Ser Gly Ser Leu Pro Arg Pro Gly Met
            405                 410                 415

Asp Gly Ser Leu Gln Gly Asn Gln Ala Gly Leu Leu Gln Ser Leu Ser
        420                 425                 430

Gly Ala Leu Asp Tyr Asn Ser Leu His Gln Ser His Leu Pro Ala
            435                 440                 445

Ile Gly Gln Leu Gly Gln Leu Asp Glu Leu Pro Ser Leu Lys Ser Met
    450                 455                 460

Gln His Gln Leu Gly Met Gly Ser Leu Gly Gly Ser Thr Arg Asn Leu
465                 470                 475                 480

Ala Gly Ser Pro Asn Glu Glu Leu Thr Met Gln Leu Gln Gln Arg
                485                 490                 495

Ala Gln Gln Gln Ser Gly Gly Ser Pro Ile Asn Leu Pro Gln Ala Thr
                500                 505                 510

Gly Ile Leu Arg Pro Leu Ser Ser Asn Ile Asn Gln Gly Gly Ser Val
            515                 520                 525

Pro Asn Leu Val Gly Val Ile Pro Gly Thr Ala Ile Gly Leu Ser Asn
            530                 535                 540

Met Cys Ser Gly Gly Arg Glu Phe Gly Ser Ser Ser Gly Leu Leu Ser
545                 550                 555                 560

Ala Ser Gly Ser Leu Met Gln Ser Ser Thr Val Glu Ala Gln Asn Leu
                565                 570                 575

Asn Phe Gly Gly Ser Ser Gly Ser Ser Gly Cys Ser Phe Gln Ala Ser
            580                 585                 590

Val Leu Ser Ser Lys Thr Gly Gly Leu Glu Asp Leu Asn Pro Ala Lys
            595                 600                 605

Arg Val Arg Thr Thr Tyr Ser Ala Leu Ser His Ser Ser Pro Asp Leu
    610                 615                 620

Gly Gln Ser Ser Arg Pro Ala Trp Leu Gly Ser Gln Glu Gly Leu Val
625                 630                 635                 640

His Gly Asp Pro Val Tyr Ser Pro His Gln Leu Ser Leu Pro Arg Gln
                645                 650                 655

Asp Ile Val Gly Gly Ile Gly Ser Ser Gly Arg Pro Ala Tyr Met Gly
            660                 665                 670

Ser Gln Ser Met Gly Ser Leu Gly Met Asn Phe Pro Leu Ser Leu Ala
            675                 680                 685

Val Asp Ala Gly Ala Val Arg Pro Ser Leu Thr Arg Gly Gln Ser Leu
690                 695                 700

Thr Glu Gln Val Ala Ala Asn Arg Glu Leu Lys Phe Pro Lys Glu Glu
705                 710                 715                 720

Arg Gly Arg Asp Asn Leu Met Cys Ala Arg Leu Gly Gly Gly Met Ile
                725                 730                 735

Thr Asn Glu Ser Ser Ser Glu Glu Leu Leu Asn Tyr Leu Lys Gln Ser
            740                 745                 750

His Glu Gly Leu Gly Phe Met Glu Gly Asp Leu Val Ser Asp Gly Tyr
            755                 760                 765

Pro Val Asp Asn Leu Tyr Val Lys
770                 775

<210> SEQ ID NO 21
<211> LENGTH: 715
<212> TYPE: PRT
<213> ORGANISM: Physcomitrella patens
<220> FEATURE:
<221> NAME/KEY: misc_feature
<223> OTHER INFORMATION: SGI1 polypeptid

<400> SEQUENCE: 21

Met Gly Gly Gly Tyr Leu Ser Ser Thr Val Asn Met Gly Glu Ser Arg
1               5                   10                  15

```
Asp Gly Gly Ser Pro Ala Met Ala Thr Leu Gln Gln Gln Lys His
            20                  25                  30

Gln Pro Leu Asn Pro Asn His Gln Asn Pro Arg Asn Arg Ser Asn Ser
             35                  40                  45

Ser Pro Thr Asn Cys Tyr Ser Asn Thr Ala Trp Gly Ala Lys Pro Ala
 50                  55                  60

Lys Leu Asp Thr Pro Asp Glu Phe Pro Val Gly Met Arg Val Leu Val
 65                  70                  75                  80

Val Asp Asp Asn Pro Thr Cys Leu Met Ile Leu Glu Gln Met Leu Val
                 85                  90                  95

Arg Cys Ala Tyr Arg Val Thr Thr Cys Gly Lys Ala Thr Glu Ala Leu
                100                 105                 110

Ser Met Leu Arg Glu Asp Ile Gly Lys Phe Asp Val Val Ile Ser Asp
             115                 120                 125

Val Asp Met Pro Asp Met Asp Gly Phe Lys Leu Leu Glu Leu Val Gly
130                 135                 140

Leu Glu Met Asp Leu Pro Val Ile Met Val Ser Gly Asn Gly Glu Thr
145                 150                 155                 160

Ser Ala Val Met Lys Gly Ile Thr His Gly Ala Cys Asp Tyr Leu Leu
                165                 170                 175

Lys Pro Val Arg Ile Glu Glu Leu Arg Asn Ile Trp Gln His Val Val
                180                 185                 190

Arg Lys Lys Arg Arg Glu Val Lys Ala Val Thr Lys Ser Val Glu
            195                 200                 205

Glu Ala Gly Gly Cys Glu Arg Pro Lys Arg Gly Gly Ala Asp Asp
            210                 215                 220

Ala Asp Tyr Thr Ser Ser Ala Thr Asp Thr Thr Asp Ser Asn Trp Lys
225                 230                 235                 240

Leu Thr Lys Arg Arg Lys Gly Glu Phe Lys Asp Glu Asn Glu Asp
                245                 250                 255

Asn Glu Gln Glu Asn Asp Asp Pro Ser Thr Leu Lys Arg Pro Arg Val
            260                 265                 270

Val Trp Ser Val Glu Leu His Gln Gln Phe Val Ser Ala Val Asn Gln
            275                 280                 285

Leu Gly Ile Asp Lys Ala Val Pro Lys Arg Ile Leu Glu Leu Met Gly
            290                 295                 300

Val Gln Gly Leu Thr Arg Glu Asn Val Ala Ser His Leu Gln Lys Tyr
305                 310                 315                 320

Arg Leu Tyr Leu Lys Arg Leu Ser Gly Val Thr Ser Gln Gly Asn
                325                 330                 335

Met Ser Ala His Phe Gly Gly Ser Asp Pro Phe Cys Met Met Pro Pro
            340                 345                 350

Asp Met Ser Leu Ala Asn Gly Gln Leu Thr Pro Gln Ala Leu Ala Lys
            355                 360                 365

Phe His Met Leu Gly Arg Met Asn Ala Thr Asn Gly Ile Gly Phe Ser
            370                 375                 380

Gly Gly Gly Leu Asp Pro Gly Met Asn Gln Met Phe Leu Gln Asp Leu
385                 390                 395                 400

Pro Arg Pro Pro Gln Leu Asn Ser Met Leu Arg Asn Asn Thr Gly Leu
                405                 410                 415

Leu Ala Ser Val Pro Asn Gly Leu Gln His Leu Glu Gln Leu Ser Glu
            420                 425                 430
```

```
Pro His His Val His Val Asn Glu Leu Glu His Tyr Pro Ser Asn
            435                 440                 445

Thr Lys Val Tyr Pro Gln Leu Asn Gly Asn Leu Asp Val Ser Val Gly
450                 455                 460

Pro Leu Gly Ala Ala Asn Gly Asn Leu Ala Ser Asn Pro Asn Ser Asp
465                 470                 475                 480

Thr Leu Leu Met His Ile Leu His Ser Arg Ala Ser Gln Gln Gly Val
                485                 490                 495

Gly Ser Pro Ser Thr Leu Pro Gln Pro Arg Cys Gly Leu Asn Pro Thr
            500                 505                 510

His Leu Leu Ser Asn Asp Ile Asn Phe Ala Pro Val Gly Ser Leu Pro
        515                 520                 525

Asn Leu Ala Gly Ser Leu Gly Pro Ala Val Gly Leu Ser Ala Ile Pro
530                 535                 540

Gly Ser Ala Gly Gly Arg Asp Leu Ser Pro Ser Val Gly Gly Ser Gly
545                 550                 555                 560

Ala Ser Leu Ser Ser Pro Leu Gly Ser Leu Val Arg Arg Pro Leu Met
                565                 570                 575

Ala Glu Glu Gln Ser Asn Pro Val Asn Ser Thr Asn Gly Thr Tyr Ser
            580                 585                 590

Met Ala His Ser Gly Gln Ser Pro Lys Pro Ser Gly Asp Thr Leu Pro
        595                 600                 605

Thr Pro Leu Asn Glu Gly Leu Glu Gln Gln Gln Pro Leu Trp Ala Leu
    610                 615                 620

Tyr Gln Asn Pro Met Asn Gln Leu Ser His Gly Pro Ser Gln Gly Phe
625                 630                 635                 640

Pro His Asp Ser Leu Gln Trp Ser Val Leu Thr Glu Asn Leu Ser Phe
                645                 650                 655

Gly Asp Met Gly Gln Ser Leu Ser Ala Gly Leu Ile Ser Gln Phe Ser
            660                 665                 670

Ser Gln Gly Gln Asp Asn Gly Ile Gly Phe Ala Pro Pro Ser Gln Arg
        675                 680                 685

Gly Ser Tyr Thr Arg Gln Ser Val Ser Phe Pro Ala Ser Ser Ala Leu
    690                 695                 700

Asp Gly Arg Met Val Arg Ser Ser Tyr Glu Pro
705                 710                 715

<210> SEQ ID NO 22
<211> LENGTH: 60
<212> TYPE: PRT
<213> ORGANISM: Parachlorella sp
<220> FEATURE:
<221> NAME/KEY: misc_feature
<223> OTHER INFORMATION: Myb domain of SGI1 polypeptide of SEQ ID NO: 8

<400> SEQUENCE: 22

Lys Lys Pro Arg Val Val Trp Ser Val Glu Met His Gln Gln Phe Val
1               5                   10                  15

Asn Ala Val Asn Ser Leu Gly Ile Asp Lys Ala Val Pro Lys Arg Ile
            20                  25                  30

Leu Asp Leu Met Asn Val Glu Gly Leu Thr Arg Glu Asn Val Ala Ser
        35                  40                  45

His Leu Gln Lys Tyr Arg Leu Tyr Leu Lys Arg Val
    50                  55                  60

<210> SEQ ID NO 23
```

```
<211> LENGTH: 51
<212> TYPE: PRT
<213> ORGANISM: Coccomyxa subellipsoidea
<220> FEATURE:
<221> NAME/KEY: misc_feature
<223> OTHER INFORMATION: Myb domain of SGI1 polypeptide of SEQ ID NO: 9

<400> SEQUENCE: 23

Lys Lys Ala Arg Val Val Trp Ser Val Glu Met His Gln Gln Phe Val
1               5                   10                  15

Gln Ala Val Asn Gln Leu Gly Ile Asp Lys Ala Val Pro Lys Arg Ile
            20                  25                  30

Leu Asp Leu Met Asn Val Asp Gly Leu Thr Arg Glu Asn Val Ala Ser
        35                  40                  45

His Leu Gln
    50

<210> SEQ ID NO 24
<211> LENGTH: 61
<212> TYPE: PRT
<213> ORGANISM: Ostreococcus lucimarinus
<220> FEATURE:
<221> NAME/KEY: misc_feature
<223> OTHER INFORMATION: Myb domain of SGI1 polypeptide of SEQ ID NO: 10

<400> SEQUENCE: 24

Lys Lys Pro Arg Val Val Trp Ser Ala Glu Leu His Ala Gln Phe Val
1               5                   10                  15

Thr Ala Val Asn Gln Leu Gly Ile Asp Lys Ala Val Pro Lys Arg Ile
            20                  25                  30

Leu Asp Leu Met Gly Val Gln Gly Leu Thr Arg Glu Asn Val Ala Ser
        35                  40                  45

His Leu Gln Lys Tyr Arg Leu Tyr Leu Lys Arg Leu Gln
    50                  55                  60

<210> SEQ ID NO 25
<211> LENGTH: 65
<212> TYPE: PRT
<213> ORGANISM: Chlamydomonas reinhardtii
<220> FEATURE:
<221> NAME/KEY: misc_feature
<223> OTHER INFORMATION: Myb domain of SGI1 polypeptide of SEQ ID NO: 11

<400> SEQUENCE: 25

Lys Lys Ala Arg Val Val Trp Ser Val Glu Met His Gln Gln Phe Val
1               5                   10                  15

Asn Ala Val Asn Gln Leu Gly Ile Asp Lys Ala Val Pro Lys Lys Ile
            20                  25                  30

Leu Glu Ile Met Gly Val Asp Gly Ser Ala Gly Arg Leu Ala Asp Thr
        35                  40                  45

Ser Gly Arg Asp Val Cys Gly Thr Val Tyr Arg Leu Tyr Leu Lys Arg
    50                  55                  60

Val
65

<210> SEQ ID NO 26
<211> LENGTH: 61
<212> TYPE: PRT
<213> ORGANISM: Chromochloris zofingiensis
<220> FEATURE:
<221> NAME/KEY: misc_feature
<223> OTHER INFORMATION: Myb domain of SGI1 polypeptide of SEQ ID NO: 9
```

-continued

```
<400> SEQUENCE: 26

Lys Lys Pro Arg Val Val Trp Ser Val Glu Met His Gln Gln Phe Val
1               5                   10                  15

Gln Ala Val Asn Gln Leu Gly Ile Asp Lys Ala Val Pro Lys Lys Ile
            20                  25                  30

Leu Glu Leu Met Asn Val Asp Gly Leu Thr Arg Glu Asn Val Ala Ser
        35                  40                  45

His Leu Gln Lys Tyr Arg Leu Tyr Leu Lys Arg Val Gln
    50                  55                  60

<210> SEQ ID NO 27
<211> LENGTH: 60
<212> TYPE: PRT
<213> ORGANISM: Volvox carteri
<220> FEATURE:
<221> NAME/KEY: misc_feature
<223> OTHER INFORMATION: Myb domain of SGI1 polypeptide of SEQ ID NO: 10

<400> SEQUENCE: 27

Lys Lys Ala Arg Val Val Trp Ser Val Glu Met His Gln Gln Phe Val
1               5                   10                  15

Asn Ala Val Asn Gln Leu Gly Ile Asp Lys Ala Val Pro Lys Lys Ile
            20                  25                  30

Leu Glu Ile Met Asn Val Asp Gly Leu Thr Arg Glu Asn Val Ala Ser
        35                  40                  45

His Leu Gln Lys Tyr Arg Leu Tyr Leu Lys Arg Val
    50                  55                  60

<210> SEQ ID NO 28
<211> LENGTH: 60
<212> TYPE: PRT
<213> ORGANISM: Tetraselmis sp.
<220> FEATURE:
<221> NAME/KEY: misc_feature
<223> OTHER INFORMATION: Myb domain of SGI1 polypeptide of SEQ ID NO: 11

<400> SEQUENCE: 28

Lys Lys Gln Arg Met Asn Trp Ser Asp Glu Met His Gln Gln Phe Val
1               5                   10                  15

Asn Ala Val Asn Gln Leu Gly Ile Asp Lys Ala Val Pro Lys Arg Ile
            20                  25                  30

Leu Asp Leu Met Ser Val Glu Gly Leu Thr Arg Glu Asn Val Ala Ser
        35                  40                  45

His Leu Gln Lys Tyr Arg Ile Tyr Leu Lys Arg Met
    50                  55                  60

<210> SEQ ID NO 29
<211> LENGTH: 60
<212> TYPE: PRT
<213> ORGANISM: Oocystis sp.
<220> FEATURE:
<221> NAME/KEY: misc_feature
<223> OTHER INFORMATION: Myb domain of SGI1 polypeptide of SEQ ID NO: 12

<400> SEQUENCE: 29

Lys Lys Pro Arg Val Val Trp Ser Val Glu Met His Gln Gln Phe Val
1               5                   10                  15

Asn Ala Val Asn Gln Leu Gly Ile Asp Lys Ala Val Pro Lys Arg Ile
            20                  25                  30

Leu Asp Leu Met Asn Val Asp Gly Leu Thr Arg Glu Asn Val Ala Ser
        35                  40                  45
```

His Leu Gln Lys Tyr Arg Leu Tyr Leu Lys Arg Val
        50                  55                  60

<210> SEQ ID NO 30
<211> LENGTH: 61
<212> TYPE: PRT
<213> ORGANISM: Micromonas sp.
<220> FEATURE:
<221> NAME/KEY: misc_feature
<223> OTHER INFORMATION: Myb domain of SGI1 polypeptide of SEQ ID NO: 18

<400> SEQUENCE: 30

Lys Lys Pro Arg Val Val Trp Ser Ala Glu Leu His Gln Gln Phe Val
1               5                   10                  15

Thr Ala Val Asn Gln Leu Gly Ile Asp Lys Ala Val Pro Lys Arg Ile
            20                  25                  30

Leu Asp Leu Met Gly Val Gln Gly Leu Thr Arg Glu Asn Val Ala Ser
        35                  40                  45

His Leu Gln Lys Tyr Arg Leu Tyr Leu Lys Arg Leu Gln
    50                  55                  60

<210> SEQ ID NO 31
<211> LENGTH: 126
<212> TYPE: PRT
<213> ORGANISM: Parachlorella sp
<220> FEATURE:
<221> NAME/KEY: misc_feature
<223> OTHER INFORMATION: Response Regulator receiver domain of SGI1
      polypeptide of SEQ ID NO: 6 or 7

<400> SEQUENCE: 31

Pro Ala Gly Leu Lys Val Leu Val Val Asp Asp Leu Met Cys Leu
1               5                   10                  15

Lys Val Val Ser Ala Met Leu Lys Arg Cys Ser Tyr Gln Val Ala Thr
            20                  25                  30

Cys Ser Ser Gly Ser Glu Ala Leu Thr Leu Leu Arg Glu Arg Asn Glu
        35                  40                  45

Asp Gly Ser Ser Asp Gln Phe Asp Leu Val Leu Ser Asp Val Tyr Met
    50                  55                  60

Pro Asp Met Asp Gly Phe Lys Leu Leu Glu His Ile Gly Leu Glu Leu
65                  70                  75                  80

Glu Leu Pro Val Ile Met Met Ser Ser Asn Gly Asp Thr Asn Val Val
                85                  90                  95

Leu Arg Gly Val Thr His Gly Ala Val Asp Phe Leu Ile Lys Pro Val
            100                 105                 110

Arg Ile Glu Glu Leu Arg Asn Val Trp Gln His Val Val Arg
        115                 120                 125

<210> SEQ ID NO 32
<211> LENGTH: 123
<212> TYPE: PRT
<213> ORGANISM: Coccomyxa subellipsoidea
<220> FEATURE:
<221> NAME/KEY: misc_feature
<223> OTHER INFORMATION: sub-sequence of Response Regulator receiver
      domain of SGI1 polypeptide of SEQ ID NO: 9

<400> SEQUENCE: 32

Pro Ala Gly Leu Lys Val Leu Val Val Asp Asp Pro Leu Cys Leu
1               5                   10                  15

Lys Val Val Glu His Met Leu Arg Arg Cys Asn Tyr Gln Val Thr Thr

```
                20                  25                  30

Cys Pro Asn Gly Lys Ala Ala Leu Glu Lys Leu Arg Asp Arg Ser Val
            35                  40                  45

His Phe Asp Leu Val Leu Ser Asp Val Tyr Met Pro Asp Met Asp Gly
    50                  55                  60

Phe Lys Leu Leu Glu His Ile Gly Leu Glu Leu Asp Leu Pro Val Ile
65                  70                  75                  80

Met Met Ser Ser Asn Gly Glu Thr Asn Val Val Leu Arg Gly Val Thr
                85                  90                  95

His Gly Ala Val Asp Phe Leu Ile Lys Pro Val Arg Val Glu Glu Leu
            100                 105                 110

Arg Asn Val Trp Gln His Val Val Arg Arg Lys
            115                 120

<210> SEQ ID NO 33
<211> LENGTH: 122
<212> TYPE: PRT
<213> ORGANISM: Ostreococcus lucimarinus
<220> FEATURE:
<221> NAME/KEY: misc_feature
<223> OTHER INFORMATION: sub-sequence of Response Regulator receiver
      domain of SGI1 polypeptide of SEQ ID NO: 10

<400> SEQUENCE: 33

Pro Ala Gly Leu Gly Val Leu Val Asp Asp Leu Leu Cys Leu
1               5                   10                  15

Lys Val Val Glu Lys Met Leu Lys Ala Cys Lys Tyr Lys Val Thr Ala
                20                  25                  30

Cys Ser Thr Ala Lys Thr Ala Leu Glu Ile Leu Arg Thr Arg Lys Glu
            35                  40                  45

Glu Phe Asp Ile Val Leu Ser Asp Val His Met Pro Met Asp Gly
    50                  55                  60

Phe Lys Leu Leu Glu Ile Ile Gln Phe Glu Leu Ala Leu Pro Val Leu
65                  70                  75                  80

Met Met Ser Ala Asn Ser Asp Ser Ser Val Val Leu Arg Gly Ile Ile
                85                  90                  95

His Gly Ala Val Asp Tyr Leu Leu Lys Pro Val Arg Ile Glu Glu Leu
            100                 105                 110

Arg Asn Ile Trp Gln His Val Val Arg Arg
            115                 120

<210> SEQ ID NO 34
<211> LENGTH: 123
<212> TYPE: PRT
<213> ORGANISM: Chlamydomonas reinhardtii
<220> FEATURE:
<221> NAME/KEY: misc_feature
<223> OTHER INFORMATION: sub-sequence of Response Regulator receiver
      domain of SGI1 polypeptide of SEQ ID NO: 11

<400> SEQUENCE: 34

Pro Ala Gly Leu Arg Leu Leu Val Asp Asp Pro Leu Cys Leu
1               5                   10                  15

Lys Val Val Glu Gln Met Leu Arg Lys Cys Ser Tyr Glu Val Thr Val
                20                  25                  30

Cys Ser Asn Ala Thr Thr Ala Leu Asn Ile Leu Arg Asp Lys Asn Thr
            35                  40                  45

Glu Tyr Asp Leu Val Leu Ser Asp Val Tyr Met Pro Asp Met Asp Gly
    50                  55                  60
```

Phe Arg Leu Leu Glu Leu Val Gly Leu Glu Met Asp Leu Pro Val Ile
65                  70                  75                  80

Met Met Ser Ser Asn Gly Asp Thr Ser Asn Val Leu Arg Gly Val Thr
                85                  90                  95

His Gly Ala Cys Asp Tyr Leu Ile Lys Pro Val Arg Leu Glu Glu Leu
            100                 105                 110

Arg Asn Leu Trp Gln His Val Val Arg Arg Arg
        115                 120

<210> SEQ ID NO 35
<211> LENGTH: 61
<212> TYPE: PRT
<213> ORGANISM: Chromochloris zofingiensis
<220> FEATURE:
<221> NAME/KEY: misc_feature
<223> OTHER INFORMATION: Response Regulator receiver domain of SGI1
      polypeptide of SEQ ID NO: 12

<400> SEQUENCE: 35

Met Asp Gly Phe Lys Leu Leu Glu Thr Val Gly Leu Glu Leu Asp Leu
1               5                   10                  15

Pro Val Ile Met Met Ser Ser Asn Gly Glu His Thr Thr Val Met Arg
            20                  25                  30

Gly Val Thr His Gly Ala Cys Asp Phe Leu Ile Lys Pro Val Arg Ile
            35                  40                  45

Glu Glu Leu Arg Asn Ile Trp Gln His Val Ile Arg Arg
            50                  55                  60

<210> SEQ ID NO 36
<211> LENGTH: 123
<212> TYPE: PRT
<213> ORGANISM: Volvox carteri
<220> FEATURE:
<221> NAME/KEY: misc_feature
<223> OTHER INFORMATION: Response Regulator receiver domain of SGI1
      polypeptide of SEQ ID NO: 13

<400> SEQUENCE: 36

Pro Ala Gly Leu Arg Leu Leu Val Val Asp Asp Pro Leu Cys Leu
1               5                   10                  15

Lys Val Val Glu Gln Met Leu Arg Lys Cys Ser Tyr Asp Val Thr Thr
            20                  25                  30

Cys Thr Asn Ala Thr Met Ala Leu Asn Leu Leu Arg Asp Lys Ser Thr
            35                  40                  45

Glu Tyr Asp Leu Val Leu Ser Asp Val Tyr Met Pro Asp Met Asp Gly
            50                  55                  60

Phe Lys Leu Leu Glu Val Val Gly Leu Glu Met Asp Leu Pro Val Ile
65                  70                  75                  80

Met Met Ser Ser Asn Gly Asp Thr Ser Asn Val Leu Arg Gly Val Thr
                85                  90                  95

His Gly Ala Cys Asp Tyr Leu Ile Lys Pro Val Arg Leu Glu Glu Leu
            100                 105                 110

Arg Asn Leu Trp Gln His Val Val Arg Arg Arg
        115                 120

<210> SEQ ID NO 37
<211> LENGTH: 121
<212> TYPE: PRT
<213> ORGANISM: Tetraselmis sp.
<220> FEATURE:

```
<221> NAME/KEY: misc_feature
<223> OTHER INFORMATION: Response Regulator receiver domain of SGI1
      polypeptide of SEQ ID NO: 14, 15, and 16

<400> SEQUENCE: 37

Pro Ala Gly Leu Arg Val Leu Val Ala Asp Asn Asp Pro Ala Ser Leu
1               5                   10                  15

Gln Gln Val Glu Lys Met Leu Lys Lys Cys Ser Tyr Gln Val Thr Leu
            20                  25                  30

Cys Ser Ser Gly Lys Asn Ser Leu Glu Ile Leu Arg Lys Arg Arg Glu
        35                  40                  45

Glu Phe Asp Leu Val Leu Ala Asp Ala Asn Leu Pro Asp Ile Asp Gly
    50                  55                  60

Phe Lys Leu Leu His Val Cys His Thr Glu Leu Ser Leu Pro Val Val
65                  70                  75                  80

Leu Met Ser Gly Thr Ser Asp Thr Gln Leu Val Met Arg Gly Val Met
                85                  90                  95

Asp Gly Ala Arg Asp Phe Leu Ile Lys Pro Leu Arg Val Glu Glu Leu
            100                 105                 110

Lys Val Leu Trp Gln His Leu Val Arg
        115                 120

<210> SEQ ID NO 38
<211> LENGTH: 123
<212> TYPE: PRT
<213> ORGANISM: Oocystis sp.
<220> FEATURE:
<221> NAME/KEY: misc_feature
<223> OTHER INFORMATION: Response Regulator receiver domain of SGI1
      polypeptide of SEQ ID NO: 17

<400> SEQUENCE: 38

Pro Ala Gly Leu Lys Val Leu Val Asp Asp Pro Leu Cys Leu
1               5                   10                  15

Lys Val Ile Asp Gln Met Leu Arg Arg Cys Asn Tyr Ala Ala Thr Thr
            20                  25                  30

Cys Gln Ser Ser Leu Glu Ala Leu Glu Leu Leu Arg Ser Ser Lys Glu
        35                  40                  45

Asn His Phe Asp Leu Val Leu Ser Asp Val Tyr Met Pro Asp Met Asp
    50                  55                  60

Gly Phe Lys Leu Leu Glu Ile Ile Gly Leu Glu Met Gly Leu Pro Val
65                  70                  75                  80

Ile Met Met Ser Ser Asn Gly Glu Thr Gly Val Val Phe Arg Gly Val
                85                  90                  95

Thr His Gly Ala Val Asp Phe Leu Ile Lys Pro Val Arg Ile Glu Glu
            100                 105                 110

Leu Arg Asn Leu Trp Gln His Val Val Arg Lys
        115                 120

<210> SEQ ID NO 39
<211> LENGTH: 123
<212> TYPE: PRT
<213> ORGANISM: Micromonas sp.
<220> FEATURE:
<221> NAME/KEY: misc_feature
<223> OTHER INFORMATION: Response Regulator receiver domain of SGI1
      polypeptide of SEQ ID NO: 18

<400> SEQUENCE: 39

Pro Ile Gly Leu Arg Val Leu Val Val Asp Asp Pro Leu Cys Leu
```

-continued

```
                1               5                  10                  15

Lys Ile Val Glu Lys Met Leu Lys Arg Cys Gln Tyr Glu Val Thr Thr
                    20                  25                  30

Phe Ser Arg Gly Ala Glu Ala Leu Lys Thr Leu Arg Glu Arg Lys Asp
                    35                  40                  45

Asp Phe Asp Ile Val Leu Ser Asp Val His Met Pro Asp Met Asp Gly
        50                  55                  60

Phe Lys Leu Leu Glu His Ile Ala Leu Glu Leu Asp Ile Pro Val Met
65                  70                  75                  80

Met Met Ser Ala Asn Cys Ala Thr Asp Val Val Leu Arg Gly Ile Ile
                    85                  90                  95

His Gly Ala Val Asp Tyr Leu Leu Lys Pro Val Arg Ile Glu Glu Leu
                    100                 105                 110

Arg Asn Ile Trp Gln His Val Val Arg Arg Lys
                    115                 120
```

<210> SEQ ID NO 40
<211> LENGTH: 45
<212> TYPE: PRT
<213> ORGANISM: Parachlorella sp
<220> FEATURE:
<221> NAME/KEY: misc_feature
<223> OTHER INFORMATION: Response Regulator receiver domain of SGI1
      polypeptide of SEQ ID NO: 8

<400> SEQUENCE: 40

```
Leu Pro Val Ile Met Met Ser Ser Asn Gly Asp Thr Asn Val Val Leu
1               5                   10                  15

Arg Gly Val Thr His Gly Ala Val Asp Phe Leu Ile Lys Pro Val Arg
                    20                  25                  30

Ile Glu Glu Leu Arg Asn Val Trp Gln His Val Val Arg
                    35                  40                  45
```

<210> SEQ ID NO 41
<211> LENGTH: 47
<212> TYPE: PRT
<213> ORGANISM: Coccomyxa subellipsoidea
<220> FEATURE:
<221> NAME/KEY: misc_feature
<223> OTHER INFORMATION: Response Regulator receiver domain of SGI1
      polypeptide of SEQ ID NO: 9

<400> SEQUENCE: 41

```
Leu Pro Val Ile Met Met Ser Ser Asn Gly Glu Thr Asn Val Val Leu
1               5                   10                  15

Arg Gly Val Thr His Gly Ala Val Asp Phe Leu Ile Lys Pro Val Arg
                    20                  25                  30

Val Glu Glu Leu Arg Asn Val Trp Gln His Val Val Arg Arg Lys
                    35                  40                  45
```

<210> SEQ ID NO 42
<211> LENGTH: 46
<212> TYPE: PRT
<213> ORGANISM: Ostreococcus lucimarinus
<220> FEATURE:
<221> NAME/KEY: misc_feature
<223> OTHER INFORMATION: Response Regulator receiver domain of SGI1
      polypeptide of SEQ ID NO: 10

<400> SEQUENCE: 42

```
Leu Pro Val Leu Met Met Ser Ala Asn Ser Asp Ser Ser Val Val Leu
1               5                   10                  15
```

-continued

```
Arg Gly Ile Ile His Gly Ala Val Asp Tyr Leu Leu Lys Pro Val Arg
            20                  25                  30

Ile Glu Glu Leu Arg Asn Ile Trp Gln His Val Val Arg Arg
        35                  40                  45
```

<210> SEQ ID NO 43
<211> LENGTH: 47
<212> TYPE: PRT
<213> ORGANISM: Chlamydomonas reinhardtii
<220> FEATURE:
<221> NAME/KEY: misc_feature
<223> OTHER INFORMATION: Response Regulator receiver domain of SGI1
      polypeptide of SEQ ID NO: 11

<400> SEQUENCE: 43

```
Leu Pro Val Ile Met Met Ser Ser Asn Gly Asp Thr Ser Asn Val Leu
1               5                   10                  15

Arg Gly Val Thr His Gly Ala Cys Asp Tyr Leu Ile Lys Pro Val Arg
            20                  25                  30

Leu Glu Glu Leu Arg Asn Leu Trp Gln His Val Val Arg Arg
        35                  40                  45
```

<210> SEQ ID NO 44
<211> LENGTH: 46
<212> TYPE: PRT
<213> ORGANISM: Chromochloris zofingiensis
<220> FEATURE:
<221> NAME/KEY: misc_feature
<223> OTHER INFORMATION: Response Regulator receiver domain of SGI1
      polypeptide of SEQ ID NO: 12

<400> SEQUENCE: 44

```
Leu Pro Val Ile Met Met Ser Ser Asn Gly Glu His Thr Thr Val Met
1               5                   10                  15

Arg Gly Val Thr His Gly Ala Cys Asp Phe Leu Ile Lys Pro Val Arg
            20                  25                  30

Ile Glu Glu Leu Arg Asn Ile Trp Gln His Val Ile Arg Arg
        35                  40                  45
```

<210> SEQ ID NO 45
<211> LENGTH: 47
<212> TYPE: PRT
<213> ORGANISM: Volvox carteri
<220> FEATURE:
<221> NAME/KEY: misc_feature
<223> OTHER INFORMATION: Response Regulator receiver domain of SGI1
      polypeptide of SEQ ID NO: 13

<400> SEQUENCE: 45

```
Leu Pro Val Ile Met Met Ser Ser Asn Gly Asp Thr Ser Asn Val Leu
1               5                   10                  15

Arg Gly Val Thr His Gly Ala Cys Asp Tyr Leu Ile Lys Pro Val Arg
            20                  25                  30

Leu Glu Glu Leu Arg Asn Leu Trp Gln His Val Val Arg Arg Arg
        35                  40                  45
```

<210> SEQ ID NO 46
<211> LENGTH: 45
<212> TYPE: PRT
<213> ORGANISM: Tetraselmis sp.
<220> FEATURE:
<221> NAME/KEY: misc_feature
<223> OTHER INFORMATION: Response Regulator receiver domain of SGI1
      polypeptide of SEQ ID NO: 14

<400> SEQUENCE: 46

Leu Pro Val Val Leu Met Ser Gly Thr Ser Asp Thr Gln Leu Val Met
1               5                   10                  15

Arg Gly Val Met Asp Gly Ala Arg Asp Phe Leu Ile Lys Pro Leu Arg
            20                  25                  30

Val Glu Glu Leu Lys Val Leu Trp Gln His Leu Val Arg
        35                  40              45

<210> SEQ ID NO 47
<211> LENGTH: 46
<212> TYPE: PRT
<213> ORGANISM: Oocystis sp.
<220> FEATURE:
<221> NAME/KEY: misc_feature
<223> OTHER INFORMATION: Response Regulator receiver domain of SGI1
    polypeptide of SEQ ID NO: 17

<400> SEQUENCE: 47

Leu Pro Val Ile Met Met Ser Ser Asn Gly Glu Thr Gly Val Val Phe
1               5                   10                  15

Arg Gly Val Thr His Gly Ala Val Asp Phe Leu Ile Lys Pro Val Arg
            20                  25                  30

Ile Glu Glu Leu Arg Asn Leu Trp Gln His Val Val Arg Lys
        35                  40              45

<210> SEQ ID NO 48
<211> LENGTH: 47
<212> TYPE: PRT
<213> ORGANISM: Micromonas sp.
<220> FEATURE:
<221> NAME/KEY: misc_feature
<223> OTHER INFORMATION: Response Regulator receiver domain of SGI1
    polypeptide of SEQ ID NO: 18

<400> SEQUENCE: 48

Ile Pro Val Met Met Met Ser Ala Asn Cys Ala Thr Asp Val Val Leu
1               5                   10                  15

Arg Gly Ile Ile His Gly Ala Val Asp Tyr Leu Leu Lys Pro Val Arg
            20                  25                  30

Ile Glu Glu Leu Arg Asn Ile Trp Gln His Val Val Arg Arg Lys
        35                  40              45

<210> SEQ ID NO 49
<211> LENGTH: 9898
<212> TYPE: DNA
<213> ORGANISM: Parachlorella sp

<400> SEQUENCE: 49
atggggactt tttcccgcaa atccttctca aacttagcag cactcgctga cggtgacttt        60
gggcagggat ctcaaaacga tttgcgcggt ggtggccccc tgtctttgag ctcagctgcc       120
aaccgcacct ctcggaactc aatcgatagt gatggcaggc ggctccagcg gtgggtggac       180
caattttaat cgtctgaaga gtgtataata tgcatcgctt aatctatatg cgtcttctt        240 gcgaaccagg gctacctgta agcactgcct agtatcgtcc ttaccaattt gttcgcaggc       300
ttatctttgt gagcaaccac ctgccgctcc gcgtttcgaa gggagccacc gactggaatt       360
tcgagtggga cgacgatgcg ttgatcgcgc aggccaagga gggcctgccg gaggacatgg       420
aggcactata tgttggttgc ctccctgtgg aggtggaccc tcaggaccaa gacgtgagca       480
actggggtgc accacagctt tgcaactata tatcccttig ccactcgctg cttgctgggt       540

```
gcctgagcaa cggcggaaag ctgacagtgc ttgggtttag agctgcacca gaggcgctgc    600
ctgaagtgac ggttctgttc actgcctccc aagctacgtg tgtgcaactt caatctgtac    660
catgccactg caggaggtca gcctgcagct acagaagcag cacaactgct tccctgtttt    720
tcttgggacg gagctcaaga ccaactatta cagaagtgag gcccatcact gcccctgcag    780
cactcttgcc gtctgccccc ccacttcatt ttgcaccata ctccctttgg gactcaccaa    840
ctgggtgggg cactgttgca ttgcttcctg gcgcatcgtt aggttgggat tgagctgacg    900
caaaccaagg ttggcaccgc ccctgtgcca ataatcacc gctgggcagc catccttttg     960
ctggccccgg caccagcacc ggcccctgct ccgcctgtgc tctgggcacg gggcacgaaa   1020
aaaaactgct gaatggatgg agtgatgtgc agggcttgct cgaatgctgg ccaccgcctc   1080
catttgcacc cacagtgtca ccagtcacac atgctgcacc caagcataag ggaagggact   1140
gtgagtggaa gaagggagg caatgcaatg aacagaaag gctggagtgc ggggcatact     1200
gtccgcaatc gcaccgcagc caggccttgc gtctgcaaac agagatgcgg tgcacagatg   1260
cagcacacgc ctgccacctg tgtgcgtgag catgcatgtg ctgtgtgtgt gccattgggc   1320
tggtgcagag ttctgcaagc agcagctgtg gcccatcctg cactacctca tccccctcaa   1380
ccccactagc ctaggcaggt ttgaccccgg actctgggcg tcatacgtga gggcgaacaa   1440
ggtaggcgag gtagagctga ggggtggagg agagggggtg gagagggtgg atcatggtga   1500
cgtgtgaagg gaggggggagg gtgggtaggt gttgggtggg gtcaggaggg gatgaccatg   1560
tgattgagag cttggtgcac atcctctccc cccttgcaat ggcaggtgaa gtggagaaga   1620
gaaggcaggg gtgtaagatt gggcatagtg tggagtgcag gaaggccttg cgaaaaggaa   1680 gggggggatgc atgcttgctg tgccgtgaca ggcgtgctcc ggctggtgga tctgaaaca   1740 ttgtgggttg gagggaatg ccaggaacat tcctgttccc tcttcccgc acccggcctt    1800 atggcaccta agcaccggtc cccgcccact accctaccca ctcacctcca gcttcccct    1860 ggcatatgct ctcaaggtgg ccatagtggc ctcctcgctg ccagccatca cgtatgggtt   1920
gggagggagg aaaaaggggg ggggggaggtg gcggtgccac atctaccagg tgcgcgaccc   1980
tagaaaagtc caccccgcccc tcttccttca ggtgtttgcg gacaagatgg tggaggtgct   2040
ggggtcgctg gaggacgact ttgtgtgggt gcacgactac cacctgctgg tgctgccctc   2100
gctgctgcgg aaaagattcc acagaatcaa gtgagatccc ggggagcaag caagacccag   2160
cccatgcgtg gttgcatggg ggagtacggg tgcccatgca ggctagtagg ggtggggtgt   2220 gggaagggt catttccggg gggagagcgg gggtgtgggt gaggggtctc ttcttcaacc    2280
caccacgttg acgtggcttg ctttggagtc ctgtttatc ctgcattcag ggtttcgtgc    2340
tacgtttgct cgcctcgcac cttccgtgg aacggttgca tgcccttctc cttcagcggg    2400
gtgctggcac atgcagcccg ttagtgcaat gccattagga ggggggcagg gaggggggga   2460
gtggcatgga aggacgggaa aatgaggcaa aagaggtggg caggtgcaag ggtgtgtagc   2520
tgccaggata ggagggctgg acaccaggta ctaacccgt gcctggtccg cgctgcaggt    2580
gcggaatctt cctccactcc cccttccct ctccgaggt gttccgaacc ttcccccggc     2640
gggaagagat catacggtcc atgctgaatg cggatcttat aggtggggca tcacccacca   2700
ccaccaacct tccacttacc ccttcacacc ccatccaccc cttcccctc gcacagcaat    2760 gttcctcacc taacttgtcc ctatctcata caccagacgt ggacaccgc accccctccc    2820 cccccatatc ccctccccc cccccatact ccctcccccc cttcgtcctc gcttttaact   2880
```

-continued

```
cacagctgtg tgcatctatt catatctgaa ccttcctttc ggcaaggtgt tgtcatgggg    2940
ttaagccatg ggcacccatc gctgcagctg cccaccagct tctcgctgtc ccctgtcac    3000 cccgtcaaac acgcccctcc cccccccccc cccgcaggct tccacacctt tgactacgcg    3060
cggcacttcc tgtcatgctg cgcccgcatg ctgggactgg agcacaagac cagccggggg    3120
gccatcatca tcgagtacta cggcagggac gtgggcatca aaatcatgcc cacaggtgag    3180
gggaagggga ggggctgtat tgtgtgctgc gttgtgcgtg cttgggtgtg tccgtgcatg    3240
cgtgtgcgtg ggtgtcattc aatgagtgtg ggggcaggg ggctcctctg tgtcacgtga    3300
ggggtcacag gccaaggtga gtcaagccaa ccagggttag tcatgcgtgc cagctggctg    3360
cagctgtgtg cgggtgcgga agggccaatc tggccatctg ctgcctgctg gggagggggg    3420
gttgcattgt cccccttcatg ctgcgcatgc tgtgctactt tctggaagcc ctgagagctg    3480
ctgttgactt accagctccc ccccctcct cccccctacc ccaggcgtga agccctcccg    3540
cttcctcagt gccttcagct ggaaggacac agagtggagg aggggggagc tggcggcgca    3600
ggtgagcggc gctggtttgc cgctgataag ggggggggttg aggggggcga caataaaata    3660
tgatgttttg ctacaaaatc accctcgacc tcagctcgta gggtgggcaa catgtggggc    3720
gaacggggag ggggggggggg gggggcgag atcccacaga atccgtagga ttcacgaata    3780
tgtacttttg acctttttcaa ccatacccctt ttgccgccac ctcccatttc gaagagggcg    3840
ggggggtccc aatcattcag cgtccgggtg gctgccttga ggatatttga tggggcgcca    3900
ccctccccag cttcccacca gcttcttgct gtctgggcca tccccagtcg ccatctttct    3960
ccatcattca cccatgcccc acgttccgtt cccatcaccc acccatgctc tcctataacc    4020
taaaaatcgg ccaaagacta ggggagcgtc taggtgaaaa ttttttgatta agtacatgaa    4080 aatttcttac gtgcacccca cccacccacc caccctcccc cctgtgcagt tcaagggcaa    4140
gacggtgctg ctgggcatgg acgacttgga cgtgttcaag gggatcgagc tgcggctggc    4200
cgccttcaag gacgtgctgg agtaccaccc ggagtggaag gggaggctgg tgctgctgca    4260
ggtcaccacc acaaggtgcg cggcaacggg ctgcgttgtg ggtttttttcc ccttgttttc    4320 cgttcgcttt tccagttcat aggaaggaaa cagcagatag tacaagttat gccgtgtctg    4380
ttgtctctgt ttttttttttt agaaggaaag agagctgatt cattttgagt tcaagttgaa    4440
aaacaacgaa aacatgaaag tgaagagtga ggttcagtca ttggtaggct tcaggcgtgt    4500
gtggtggcgg ggggctgcgg gtcggcacca ccgggttggc ggcagtgaag tgcgttttta    4560
actgtcgggg tgagggcggg catggaaggt cgtgcattgg aagggggcat ggggcggggt    4620
gggatgggta ctgctgctgc aggtgcctcc tgaacgggtg ggtggctgtc tgctgaggct    4680
gtggagggtg cagggcgtag ggcttattct agggtgctga agcggggtga tttcgatgcg    4740
gggctggggt tgctttggtg gagtgcgggt ttggtcctcc attcgccccc ccacccaccc    4800
accctggtgc cgcagggccc ccggccgcga cgtggacgac ctatttgact tcatcacgaa    4860
gcaggtggag gagatcaacg agcggtttgg ggcgccgggg taccagccgg tggtgtggtt    4920
taaccgcccc gtacccatgt acgagcgcat cgccatgctg tccatcgcag gtgaggcgct    4980
tctgcgcttc tgcagtgcaa tgctgctgcg ctgctccact gctgcacttg tgcgctgctg    5040
tgatgcggtg ctgctgtagt cgctgtactg cacccccggac ggacaacccc cgccacgctg    5100
tccccgaggc ggtccggcca ctgcctggcc cttgctgaca tggcggctaa ccctgccctg    5160
ccctgcagac gtggcggtgg tgacggccac gcgtgacggg atgaacctga tgccgtacga    5220
gtacgtggtg tgccgacagg tgcgtcccct cccccccccc ccccttgtcc ctgaacctcc    5280
```

```
tatgccccac gacccagacc ctgctctatg tccgtgtgcc ctgggaccgc gcttctcaat    5340
tcccacacct gcgctctgct acaccaacag gctcccccctg ctccgctgcc tgcgccaccc    5400
cccccctaca gcccccacc actctctcct cccaccctct cctcggcagt tccggatgca    5460 gcaccccag gtgcagggcc cgctctctcc ccactcactg gcagggccag ggcggcggag    5520
aaggaaggct cgtgcccaac tacacggaaa cctgcacctt gacctcgcgt gctggcagct    5580
tcaggcctat ggggtccagg gtgtgttcgc ctccctcccc tccttacctc agcctgcagg    5640
ttgggtaccc ttttcgggct tccctcagaa caccccaccc cccccctct ctcctgcagg    5700 gtcccccagg tctggcagag acggaggggcc ccgccacag ccagctggtg gtgtcggagt    5760
ttgtggggtg ctcgccctcg ctgtcggggg ccatccgggt caaccctgg agcatcgaag    5820 cggtacgtac cgcggtgcag agcgcgcagc gccctgcatg gattgctccc ccccccaac    5880 cccctccctt ttaccctgc cgtcaccccc ccccctccc tcctcccatc ccatccaacc    5940
ctgccgccac cctgggggcg ggacgccgtg gcacctctgc ccatcacccc tctttgacac    6000
gtgtccgaac ctttgcggta tgcccagctg cccgagcccc cctgcggca ggagggcgcc    6060 gttccaatcg gagcccccat actgctcgtt acactgtatc attcaagttg atgtattttt    6120
gcatacctag agaatgcatt gatgcttgca atttgtcgac tcgtacattt cacatcgtag    6180
ttgttcatgc gatgctaagt ttggtgcaag gtttgtgaag ctagttgaac tcccttccca    6240
caagatttca actgaagttt ttatactttg aagtcgccac acctccatct cacaagggtg    6300
taggagggcg aggttccgtt ctttcacaac aaccgcaacg atttctcgtc gtccagcaac    6360
agcagaagct gttgtgcgca cctgtgcttc aggcgtgggg agtgcatgtg tgcgcaggtc    6420
acacagtcct cccaccctcc ccgccagccc gcccaccaac acactcacgt cgtggtgatg    6480
catccctccc cctttcccct cgcctcctttc cccttgcccc ccttcctgcg ctcaccccct    6540
cacctgcttt cccctcccct cctgcaggtc cgggacgcat tgtacggcgc catccgcatg    6600
cccatagagg aacgtcacat ccggcacgag aagcactgga agtacgtctc ctcccacacc    6660
gttcagttct gggccaaggt gagcttgatg cagccggcgc ggtgcgggac caatgtcgca    6720
caccacccag cagcgcacgc agcagggcgg agcagtgctc ttaattgagg tgttaggatt    6780 aggggtttagg gacccaagac cccaagaccc ctcccttcca cacacacaca tgcacacgca    6840
cgcttacccc ttacccacac gctctctctc acacacactg ctgcctccct acaagaagcc    6900
cggcaccgcc cacctgtcac ataccggctt gaaatgccaa ttgcaatgcc cccccccc    6960 ccccccccgc cacccccttc ttctccccccg cgcagtccta cgtcaccgac ctgcagcgct    7020
tcacggccaa ccacagcaag ctgcagtgct tcgaccttgg gtttgcgctg gacaccttcc    7080
gcatggtggc ccttacctcc aacttcagga agctgcagac cgacactgtg gtcaaggcgt    7140
accagaggtg tgttctttgg ggggggggg ggagagggag taggtagatg cgaaattcgg    7200
tcgttcatgg aggtgtacac aagcttgatt gtcattcatt tcaaaattag acagcaagag    7260
ctcctgtcgc tgatttggtc ccagtggaaa aggactcacg gttgttgtta gatcgatgat    7320
cggagcgagg gaggggaagc ctgctggggg aggggggggg atttggcatg ggtggtggtc    7380
tgctgtgtgt gcaggcggtg tggtgtgagg ggttgggca tgcagtgcgg tgcagaggtg    7440
cgggtgtgat gagaaaacgg ggggtgctga cccccccct ccccccacct tcccacccgc    7500 tcccccccccc cccccccgtt ctacctaggg ccaagaagcg tgtgctgctg ctggaccacg    7560
acggtaccct gatggccccc tcctccatct cctcccgccc caccgaccac gtgctggcca    7620
```

```
cgctgcgcca gctcacctcc gacccgcgca acaccgtgta catcatctcc ggccgcgccc    7680
gcaccgagct gcaggagtgg ttcaagtcgg tggtgagtgg cgccccccaa cccctccctt    7740
catcgtcctt actcacccct tgctcatcac ccccgagctg caggagtggt tcaagtcggt    7800
tattagtagc ctaccccccc cccccccccc cccaaatctt cttcatcgcc cttcctcacc    7860
ccttacacat caccccacgg ttgcacacgt gcctggcctg gcaccagggc tgcgccccct    7920
actccccccc aaggtgtgaa ccctttggcc aagccggcta agctgaggt agtgtgcccc     7980
ccgccctccc ccccccact ctcaagcgcc ctgctgtctg ccgctgtgcc cccctcagc      8040
ggcggtgccc cccctctgt ctcacttttg cacacgcagc gcacgcgctc tctctccgcc     8100
ccccccctc ccccccccc cccgcccccc ttgtcaatcc actagttccc ccctgtgtg       8160
tgtcacccc catgcagccc aacctggggc tggctgcgga gcacggcttc tacctgtgga    8220
cccccggctc cgccgactgg gcggtgcagg acccggacat ggggtttggg tggaaagaga   8280
ttgtggagcc catcctccag gtggggggtg cggggcagcg ggtcttgcat actcatgcac   8340
tactgactga tgatgaccac gcaaccatgg tagggtttgg atgggaggac accgtggagc   8400
ccatcctcca ggtgggggge tcaggcctct cctacctggg catcgcagca aaccgccgtc   8460
cggttctgca tgggcgctgc ctagtgcaca gaaacccagg gggagtcggg gttgctccaa   8520
ccccaaccct acgcacagcc caccccctggc ttcaccctgg cttcacccct cctacccgcc  8580
acacgcctcg ccccctcctt ttccggcccc ccctcccccc cgcagcaacg cgtgcgcccc  8640
ctccccacct cccgtttctc tctcggaagg ccacccccct cagaggttga tgtgcgaatg   8700
acgaacttgc cgtcaccccc tttccagcct tgttttccac cgcttcctgg cccttttccac 8760
gccccttttca ccaccctgac gatcctcttc acccccccccc cccccccttct cgagcaggtg 8820
tacaccgagt ccacggacgg gtcccacatc gaagccaagg aaagcgcgct ggtgtggcac  8880
taccgcgacg ccgaccccga ctttgggtcg tggcaggcca aggagctgct ggaccacctg  8940
gaaggcatca tctccaacga gccagtggag gtcaggcgca cacacccct gccaccccc    9000
accattcccc tcttccctc cccctccccc tcccctccc ctccccttctc cccccccc      9060
gccttccctt cagtccctc caggagcacc ctgcccgcca ccccccccgc cacaccgctc    9120
ctttgtgacc ccggcgttgc gtgctgccgc gccttgcgcc cccaggccag acgccgctgc   9180
gacaacccc ctccccccc aaaccttct atccccccc ccccccgc ccgccgtcc           9240
gccccgttc caagcaagca tctacttgca caggcatgca tggcgccatg cgtccacccc    9300
ctgcagggtt gacagtgtgt ccctctcccc cttcccccct ccccgcccc tgctgcagat    9360
tgtggcgggc cagaacatcg tggaggtgaa gccgcaggga gtgagcaagg gcaaggtggt   9420
ggagcgcatc ctgcacgact gcctcaccgc cagccaggcg ccggagtttg tgctgtgcgt   9480
gggggacgac agatcaggtg cgggtgggaa gcgggtgtt gggagggggg aagggctggg    9540
ggcacgggcg ggcgggtggc tggattgcag ggcgagcaac aacctccatt ggtgcaaggt   9600
ctgtggtgtg acgtgctgtg ctgtgctgtg ccgtccctgg gtgagccgtg ctgtgctgtg   9660
ctgtgcagac gaggacatgt tcactgccat ggagaacatg cagttctccc cccacatgcc   9720
ggtggaggta tttgcatgca cggtggggca gaagccgagc aaggcgccct tctacgtcaa   9780
cgacccggca gaggtgggtg gatgtggtag caggatgtgc ggggggaagg gggggaagg    9840
ggcgtccgcc cctgaaaccc atgggattgg ggaggggga ggggggatgc acctctga      9898

<210> SEQ ID NO 50
<211> LENGTH: 900
```

-continued

```
<212> TYPE: DNA
<213> ORGANISM: Parachlorella sp
<220> FEATURE:
<221> NAME/KEY: misc_feature
<223> OTHER INFORMATION: RNA binding domain, cds, encodes SEQ ID 1

<400> SEQUENCE: 50
atgtcctcgg aggaaataag caaagatatg gaggaagcaa gcagcagcgg ggatggaggg      60
ggaaaattat ttctcggagg tttaagttgg gacacaacgg aagagaaatt aagggaacat     120
tttggcgtat atggcgatat tcacgaagct gtggtcatga aggataggac gactgggcga     180
ccgcgaggat tcggatttgt tactttcaaa gatgcggagg ttgcagacag ggttgttcaa     240
gatatccacg tgattgatgg cagacagata gacgcgaaga aatctgtacc gcaagagcaa     300
aagccgaagg ctcgaaaaat atttgttggc gggctcgcac ctgaaactac agaggcggat     360
ttcaaagagt attttgaacg atatggctcg ataagcgacg ttcaaataat gcaagatcat     420
atgacaggcc ggtcgagggg cttcgggttc attacttttg aggaggacgc agcagtagag     480
aaggtgtttg cccagggcgc catgcaagag cttggtggca agcgcattga aatcaagcat     540
gccactccca aggggtctag ctcaccaacc actcctgggg ggaggagttc tagtggaggc     600
agagggcagg gctatggcag agccatgcca atgcctttcg gtcaacttgc cggatccccc     660
tatgggtatg gcttgtttca cttccctcca ggcgtgatgc cccatgccac ccctacagc     720 atgggctacg ccaacccta cctgatgatg cagcaaatca gcggctaccc cggcgccacg     780
ccgtatccat ttgccggcct gtatggcggg caggggcgtg gagcctcgca gcagctgcag     840
caggctcagc acacgtcaca gcagctgtct tcctcgggag cggggcccgt gactcgcctg     900
```